US011076873B2

(12) United States Patent
Morvan

(10) Patent No.: US 11,076,873 B2
(45) Date of Patent: Aug. 3, 2021

(54) PATIENT SPECIFIC HUMERAL CUTTING GUIDES

(71) Applicant: Howmedica Osteonics Corp., Mahwah, NJ (US)

(72) Inventor: Yannick Morvan, Plouzané (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 83 days.

(21) Appl. No.: 16/032,005

(22) Filed: Jul. 10, 2018

(65) Prior Publication Data

US 2019/0015113 A1 Jan. 17, 2019

Related U.S. Application Data

(60) Provisional application No. 62/530,984, filed on Jul. 11, 2017, provisional application No. 62/656,100, filed on Apr. 11, 2018.

(51) Int. Cl.
*A61B 17/17* (2006.01)
*A61B 34/10* (2016.01)
(Continued)

(52) U.S. Cl.
CPC .......... *A61B 17/1778* (2016.11); *A61B 17/15* (2013.01); *A61B 17/1684* (2013.01);
(Continued)

(58) Field of Classification Search
CPC . A61B 17/17; A61B 17/1778; A61B 17/1735; A61B 34/10; A61F 2/46; A61F 2/4612
See application file for complete search history.

(56) References Cited

U.S. PATENT DOCUMENTS 4,919,670 A 4/1990 Dale et al.
5,030,219 A 7/1991 Matsen, III et al.
(Continued)

FOREIGN PATENT DOCUMENTS

CA 2927086 4/2015
CA 2927811 4/2015
(Continued)

OTHER PUBLICATIONS

US 9,451,972 B2, 09/2016, Lang et al. (withdrawn)
(Continued)

*Primary Examiner* — Christopher J Beccia
(74) *Attorney, Agent, or Firm* — Duane Morris LLP

(57) ABSTRACT

A humeral guide is provided that has a first portion or member configured to be positioned on a portion of a proximal humerus. The first portion or member can be configured to rest in a complementary manner on the portion of the proximal humerus. The humeral guide can be configured with apertures defining trajectories through bone, the pin trajectories being diverging in some case and in some cases being selected to enhanced support. A second portion or member and a third portion or member of the humeral guide are configured to be positioned on first and second lateral portions of the humerus distal to a location intended for resection, e.g., between an anatomical neck and a distal end of the humerus. The second and third portions or members or portions are configured to rest in a complementary manner on the first and second lateral portions of the humerus. The humeral guide can be configured to avoid soft tissue between a bone facing side and the humerus. The humeral guide can have a removeable jig portion.

13 Claims, 60 Drawing Sheets

(51) Int. Cl.
   *A61B 17/15* (2006.01)
   *A61F 2/46* (2006.01)
   *A61B 17/16* (2006.01)

(52) U.S. Cl.
   CPC .......... *A61B 17/1735* (2013.01); *A61B 34/10* (2016.02); *A61F 2/4612* (2013.01); *A61B 2034/104* (2016.02); *A61B 2034/105* (2016.02); *A61B 2034/108* (2016.02); *A61F 2002/4681* (2013.01); *A61F 2002/4687* (2013.01)

(56) References Cited

U.S. PATENT DOCUMENTS

| | | |
|---|---|---|
| 5,329,846 A | 7/1994 | Bonutti |
| 5,383,938 A | 1/1995 | Rohr et al. |
| 5,458,637 A | 10/1995 | Hayes |
| 5,531,793 A | 7/1996 | Kelman et al. |
| 5,610,966 A | 3/1997 | Martell et al. |
| 5,725,586 A | 3/1998 | Sommerich |
| 5,768,134 A | 6/1998 | Swaelens et al. |
| 5,769,856 A | 6/1998 | Dong et al. |
| 5,779,710 A | 7/1998 | Matsen, III |
| 5,807,437 A | 9/1998 | Sachs et al. |
| 5,824,078 A | 10/1998 | Nelson et al. |
| 5,824,085 A | 10/1998 | Sahay et al. |
| 6,002,859 A | 12/1999 | DiGioia, III et al. |
| 6,129,764 A | 10/2000 | Servidio |
| 6,172,856 B1 | 1/2001 | Jang |
| 6,183,519 B1 | 2/2001 | Bonnin et al. |
| 6,364,910 B1 | 4/2002 | Shultz et al. |
| 6,385,475 B1 | 5/2002 | Cinquin et al. |
| 6,432,142 B1 | 8/2002 | Kamiya et al. |
| 6,459,948 B1 | 10/2002 | Ateshian et al. |
| 6,648,894 B2 | 11/2003 | Abdelgany et al. |
| 6,772,026 B2 | 8/2004 | Bradbury et al. |
| 6,797,006 B2 | 9/2004 | Hodorek |
| 6,849,223 B2 | 2/2005 | Dean et al. |
| 6,915,150 B2 | 7/2005 | Cinquin et al. |
| 6,944,518 B2 | 9/2005 | Roose |
| 7,175,665 B2 | 2/2007 | German et al. |
| 7,468,075 B2 | 12/2008 | Lang et al. |
| 7,469,474 B2 | 12/2008 | Farrar |
| 7,534,263 B2 | 5/2009 | Burdulis, Jr. et al. |
| 7,599,539 B2 | 10/2009 | Kunz et al. |
| 7,618,451 B2 | 11/2009 | Berez et al. |
| 7,634,119 B2 | 12/2009 | Tsougarakis et al. |
| 7,648,530 B2 | 1/2010 | Habermeyer et al. |
| 7,702,380 B1 | 4/2010 | Dean |
| 7,717,956 B2 | 5/2010 | Lang |
| 7,747,305 B2 | 6/2010 | Dean et al. |
| 7,796,791 B2 | 9/2010 | Tsougarakis et al. |
| 7,799,077 B2 | 9/2010 | Lang et al. |
| 7,802,503 B2 | 9/2010 | Couvillion et al. |
| 7,822,588 B2 | 10/2010 | Mueller et al. |
| 7,831,079 B2 | 11/2010 | Kunz et al. |
| 7,892,287 B2 | 2/2011 | Deffenbaugh |
| 7,927,338 B2 | 4/2011 | Laffargue et al. |
| 7,981,158 B2 | 7/2011 | Fitz et al. |
| 7,983,777 B2 | 7/2011 | Melton et al. |
| 7,993,408 B2 | 8/2011 | Meridew et al. |
| 8,007,448 B2 | 8/2011 | Barrera |
| 8,014,984 B2 | 9/2011 | Iannotti et al. |
| 8,055,487 B2 | 11/2011 | James |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,234,097 B2 | 7/2012 | Steines et al. |
| 8,337,501 B2 | 12/2012 | Fitz et al. |
| 8,337,503 B2 | 12/2012 | Lian |
| 8,337,507 B2 | 12/2012 | Lang et al. |
| 8,343,218 B2 | 1/2013 | Lang et al. |
| 8,350,186 B2 | 1/2013 | Jones et al. |
| 8,366,771 B2 | 2/2013 | Burdulis, Jr. et al. |
| 8,377,073 B2 | 2/2013 | Wasielewski |
| 8,377,129 B2 | 2/2013 | Fitz et al. |
| 8,439,926 B2 | 5/2013 | Bojarski et al. |
| 8,457,930 B2 | 6/2013 | Schroeder |
| 8,460,304 B2 | 6/2013 | Fitz et al. |
| 8,475,463 B2 | 7/2013 | Lian |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,532,806 B1 | 9/2013 | Masson |
| 8,535,319 B2 | 9/2013 | Ball |
| 8,545,509 B2 | 10/2013 | Park et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,731,885 B2 | 5/2014 | Iannotti et al. |
| 8,735,773 B2 | 5/2014 | Lang |
| 8,744,148 B2 | 6/2014 | Nord et al. |
| 8,768,028 B2 | 7/2014 | Lang et al. |
| 8,771,365 B2 | 7/2014 | Bojarski et al. |
| 8,774,900 B2 | 7/2014 | Buly et al. |
| 8,775,133 B2 | 7/2014 | Schroeder |
| 8,781,557 B2 | 7/2014 | Dean et al. |
| 8,814,942 B2 | 8/2014 | Anthony et al. |
| 8,843,229 B2 | 9/2014 | Vanasse et al. |
| 8,864,769 B2 | 10/2014 | Stone et al. |
| 8,882,847 B2 | 11/2014 | Burdulis, Jr. et al. |
| 8,884,618 B2 | 11/2014 | Mahfouz |
| 8,888,855 B2 | 11/2014 | Roche et al. |
| 8,898,043 B2 | 11/2014 | Ashby et al. |
| 8,906,107 B2 | 12/2014 | Bojarski et al. |
| 8,926,706 B2 | 1/2015 | Bojarski et al. |
| 8,932,361 B2 | 1/2015 | Tornier et al. |
| 8,932,363 B2 | 1/2015 | Tsougarakis et al. |
| 8,934,961 B2 | 1/2015 | Lakin et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,971,606 B2 | 3/2015 | Chaoui |
| 8,974,539 B2 | 3/2015 | Bojarski et al. |
| 8,984,731 B2 | 3/2015 | Broeck et al. |
| 8,989,460 B2 | 3/2015 | Mahfouz |
| 8,992,538 B2 | 3/2015 | Keefer |
| 8,998,915 B2 | 4/2015 | Fitz et al. |
| 9,020,788 B2 | 4/2015 | Lang |
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |

(56) References Cited

U.S. PATENT DOCUMENTS

| | | |
|---|---|---|
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,208,558 B2 | 12/2015 | Dean et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,275,191 B2 | 3/2016 | Dean et al. |
| 9,278,413 B2 | 3/2016 | Sperling |
| 9,292,920 B2 | 3/2016 | Dean et al. |
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,330,206 B2 | 5/2016 | Dean et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,615,839 B2 | 4/2017 | Olson |
| 9,626,756 B2 | 4/2017 | Dean et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,672,302 B2 | 6/2017 | Dean et al. |
| 9,672,617 B2 | 6/2017 | Dean et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,068,671 B2 | 9/2018 | Dean et al. |
| 10,085,839 B2 | 10/2018 | Wong et al. |
| 10,405,993 B2 | 9/2019 | Deransart et al. |
| 10,716,676 B2 | 7/2020 | Tornier et al. |
| 2001/0047210 A1 | 11/2001 | Wolf |
| 2002/0007294 A1 | 1/2002 | Bradbury et al. |
| 2002/0025358 A1 | 2/2002 | Nelson et al. |
| 2002/0082741 A1 | 6/2002 | Mazumder et al. |
| 2003/0139818 A1 | 7/2003 | Rogers et al. |
| 2004/0045934 A1 | 3/2004 | Harvey et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0171924 A1 | 9/2004 | Mire et al. |
| 2004/0181144 A1 | 9/2004 | Cinquin et al. |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0112397 A1 | 5/2005 | Rolfe et al. |
| 2005/0197814 A1 | 9/2005 | Aram |
| 2005/0216305 A1 | 9/2005 | Funderud |
| 2006/0100714 A1 | 5/2006 | Ensign |
| 2006/0136058 A1 | 6/2006 | Pietrzak |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0191741 A1 | 8/2007 | Tsai et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0109000 A1 | 5/2008 | Maroney et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2009/0204225 A1 | 8/2009 | Meridew et al. |
| 2009/0226068 A1 | 9/2009 | Fitz et al. |
| 2009/0254091 A1* | 10/2009 | Long .................. A61B 17/1778 606/87 |
| 2009/0264894 A1 | 10/2009 | Wasielewski |
| 2009/0292464 A1 | 11/2009 | Fuchs et al. |
| 2010/0087927 A1 | 4/2010 | Roche et al. |
| 2010/0161066 A1 | 6/2010 | Iannotti et al. |
| 2010/0191100 A1 | 7/2010 | Anderson et al. |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0119884 A1 | 5/2011 | Ratron |
| 2011/0137424 A1 | 6/2011 | Lappin et al. |
| 2011/0144760 A1 | 6/2011 | Wong et al. |
| 2011/0282403 A1 | 11/2011 | Anthony et al. |
| 2012/0078258 A1 | 3/2012 | Lo et al. |
| 2012/0116203 A1 | 5/2012 | Vancraen et al. |
| 2012/0130434 A1 | 5/2012 | Stemniski |
| 2012/0141034 A1 | 6/2012 | Iannotti et al. |
| 2012/0143267 A1 | 6/2012 | Iannotti et al. |
| 2012/0221112 A1 | 8/2012 | Lappin |
| 2012/0232670 A1 | 9/2012 | Bojarski et al. |
| 2012/0253350 A1 | 10/2012 | Anthony et al. |
| 2012/0276509 A1 | 11/2012 | Iannotti et al. |
| 2012/0279933 A1 | 11/2012 | Hensler et al. |
| 2013/0053968 A1 | 2/2013 | Nardini et al. |
| 2013/0110116 A1 | 5/2013 | Kehres et al. |
| 2013/0110470 A1 | 5/2013 | Vanasse et al. |
| 2013/0110471 A1 | 5/2013 | Lang et al. |
| 2013/0114873 A1 | 5/2013 | Chaoui |
| 2013/0150975 A1 | 6/2013 | Iannotti et al. |
| 2013/0172898 A1 | 7/2013 | Iannotti et al. |
| 2013/0190882 A1 | 7/2013 | Humphrey |

(56) References Cited

U.S. PATENT DOCUMENTS

| | | |
|---|---|---|
| 2013/0211531 A1 | 8/2013 | Steines et al. |
| 2013/0245631 A1 | 9/2013 | Bettenga |
| 2013/0261629 A1 | 10/2013 | Anthony et al. |
| 2013/0274752 A1 | 10/2013 | Trouilloud et al. |
| 2013/0338673 A1 | 12/2013 | Keppler |
| 2014/0039633 A1 | 2/2014 | Roche et al. |
| 2014/0257499 A1 | 9/2014 | Winslow et al. |
| 2014/0276867 A1 | 9/2014 | Kelley et al. |
| 2014/0371863 A1 | 12/2014 | Vanasse et al. |
| 2015/0045903 A1 | 2/2015 | Neal |
| 2015/0054195 A1 | 2/2015 | Greyf |
| 2015/0093283 A1 | 4/2015 | Miller et al. |
| 2015/0150688 A1 | 6/2015 | Vanasse et al. |
| 2015/0202045 A1 | 7/2015 | Early et al. |
| 2015/0223941 A1 | 8/2015 | Lang |
| 2015/0250552 A1 | 9/2015 | Radermacher et al. |
| 2015/0250597 A1 | 9/2015 | Lang et al. |
| 2015/0320430 A1* | 11/2015 | Kehres .................. A61B 17/15 606/87 |
| 2015/0328004 A1 | 11/2015 | Mafhouz |
| 2016/0015466 A1 | 1/2016 | Park et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0374697 A1* | 12/2016 | Kehres .................. A61F 2/4612 606/87 |
| 2017/0000614 A1 | 1/2017 | Mahfouz |
| 2017/0000615 A1 | 1/2017 | Mahfouz |
| 2017/0027587 A1 | 2/2017 | Fraone et al. |
| 2017/0027593 A1 | 2/2017 | Bojarski et al. |
| 2017/0056024 A1 | 3/2017 | Chao |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1 | 10/2017 | Hatzidakis et al. |
| 2017/0360567 A1 | 12/2017 | Fitz et al. |
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0028325 A1 | 2/2018 | Bojarski et al. |
| 2018/0161176 A1 | 6/2018 | Vivanz et al. |
| 2018/0228614 A1 | 8/2018 | Lang et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2018/0289380 A1 | 10/2018 | Mauldin et al. |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0038360 A1 | 2/2019 | Chaoui |
| 2019/0343658 A1 | 11/2019 | Deransart et al. |
| 2020/0188121 A1 | 6/2020 | Boux de Casson et al. |
| 2020/0214845 A1 | 7/2020 | Knox et al. |

FOREIGN PATENT DOCUMENTS

| | | |
|---|---|---|
| CA | 2938709 | 5/2015 |
| DE | 10 2006 047663 | 4/2008 |
| EP | 1 249 213 | 10/2002 |
| EP | 1 265 555 | 12/2002 |
| EP | 1 563 810 | 8/2005 |
| EP | 1 862 151 | 12/2007 |
| EP | 1 902 689 | 3/2008 |
| EP | 1 952 788 | 8/2008 |
| EP | 2 135 576 | 12/2009 |
| EP | 1 917 051 B1 | 6/2010 |
| EP | 2 243 445 | 10/2010 |
| EP | 2 324 801 A1 | 5/2011 |
| EP | 2 335 655 | 6/2011 |
| EP | 2 501 313 | 9/2012 |
| EP | 2 544 601 | 1/2013 |
| EP | 2583242 | 4/2013 |
| EP | 2 653 136 | 10/2013 |
| EP | 2 845 547 | 3/2015 |
| EP | 2 965 720 | 1/2016 |
| EP | 3057518 | 8/2016 |
| EP | 3057524 | 8/2016 |
| EP | 3065671 | 9/2016 |
| EP | 3068317 | 9/2016 |
| EP | 2 874 570 B1 | 1/2017 |
| EP | 3 117 801 | 1/2017 |
| FR | 2 579 454 | 10/1986 |
| FR | 2 859 099 | 3/2005 |
| FR | 2962573 A1 | 1/2012 |
| FR | 2982694 B1 | 11/2016 |
| FR | 2982979 B1 | 11/2016 |
| FR | 2982693 B1 | 12/2016 |
| GB | 2501494 A | 10/2013 |
| WO | WO 93/025157 | 12/1993 |
| WO | WO 00/35346 | 6/2000 |
| WO | WO 00/59411 | 10/2000 |
| WO | WO 02/061688 | 8/2002 |
| WO | WO 2010/120346 | 10/2010 |
| WO | WO 2011/110374 | 9/2011 |
| WO | WO 2011/154891 | 12/2011 |
| WO | WO 2011/157961 | 12/2011 |
| WO | WO 2012/021241 | 2/2012 |
| WO | WO 2012/058349 | 5/2012 |
| WO | WO 2012/125319 | 9/2012 |
| WO | WO 2013/060851 | 5/2013 |
| WO | WO 2013/062848 | 5/2013 |
| WO | WO 2013/062851 | 5/2013 |
| WO | WO 2013/142998 | 10/2013 |
| WO | WO 2014/020561 | 2/2014 |
| WO | WO 2014/035991 | 3/2014 |
| WO | WO 2014/180972 | 11/2014 |
| WO | WO 2015/052586 | 4/2015 |
| WO | WO 2015/056097 | 4/2015 |
| WO | WO 2015/068035 | 5/2015 |
| WO | WO 2015/071757 | 5/2015 |
| WO | WO 2015/175397 | 11/2015 |
| WO | WO 2015/185219 | 12/2015 |
| WO | WO 2017/005514 | 1/2017 |
| WO | WO 2017/007565 | 1/2017 |
| WO | WO 2017/091657 | 6/2017 |
| WO | WO 2017/105815 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |

(56) References Cited

FOREIGN PATENT DOCUMENTS

| WO | WO 2019/014281 | 1/2019 |
|---|---|---|
| WO | WO 2019/033037 | 2/2019 |
| WO | WO 2019/060780 | 3/2019 |

OTHER PUBLICATIONS

Boileau, et al., "The three-dimensional geometry of the proximal humerus: implications for surgical technique and prosthetic design." The Journal of bone and joint surgery. British vol. 79.5 (1997): 857-865.
Dougherty, "Digital Image Processing for Medical Applications," May 11, 2009 (May 11, 2009), Cambridge University Press, XP002615721.
Favre, et al., "Influence of component positioning on impingement in conventional total shoulder arthroplasty," Clinical Biomechanics, Butterworth Scientifics, Nov. 5, 2007, pp. 174-183, vol. 23, No. 2, Guilford, GB.
Gregory, et al.,"Accuracy of Glenoid Component Placement in Total Shoulder Arthroplasty and its Effect on Clinical and Radiological Outcome in a Retrospective, Longitudinal, Monocentric Open Study," PLOS One, p. e75791, Aug. 1, 2013, vol. 8, No. 10.
Habets, et al., Computer assistance in orthopaedic surgery. Technische Universiteit Eindhoven, 2002.
Hempfing, et al. "Surgical landmarks to determine humeral head retrotorsion for hemiarthroplasty in fractures." Journal of shoulder and elbow surgery 10.5 (2001): 460-463.
Hernigou, et al., "Determining humeral retroversion with computed tomography." Journal of bone and joint surgery. Oct. 2002;84-A(10):1753-62.
Iannotti et al., "Prosthetic positioning in total shoulder arthroplasty," Journal of Shoulder and Elbow Surgery, Jan. 1, 2005, vol. 14, No. 1S, pp. S111-S121.
Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.
Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.
Lee, C.C. et al., "Recognizing Abdominal Organs in CT Images Using Contextual Neural Network and Fuzzy Rules", Engineering in Medicine and Biology Society, 2000. Proceedings of the 22nd Annual International Conference of the IEEE Jul. 23-28, 2000, Piscataway, NJ, USA, IEEE, vol. 3, Jul. 23, 2000 (Jul. 23, 2000), pp. 1745-1748, XP010530837.
Ma, et al., "Robust registration for computer-integrated orthopedic surgery: laboratory validation and clinical experience." Medical image analysis 7.3 (2003): 237-250.
"Olympia Total Shoulder System Surgical Technique", Wright Medical Technology, 2001, in 19 pages.
Nguyen, et al., "A New Segmentation Method for MRI Images of the Shoulder Joint", Computer and Robot Vision, 2007. CRV '07. Fourth Canadian Conference on, IEEE, PI, May 1, 2007 (May 1, 2007), pp. 329-338, XP031175821.
Radermacher, K., et al., "Computer Assisted Orthopaedic Surgery with Image Based Individual Templates," Clinical Orthopaedics and Related Research, No. 354, Sep. 1998, pp. 28-38.
Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.
Tamez-Pena et al., "The Integration of Automatic Segmentation and Motion Tracking for 4D Reconstruction and Visualization of Musculoskeletal Structures," Biomedical Image Analysis, 1998. Proceedings. Workshop on Santa Barbara, CA US, Jun. 26-27, 1998, Los Alamitos, CA, USA, IEEE Comput. Soc. US, Jun. 26, 1998 (Jun. 26, 1998), pp. 154-163, XP010291418.
Tornier, "Salto Talaris, Total Ankle Prosthesis", 2009.
Valstar, et al. "Towards computer-assisted surgery in shoulder joint replacement." ISPRS journal of photogrammetry and remote sensing 56.5-6 (2002): 326-337.
Valstar, et al. "The use of Roentgen stereophotogrammetry to study micromotion of orthopaedic implants." ISPRS journal of photogrammetry and remote sensing 56.5-6 (2002): 376-389.
Welsh, et al., "CT-based preoperative analysis of scapula morphology and glenohumeral joint geometry." Computer Aided Surgery 8.5 (2003): 264-268.
Wu, et al. "An interface for the data exchange between CAS and CAD/CAM systems." International Congress Series. vol. 1256. Elsevier, 2003.
Zimmer, "Zimmer® PSI Shoulder Trabecular MetalTM Reverse Glenoid Base Plate Surgical Technique", Dec. 30, 2013.
"Zimmer® PSI Shoulder Planning", Zimmer Biomet TV, posted Jul. 11, 2014, retrieved from internet on Jan. 9, 2020, <https://zimmerbiomet.tv/videos/1025?a=surgeon&version=1190>.
International Search Report and Written Opinion issued in PCT Application No. PCT/US2018/041531, dated Dec. 11, 2018, in 18 pages.
Final Office Action issued in connection with U.S. Appl. No. 15/426,720, 15 pages, dated Apr. 29, 2021.

* cited by examiner

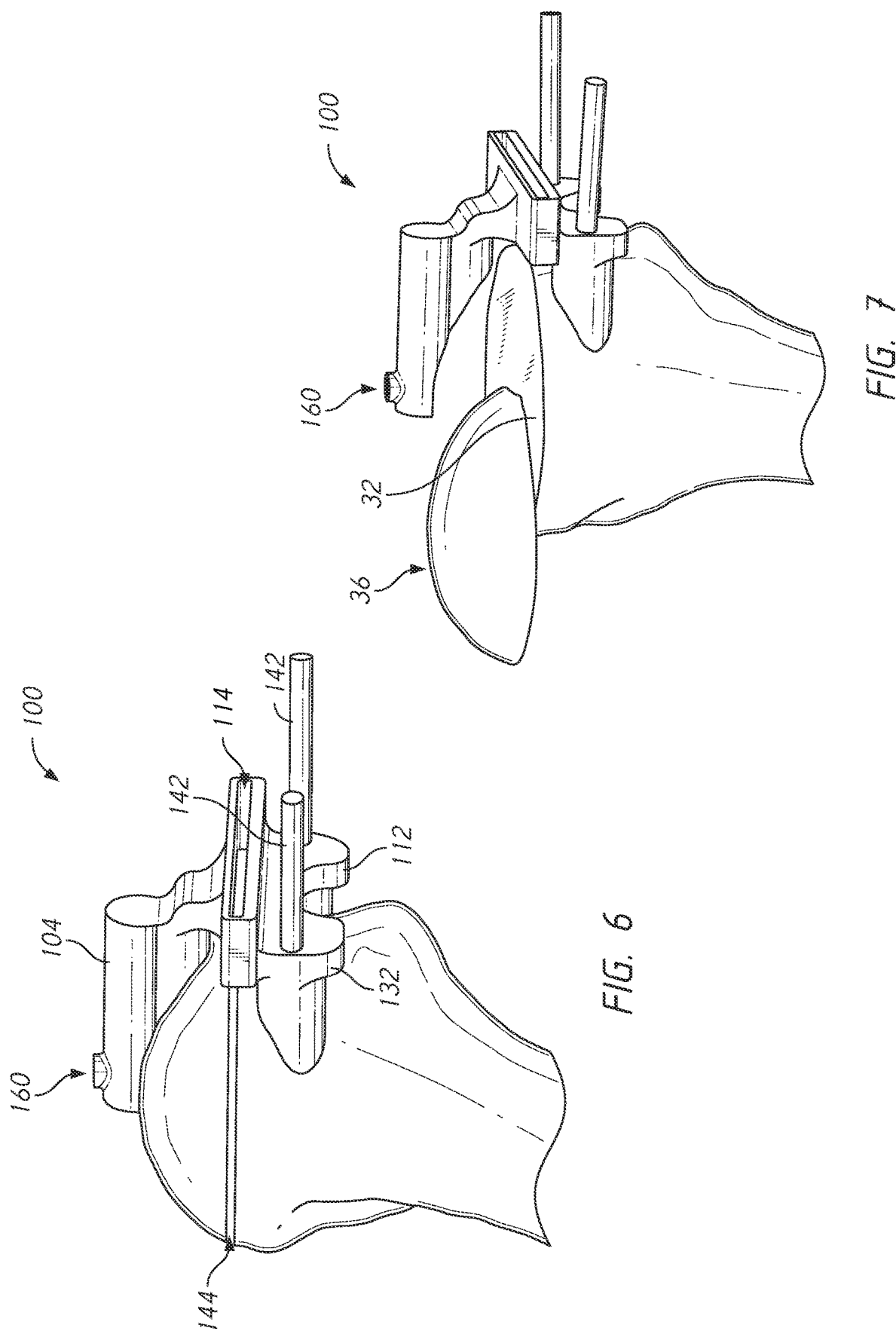

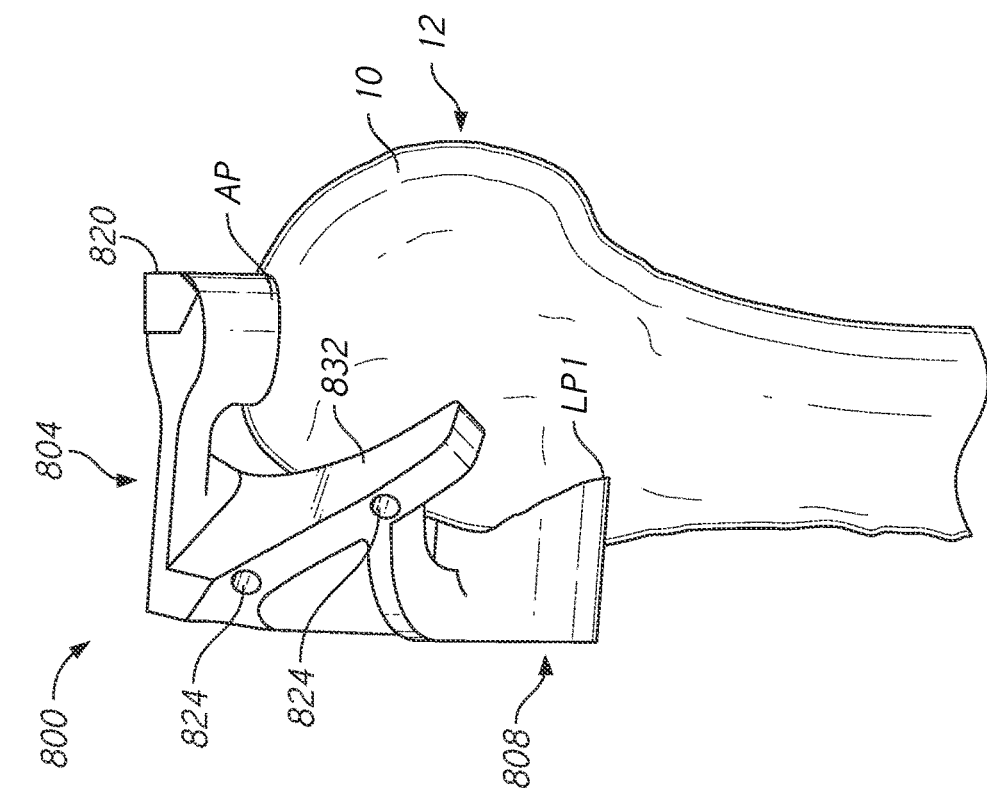
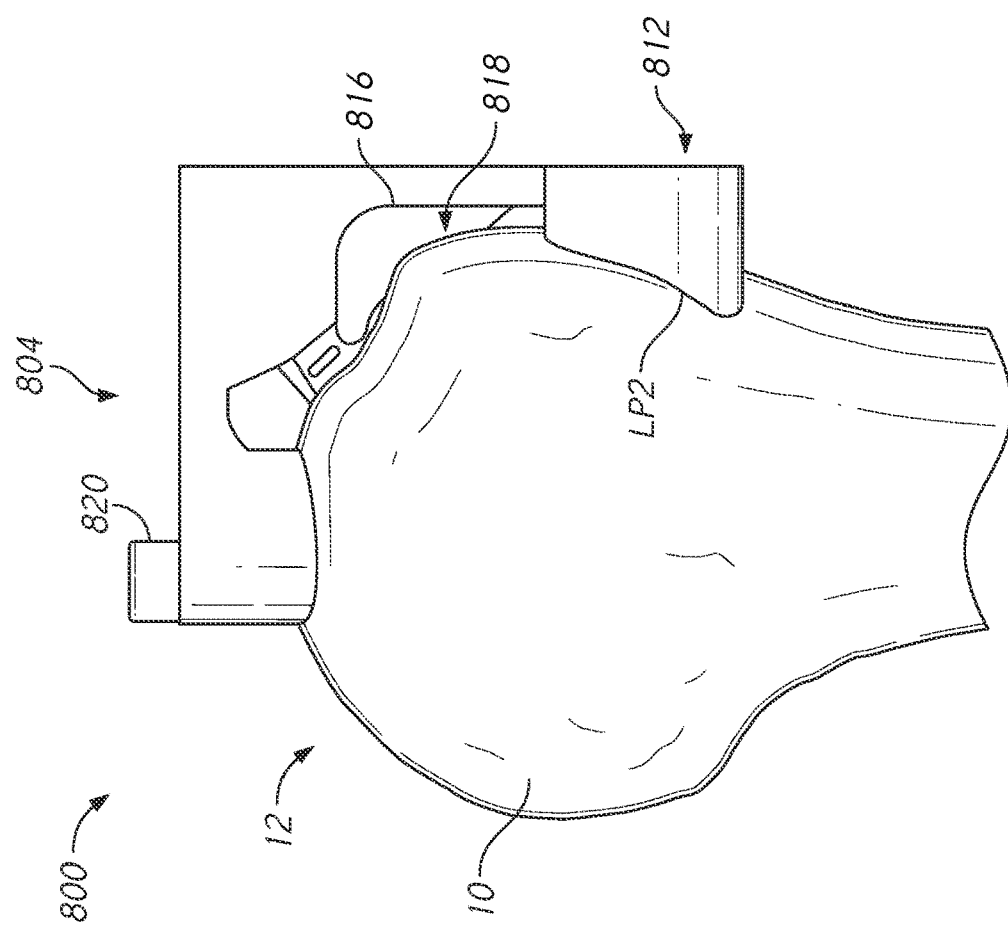

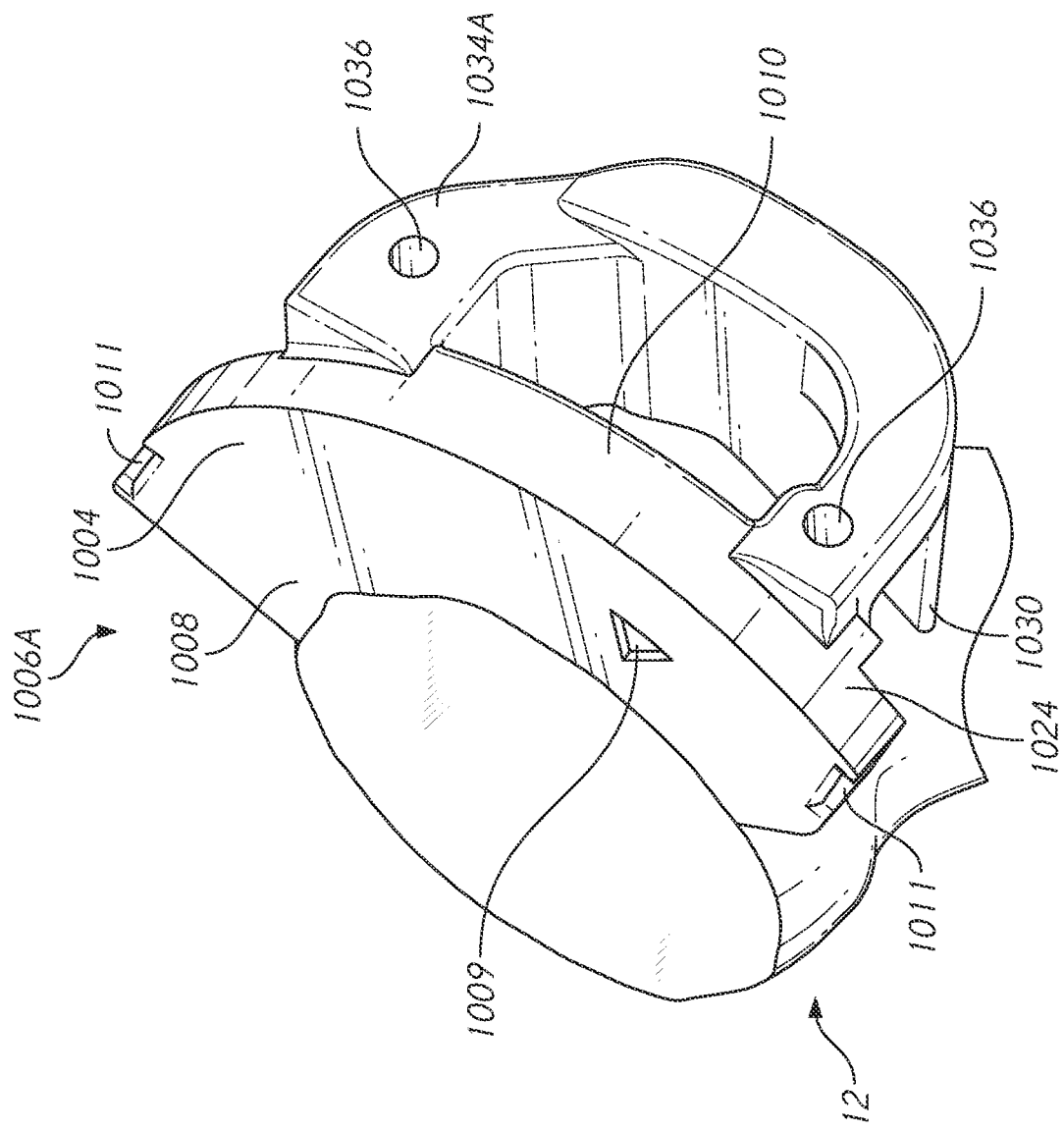

PATENT SPECIFIC HUMERAL CUTTING GUIDES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to guides for assisting in the preparation of end portions of long bones as part of a joint replacement or repair procedures, particularly for preparing a proximal (or superior) portion of a humerus for implanting a humeral component of an artificial joint.

Description of the Related Art

Arthroplasty is the standard of care for the treatment of shoulder joint arthritis. A typical humeral head replacement is implanted following exposure of the head of the humerus, resection of the head and various procedures to create space in the humerus for sub-surface stems or anchors to which an artificial head can be coupled. The humeral head replacement might articulate with the native bone or an opposing glenoid resurfacing device, which may be manufactured from UHMWPE or any other acceptable material.

For more severe cases of shoulder arthritis, the standard treatment is a reverse reconstruction, which includes reversing the kinematics of the shoulder joint. This is performed by securing a semi-spherical device to the glenoid, referred to as a glenoid sphere, and implanting a humeral stem with a modular cavity capable of receiving the glenoid sphere. The humeral stem is usually offered in one fixed inclination angle between 135 degrees and 155 degrees, with 155 degrees being the angle currently preferred by a majority of surgeons.

An initial step to preparing the humerus involves resecting the humeral head. Following resection, an awl may be used to create a space distal the resection plane in which the stem or other anchor can be disposed. The movement of the saw in resection and the awl in preparing the resected humerus are typically done either free hand or on guides that are placed by gross alignment techniques such as eyeballing the exposed humerus. While these approaches provide a minimum level of care they are not highly accurate or likely to comply with any pre-operative surgical plan.

SUMMARY OF THE INVENTION

It would be desirable to provide improved apparatuses and methods for preparing a human humerus to be coupled with a shoulder joint prosthesis component. An improvement over the prior art would to implement such improved apparatuses and methods using pre-operative image data from a patient preparing to undergo shoulder arthroplasty and also using patient specific guides formed with reference to the pre-operative image data. It would further be advantageous to provide the embodiments and the advantages thereof as discussed below.

A method can be provided for surgically adapting a humerus having a humeral head and an anatomical neck. The method can include positioning a first member of a humeral guide on a portion of a proximal humerus. As used in this context, a portion of a proximal humerus refers to a portion of the humerus that is adjacent to the scapula and forms part of the shoulder joint. A proximal portion of the humerus is sometimes referred to herein as a superior portion humerus. The first member rests in a complementary manner on the portion of the proximal humerus. A second member and a third member of the humeral guide are positioned on first and second lateral portions of the humerus distal to a location intended for resection, e.g., distal to an anatomical neck of the humerus. As used in this context, a location that is distal to another location refers to being closer to an interior or elbow adjacent end of the humerus. A distal portion of the humerus is sometimes referred to herein as an inferior portion of the humerus. The second and third members rest in a complementary manner on the first and second lateral portions of the humerus. The humeral guide is secured to the humerus. A portion of the humeral head is resected at the location intended for resection, e.g., proximal of the anatomical neck, to create a resected portion and an exposed cancellous surface while the first member of the humeral guide remains in place on the proximal humerus. The resected portion of the humeral head is removed from the exposed surface. A guide pin is positioned through a guide pin aperture disposed at or adjacent to the first member of the humeral guide into the exposed cancellous surface after removing the resected portion from the exposed surface. The humeral guide is removed after removing the resected portion of the humerus. The exposed cancellous surface is modified with reference to the guide pin.

In another embodiment a humeral patient specific lateral cutting guide is provided that includes a first portion, a second portion and a third portion. The first portion is configured to be complementary to a first portion of a humerus of a specific patient. The second portion is configured to be complementary to a first lateral portion of the humerus distal to a location intended for resection, e.g., distal to an anatomical neck of the humerus, of the specific patient. The third portion is configured to be complementary to a second lateral portion of the humerus distal to the location intended for resection, e.g., the anatomical neck of the humerus of the specific patient, spaced apart from the first lateral portion. The guide also can optionally include a plurality of mounting pin apertures disposed non-parallel to each other. The guide also includes a resection plane configured to be disposed between the non-parallel mounting pin apertures and a superior end of the humerus. The first portion of the cutting guide is configured to be placed distal to both of the first lateral portion of the cutting guide and the second lateral portion of the cutting guide when the cutting guide is applied to the humerus.

In another embodiment a humeral patient specific lateral cutting guide system is provided that includes a guide body and a cutting guide. The guide body includes a concave member, a side member, and a projection. The concave member is configured to receive in a complementary fashion a portion of a humeral head of a humerus of a specific patient. The side member is coupled to the concave member. The side member is configured to engage in a complementary fashion a portion of the humerus of the specific patient distal to an anatomical neck of the humerus. The projection has a first end coupled with the concave member and a second end. The cutting guide includes a cutting plane and a coupler comprising an aperture configured to receive the projection of the guide body. The engagement of the coupler with the projection defines a proximal-distal location of the cutting plane. The proximal-distal location of the cutting plane is configured to define a lateral cut of the humeral head at a pre-defined patient specific proximal-distal location.

In another embodiment, a humeral patient specific cutting guide is provided. The cutting guide includes a first portion, a second portion, a third portion and a medial surface. The first portion is configured to be complementary to a first portion of a humerus of a specific patient. The second portion configured to be complementary to a first lateral portion of the humerus of the specific patient. The first lateral portion of the humerus can comprise a bicipital groove of the humerus. The third portion can be configured to be complementary to a second lateral portion of the humerus of the specific patient spaced apart from the first lateral portion. The second lateral portion of the humerus can comprise a greater tuberosity of the humerus. The medial surface can be disposed between the first portion and at least one of the second portion and the third portion. The medial surface can define a gap between the medial surface and a muscular insertion site of the humerus when the first portion, the second portion and the third portion are in contact with the humerus.

In one variation, the first portion of the cutting guide can comprise a protrusion. The protrusion can be configured to couple to a tube. The tube can comprise an aperture. The tube can be separable from the cutting guide.

In another embodiment, a humeral patient specific lateral cutting guide is provided that includes a first portion, a second portion, a third portion, a resection plane, and a medial surface. The first portion is configured to be complementary to an articular surface of a humerus of a specific patient. The second portion is configured to be complementary to a bicipital groove of the humerus. The third portion is configured to be complementary to a lateral portion of the humerus distal to an anatomical neck of the humerus of the specific patient. The lateral portion is spaced apart from the bicipital groove. The resection plane is configured to be disposed adjacent to a superior end of the humerus. The medial surface is disposed between the first portion and at least one of the second portion and the third portion. The medial surface defines a gap between the medial surface and a muscular insertion site of the humerus when the lateral cutting guide is applied to the humerus.

Another embodiment includes a humeral cutting guide with a resection surface, a support portion, and a releasable positioning jig. The support portion can include at least one area configured for contact with a humeral bone surface. The support portion can include a plurality of mounting pin holes. The mounting pin holes can have non-parallel longitudinal axes. The releasable positioning jig can have at least one area configured to contact the humeral head.

In another embodiment, a patient specific cutting guide is provided that includes a first portion, a second portion, and a third portion. The first portion is configured to be complementary to an articular surface of a humerus of a specific patient. The second portion is configured to be complementary to a bicipital groove of the humerus. The third portion is configured to be complementary to a portion of the humerus distal to an anatomical neck of the humerus of the specific patient, where the third portion is spaced apart from the bicipital groove. The patient specific cutting guide also has a resection plane configured to be disposed adjacent to a superior end of the humerus.

A method of resecting a humerus is provided. A multi-part guide is positioned on the humerus. The multi-part guide has a support portion and a positioning jig. At least two mounting pins are advanced through the support portion along diverging paths. The positioning jig is removed. The humerus is resected with reference to a cutting surface of the support portion.

In another embodiment, a humeral guide is provided that includes a jig having a patient matched surface and a hole for a stabilization pin. An orientation of the hole is patient matched. The humeral guide includes a stabilization pin adapted to be advanced through the hole.

In one embodiment, the orientation of the hole is patient matched in respect to a length of the pin and/or bone density along the orientation of the hole.

In another embodiment, the patient matched jig provides a minimum length of pin that traverses bone when the jig is placed in a preoperatively planned position and the stabilization pin is advanced through the hole and into the bone.

In another embodiment, the patient matched jig provides a minimum cortical bone traverse when the jig is placed in a preoperatively planned position and the stabilization pin is advanced through the hole and into the bone.

In another embodiment, the patient matched jig avoids traversing a sub-cortical cyst when the jig is placed in a preoperatively planned position and the stabilization pin is advanced through the hole and into the bone.

In another embodiment, the patient matched jig provides a minimum clearance distance from a sub-cortical cyst to the stabilization pin when the jig is placed in a preoperatively planned position and the stabilization pin is advanced through the hole.

In another embodiment, a method of planning surgery is provided. In the method, imaging information for a bone of a specific patient is obtained. A resection of the bone is planned. A cut guide is placed according to the planned resection. The bone strength is detected from the imaging information to confirm an appropriate support pin pathway to temporarily attach the cut guide to the bone.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 6 shows a stage of a method of resecting a humerus following that of FIG. 5 in which the humeral cutting guide of FIG. 4 is used to resect the humerus;

FIG. 7 shows a stage of a method of resecting a humerus following that of FIG. 6 in which the resected portion of the humerus is being removed;

FIG. 17 is a side view of the proximal humerus with a humeral guide coupled therewith;

FIG. 18 is a superior perspective view of the proximal humerus and guide illustrated in FIG. 17;

FIG. 28 is a modified embodiment of a support portion similar to that of FIG. 24, shown coupled with a humerus following resection, the support portion having multiple contact areas spaced out along a proximal distal direction of the humerus;

DETAILED DESCRIPTION OF THE PREFERRED EMBODIMENT

This application is directed to novel apparatuses and methods related to preparing a proximal humerus to receive components of a shoulder prosthesis. These novel apparatuses and methods improve preparation of the proximal humerus. In the following description, SECTION I is directed to an overview of shoulder anatomy. SECTION II is directed to a system and methods for planning aspects of apparatuses and methods herein. SECTION III is directed to various advantageous embodiments of humeral guides that facilitate preparation of the proximal humerus of the patient. SECTION IV is directed to apparatuses and methods of preparing the cancellous bone of the humerus following resection, with reference to the humeral cutting guides disclosed herein. SECTION V is directed to patient specific techniques for configuring cutting guides to enhance their stability on the humerus during the process of preparing the humerus for the implantation of a humeral shoulder component.

I. Shoulder Joint Anatomy and Surgical Preparation

Figure 1:
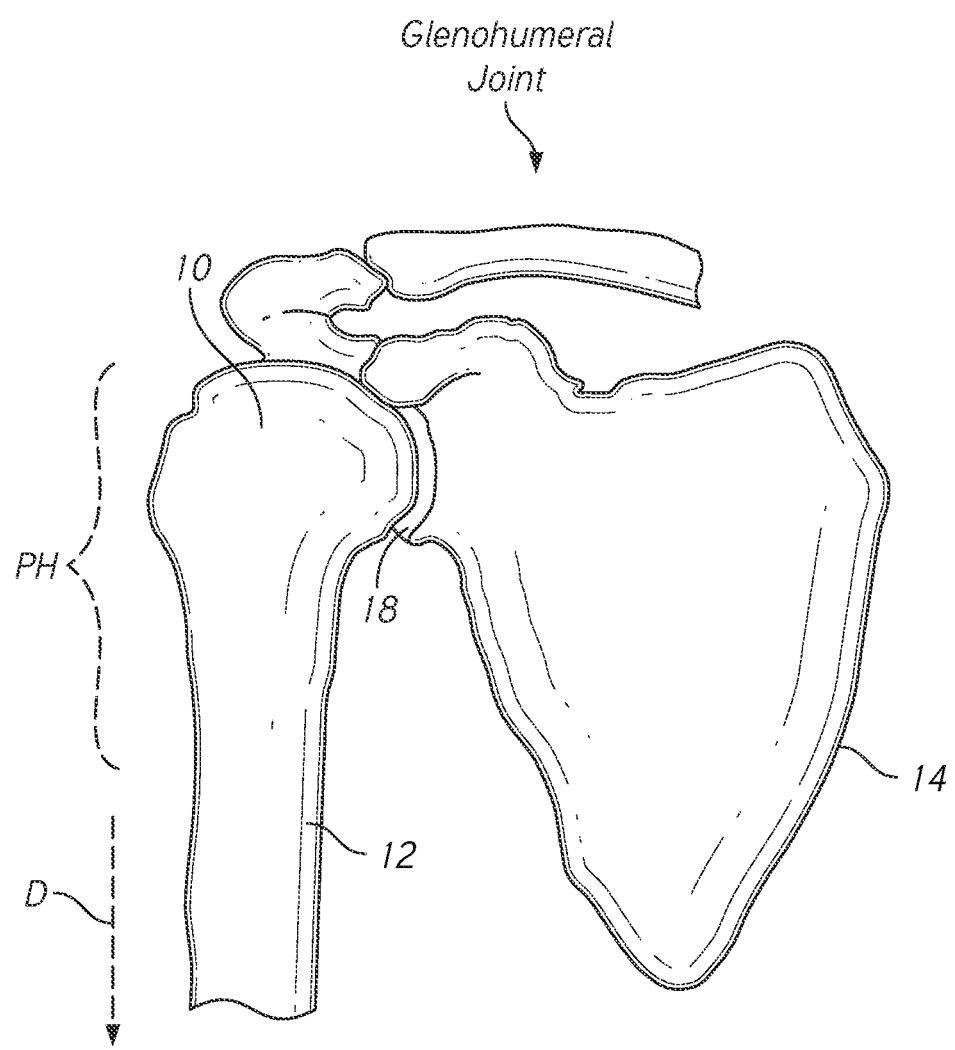
FIG. 1 is a schematic view of a human shoulder joint showing the bones thereof.

FIG. 1 shows anatomy of a glenohumeral joint. The joint is formed in part by a head 10 of a humerus 12 and a glenoid 18 of a scapula 14. The head 10 is a convex structure that is generally spherical. The glenoid 18 includes a concave articular surface upon which the head 10 moves. As discussed above, the humerus has a proximal portion that is the portion of the humerus adjacent to the glenoid 18 and forming part of the shoulder joint. The proximal humerus is sometimes referred to herein as the superior humerus. Proximal and distal in this sense are shown on FIG. 2 with reference to the humerus. In this application a location that is distal to another location refers to being closer to an inferior or elbow adjacent end of the humerus. A distal portion of the humerus is sometimes referred to herein as an inferior portion of the humerus. When the glenohumeral joint is arthritic, diseased or damaged, therapy can include forming an incision over the joint to provide access to the head 10 of the humerus 12 and the glenoid 18 of the scapula 14. Once the head 10 is accessible the head can be separated from the rest of the humerus 12 as an early part of a method of placing an implant.

Figure 2:
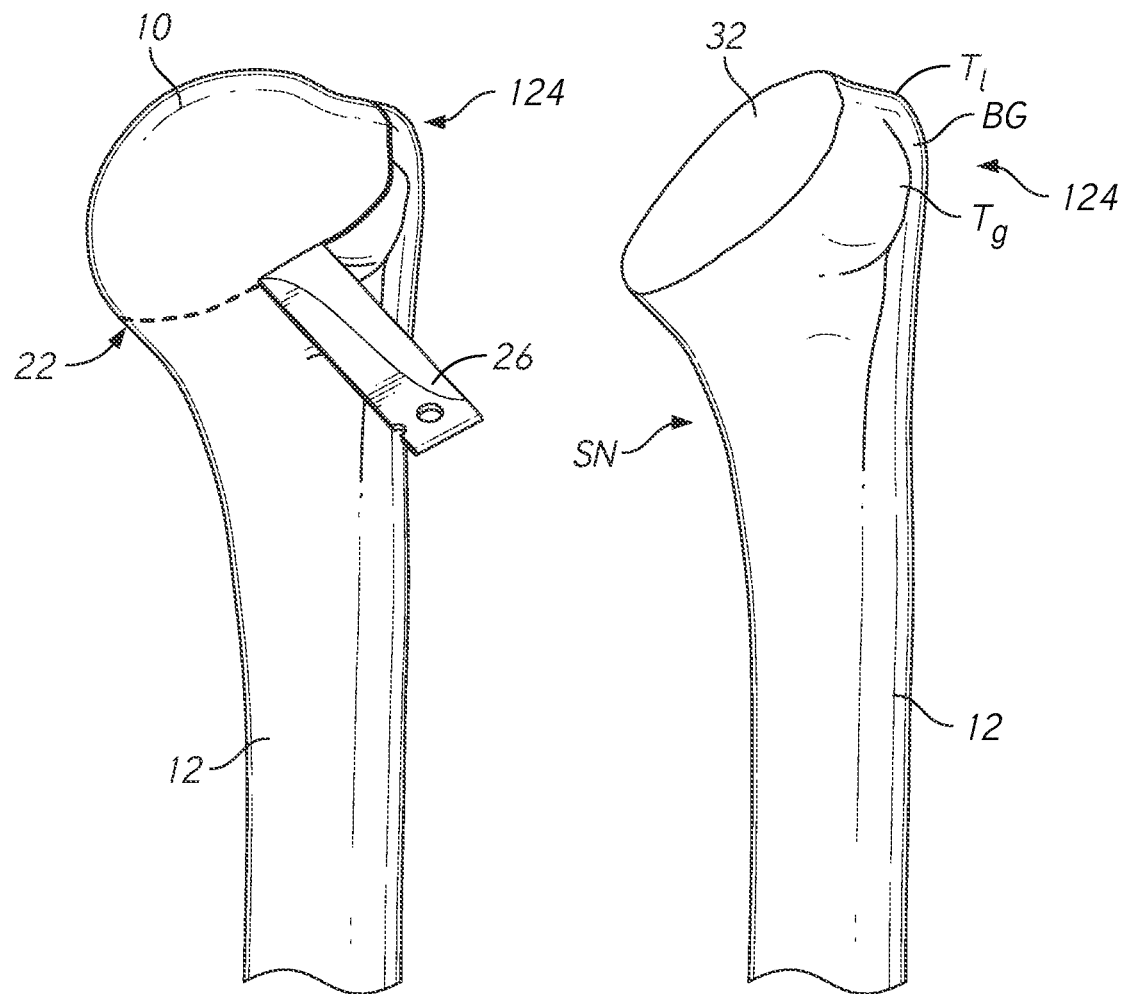
FIG. 2 is a schematic view of a human humerus in the process of being resected (left image) and having been fully resected (right image) by an orthopedic saw blade.

FIG. 2 shows that the head 10 can be severed from the rest of the humerus 12 at the anatomical neck 22 by directing a saw blade 26 along the anatomical neck 22. Guidance of the saw blade 26 can be by following a line marked directly onto the humerus 12 using a surgical marker. Once the saw blade 26 has been passed entirely along this line over the anatomical neck 22 the head 10 can be removed from the humerus 12 leaving the resected surface 32 exposed. This approach is adequate in some cases, but can be greatly improved by providing a cutting guide to assure that the resection is at a specific angle and location on the humerus 12.

II. Planning System for Enhancing Shoulder Procedures

Figure 3:
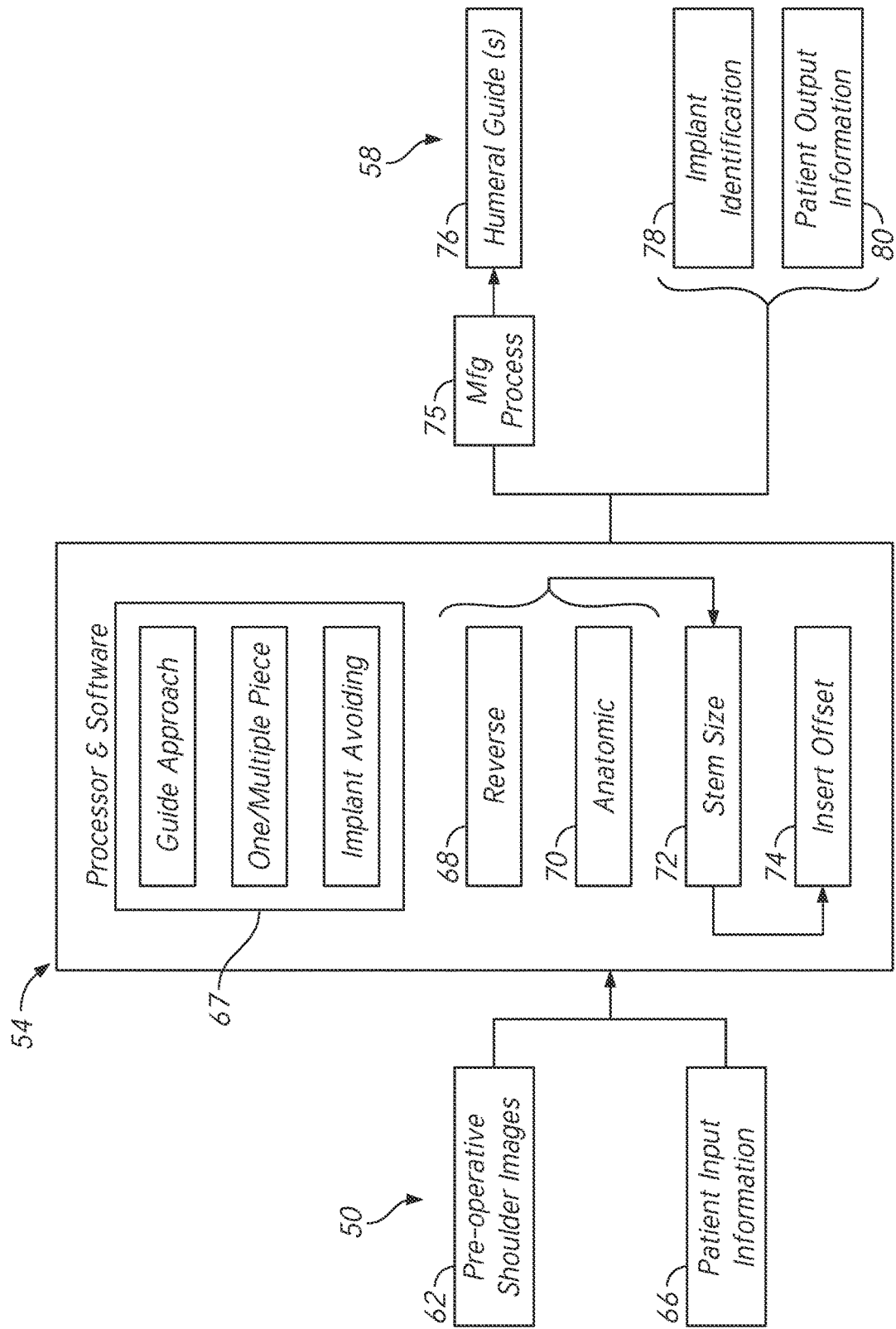
FIG. 3 is a flow chart indicating a system for preparing a patient specific humeral cutting guide apparatus.

FIG. 3 schematically illustrates a planning system 54 and corresponding methods for forming a humeral guide 76. The humeral guide 76 is formed as a patient specific guide by referencing pre-operative imaging such as MRI, CT imaging or the like. The planning system 54 receives inputs 50 and produces outputs 58 including the humeral guide 76. The inputs 50 include pre-operative shoulder images 62 and patient input information 66. The pre-operative shoulder images 62 can include MRI, CT imaging and other information that allows the planning system 54 to render or characterize the humerus 12 at least in proximity to the head 10. For example, the pre-operative shoulder images 62 can include the location and orientation of the anatomical neck 22 as well as other features of the proximal portion of the humerus 12. The pre-operative shoulder images 62 can include information about the location, shape and orientation of landmarks of the humerus 12 such as the greater tubercle $T_g$, the lesser tubercle $T_l$, the surgical neck SN, the bicipital groove BG or other landmarks of the proximal humerus 12.

The patient input information 66 can include the patients name, the shoulder being treated, other past and future therapies and other information relevant to the procedure.

The planning system 54 can include a number of modules that can process the inputs 50. The planning system 54 can include a function for selecting among reverse implant configurations 68 and anatomic implant configurations 70. The planning system 54 can include the ability to prescribe or select a stem size 72 of a humeral stem to be implanted in the humerus 12. The planning system 54 can determine an insert offset 74 which can correspond to a distance from a center of the resected surface 32 to a center of a location of an implanted stem. Each of these and other features can be determined and prescribed by the planning system 54 and can be incorporated into the outputs 58 of the planning system 54.

The outputs 58 can include a humeral guide 76, an implant identification 78, and patient procedural information 80. The humeral guide 76 that can be output by the planning system 54 can be a plan for forming a guide or can be an actual guide if the planning system 54 is configured with or coupled with a manufacturing facility or manufacturing process 75. In some applications, the process 75 that is used to form the humeral guide 76 includes additive manufacturing such as three dimensional printing. Examples of three dimensional printing include direct metal laser sintering (DMLS), fused deposition modeling (FDM), fused filament fabrication (FFF), and electron beam melting (EBM). Any one or a combination of these or other additive manufacturing processes can be used in the manufacturing process 75. In these processes a three dimensional object is formed by sequentially forming individual layers of the object on top of previously formed individual layers. These processes can closely control the gross dimensions of the object and also can form complex features and shapes such as contours. As discussed further below, these processes can be used to form complementary surface that can mate with specific anatomy of a specific patient, e.g., concave surfaces that can nest on top of corresponding convex surfaces.

With reference to FIG. 3, the planning system 54 can thus include a processor for receiving the inputs 50. The inputs 50 include the patient input information 66 and the pre-operative shoulder images 62. The processor and software process this information with other selections regarding the implant and the patient's anatomy that can be made by a user regarding the nature of the shoulder procedure. The software can produce data that can be input to the manufacturing process 75 to control the operation thereof. The data can be configured for directing a three dimensional printer or other additive manufacturing process to form the humeral guide 76. In other approaches the manufacturing process 75 can include multiple steps such as a first step of forming a mold with an additive manufacturing process and thereafter forming the humeral guide 76 in the mold. These approaches enable the pre-operative images 62 to be utilized to configure patient specific surfaces of the guide 76 to be complementary/negative surfaces such that the guide is seated according to the optimized fit as determined by the surgeon or other user. Various embodiments of the humeral guide 76 are discussed below.

The planning system 54 can also provide implant identification 78 that corresponds to the humeral guide 76. For example, the planning system 54 can provide a type of implant that the humeral guide 76 is suitable to prepare the humerus 12 to receive. For example, the implant identification 78 identifies an anatomic implant 70 with a convex articular surface to be coupled with the humerus 12. The implant identification 78 can identify a reverse implant 68 to be coupled with the humerus 12 following resection using the humeral guide 76. Furthermore, the implant identification 78 can include the stem size 72 and the insert offset 74 as appropriate. Finally, the outputs 58 can include the patient output information 80 which can include not only the name of the patient but also the shoulder to be treated and other specifics of the guide such as which anatomical landmarks with reference to which the humeral guide 76 is made.

III. Patient Matched Humeral Resection Guides and Methods

This application discloses a number of advantageous patient matched humeral resection guides. These guides can be prepared using the planning system 54 or a similar system. SECTION III(A) discusses guides that can combine patient matched contact points or contact surfaces on a single monolithic body. SECTION III(B) describes a number of embodiments in which the patient matched contact points or surfaces can be disposed on two separate components that can be assembled together during a procedure.

A. Humeral Guides Capable of Monolithic Construction

Figure 4:
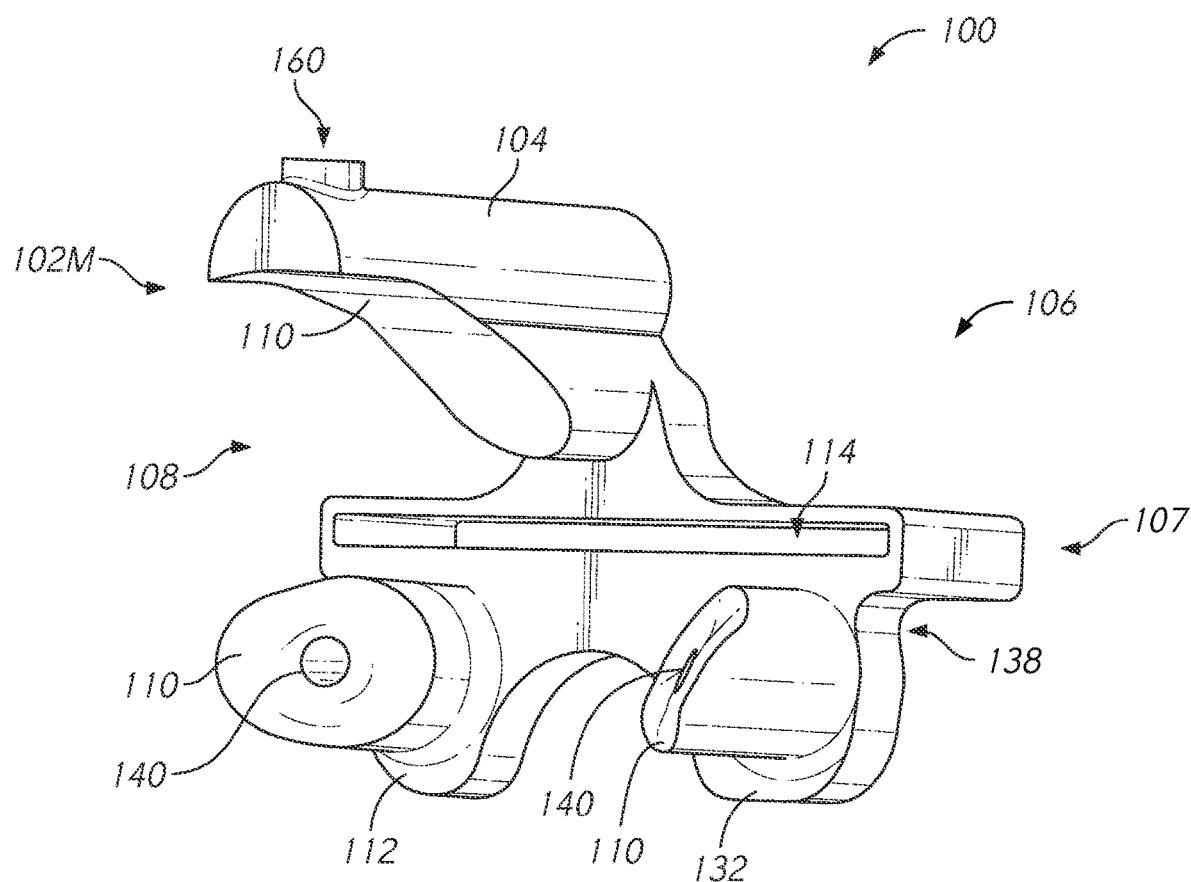
FIG. 4 is a medial side perspective view of a humeral cutting guide.
Figure 5:
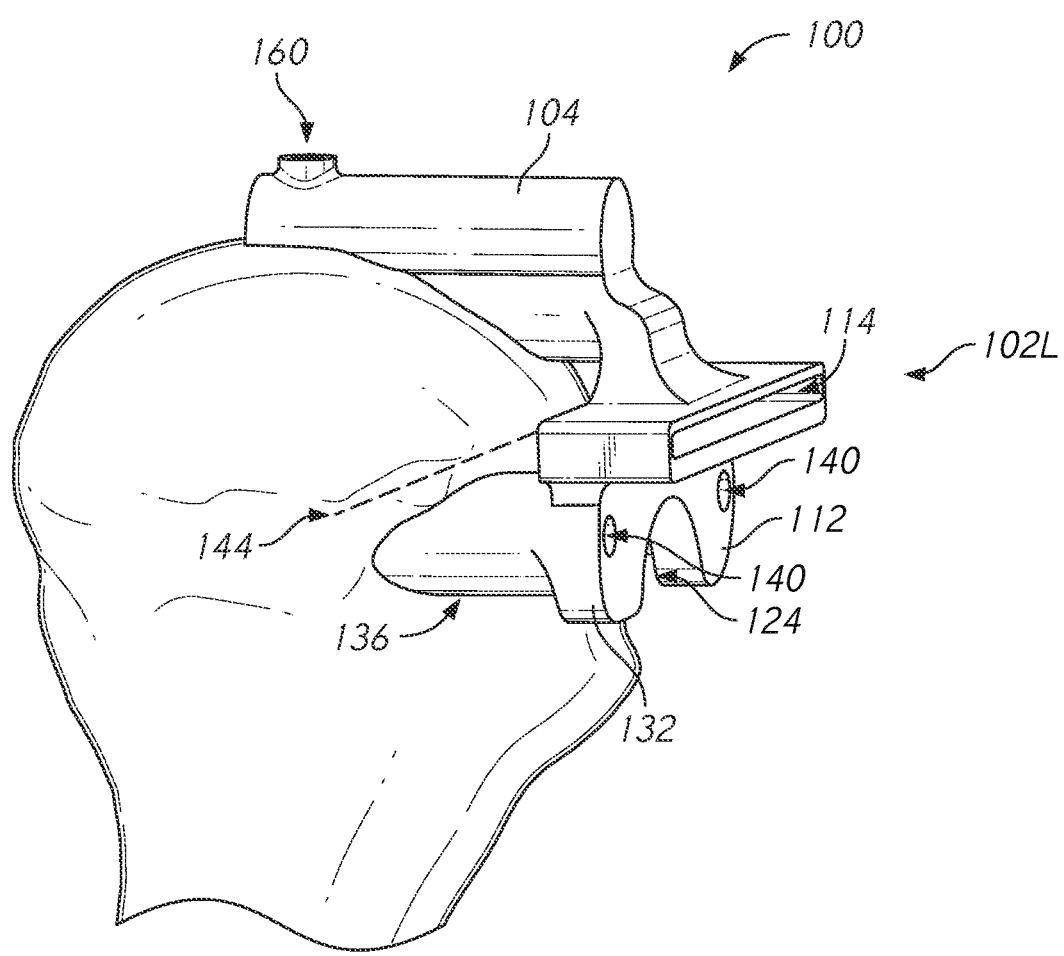
FIG. 5 is a perspective view of a humerus showing a stage of a method of resecting the humerus using the humeral cutting guide of FIG. 4.

FIG. 4 shows a humeral cutting guide 100 which can be one example of the humeral guide 76. The humeral cutting guide 100 includes a first portion 104, a second portion 112, and a third portion 132. Each of the first portion 104, the second portion 112, and the third portion 132 can be configured to contact specific parts of the humerus 12. The humeral cutting guide 100 also includes a lateral side 102L (see FIG. 5) and a medial side 102M.

The humeral cutting guide 100 also includes a first side 106 and a second side 107. The first side 106 of the humeral cutting guide 100 includes the first portion 104. The second side 107 of the humeral cutting guide 100 includes the second portion 112 and the third portion 132. The second side 107 is configured to be placed inferiorly of the first side 106.

The humeral cutting guide 100 can be manufactured to be patient specific by utilizing the planning system 54 or another patient planning system. The humeral cutting guide 100 can thus have one, two or more than two surfaces, e.g., three surfaces, configured to correspond to specific anatomic features of the humerus 12. As discussed above in connection with FIG. 3, the patient specific features can be formed by a process that takes as an input CT images or other similar three dimensional characterization of the bone, processes the images into inputs for a manufacturing process and the produces the features in a three dimensional object such as the guide 100. The manufacturing process can be a conventional molding process and/or can include various additive manufacturing processes. In one embodiment, the proximal portion 108 includes a substantial negative surface 110 that is complementary to a proximal portion of the humerus 12. The proximal portion is a superior portion of the humerus 12 as discussed above. The proximal portion can be the superior end of the humerus. In more detail, the substantial negative surface 110 on the proximal portion 108 can be concave to follow the articular, convex, surface of the head 10 of the humerus 12. As used herein "substantial negative" refers to a surface that is contoured to follow a shape of a specific portion of the humerus. The surface 110 can be configured to follow the convex surface of a head portion of a humerus of a specific patient when the guide 100 is seated on the humerus. The contour of the surface 110 can match that of the bone of the humerus with or without removing of any anatomical structure, e.g., cartilage or osteophytes.

The second portion 112 can be configured to be complementary to a first lateral portion 124 of the humerus 12. The second portion 112 can have a substantial negative surface 110 that can conform to a portion of the humerus 12 distal to the anatomical neck 22 for example. Alternatively, the second portion 112 can include any suitable anatomical landmark of the proximal portion of the humerus 12 that is distal to the head 10 of the humerus 12. The third portion 132 can be configured to be complementary to a second lateral portion 136 of the humerus 12. The third portion 132 can have a substantial negative surface 110 that can conform to a portion of the humerus 12 distal to the anatomical neck 22 for example. Alternatively, the third portion 132 can include a surface complimentary to any suitable anatomic landmark of the proximal portion of the humerus 12 that is distal to the head 10 of the humerus 12. The second portion 112 and the third portion 132 can be complimentary to lateral portions of the humerus 12 distal to the head 10, e.g., on the anatomical neck 22. The second portion 112 and the third portion 132 can be complimentary to lateral portions of the humerus 12 distal to the head 10, e.g., distal of the anatomical neck 22. The second portion 112 and the third portion 132 can be complimentary to the lesser tubercle $T_l$ and the greater tubercle $T_g$ of the humerus 12 respectively. The second portion 112 and the third portion 132 can be complimentary to the bicipital groove BG and the greater tubercle of the humerus 12 respectively. FIG. 2 shows the lesser tubercle $T_l$, the greater tubercle $T_g$, and the bicipital groove BG. The second portion 112 and the third portion 132 can be complimentary to the lesser tubercle and the bicipital groove of the humerus 12 respectively. In each of the foregoing the portions 112, 132 can be reversed for an opposite humerus, e.g., the second portion 112 and the third portion 132 can be complimentary to the greater tubercle and the bicipital groove BG of the humerus 12 respectively. The planning system 54 can include an input to the patient input information 66 indicating whether the cutting guide 100 is being formed for a right or a left humerus.

Preferably the humeral cutting guide 100 includes a monolithic member 138. The monolithic member 138 is configured as a unitary body that includes at least the first portion 104, the second portion 112, and the third portion 132. The humeral cutting guide 100 can includes a continuous structure that extends from the first portion 104 to the second portion 112 and/or to the third portion 132. The humeral cutting guide 100 includes a cutting plane 114 that is disposed through the humeral cutting guide 100 from the lateral side 102L to the medial side 102M. The cutting plane 114 provides access for the saw blade 26 (or other cutting device) through the humeral cutting guide 100 to the humerus 12. The movement of the saw blade 26 through the cutting plane 114 extend into the humerus 12 just distal the head 10 creates a resection plane 144 in the humerus 12 as will be discussed in greater detail below.

The humeral cutting guide 100 also includes one or a plurality of mounting pin apertures 140. A mounting pin aperture 140 is provided through each of the second portion 112 and third portion 132, respectively. The apertures 140 through the second portion 112 and the third portion 132 can extend from the lateral side 102L to the medial side 102M. The mounting pin aperture 140 through the second portion 112 and the mounting pin aperture 140 through the third portion 132 can be oriented at non-parallel orientations to each other. The mounting pin apertures 140 through the second portion 112 and through the third portion 132 can be oriented at parallel orientations to each other.

FIGS. 6 and 7 show that the mounting pin aperture 140 through the second portion 112 can receive a mounting pin 142 therethrough. The third portion 132 can include a mounting pin 142 therethrough. The mounting pins 142 through the mounting pin aperture 140 in the second portion 112 and the mounting pin aperture 140 in the third portion 132 can be oriented when fully inserted such that the ends thereof that are placed in the bone are closer to each other than the ends thereof that are disposed outside the bone when the mounting pins 142 are fully inserted.

In one embodiment, the humeral cutting guide 100 is configure to enable facilitate placement of a guide pin 162 into a proximal portion of the humerus, e.g., into the resected surface 32 of the humerus 12. The first portion 104 can include a guide pin aperture 160 that is disposed therethrough. The guide pin aperture 160 can have an end on the first side 106 of the first portion 104. The guide pin aperture 160 can have a second end on the second side 107 of the first portion 104. The guide pin aperture 160 can have a lumen that is sized to allow the guide pin 162 to slide therethrough into the proximal portion of the humerus 12, e.g., into the resected surface 32.

The cutting plane 114 has the advantage of being enclosed on two opposing sides. More particularly, a portion of the monolithic member 138 on a superior side 106 of the humeral cutting guide 100 is disposed superiorly of the cutting plane 114, which is disposed through the humeral cutting guide 100 from the lateral side 102L to the medial side 102M. A portion of the monolithic member 138 on an inferior side 107 of the humeral cutting guide 100 is disposed inferiorly of the cutting plane 114. By enclosing the cutting plane 114 on the superior side 106 and on the inferior side 107 the humeral cutting guide 100 can reduce a source of error in the movement of the saw blade 26. Specifically, the upper enclosure of the cutting plane 114 on the humeral cutting guide 100 can limit the unintended lifting of the saw blade 26 off of the lower surface bounding the cutting plane 114 on the inferior side 107 thereof.

FIGS. 5 and 6-11 illustrate methods of using the humeral cutting guide 100 to prepare a proximal portion of the humerus 12 to receive a portion of a shoulder implant. The portion of the method illustrated in FIGS. 4 and 6-11 follows other aspects of early phases of methods discussed above, e.g., forming an incision, exposing the humerus, providing access to the lateral side of the humerus, etc.

The humeral cutting guide 100 can be placed on an exposed lateral side of the humerus 12. The medial side 102M can be placed in contact with the humerus 12. The substantial negative surface 110 at the first portion 104 can be placed on top of the head 10 of the humerus 12. The substantial negative surface 110 of the second portion 112 can be placed over the first lateral portion 124 of the humerus 12. The substantial negative surface 110 of the second portion 112 can have, for example, a concave configuration to follow a convex profile of an anatomical landmark at the first lateral portion 124 of the humerus 12. The substantial negative surface 110 of the third portion 132 can be placed over the second lateral portion 136. The substantial negative surface 110 of the third portion 132 can have, for example, a concave configuration to follow a convex profile of an anatomical landmark at the second lateral portion 136 of the humerus 12. The humeral cutting guide 100 can be manipulated until the substantial negative surfaces 110 are nested over the portions of the humerus 12 to which these surfaces were configured to mate.

When so placed, the mounting pins 142 can be placed through the mounting pin aperture 140 disposed through the second portion 112 and the third portion 132. The mounting pin 142 placed through the second portion 112 can be oriented non-perpendicular to the lateral side 102L. The mounting pin 142 placed through the third portion 132 can be oriented non-perpendicular to the lateral side 102L. The mounting pins 142 can be placed through the humeral cutting guide 100 such that they are non-parallel to each other. The ends of the mounting pins 142 disposed in the bone can be disposed closer to each other than are the ends of the mounting pins 142 that are projecting out of (e.g., lateral of) the humerus 12.

FIG. 6 shows the mounting pins 142 disposed through the humeral cutting guide 100 and into the humerus 12. FIG. 6 also shows that the saw blade 26 has already passed through the cutting plane 114 forming a resection plane 144 in the humerus 12. The resection plane 144 can separate the head 10 from the rest of the humerus 12. The head 10 when so resected, can be removed from the rest of the humerus 12 as shown in FIG. 7. The resected head 10 of the humerus 12 can be shifted medially away from the medial side 102M of the humeral cutting guide 100. The first portion 104 is formed so that the substantial negative surface 110 thereof has a highest point at a medial end of the first portion 104. This prevents the first portion 104 from blocking the egress of the head 10 from between the first portion 104 and the resected surface 32. This allows the humeral cutting guide 100 to be left in place as the head 10 is removed from the humerus 12.

Figure 8:
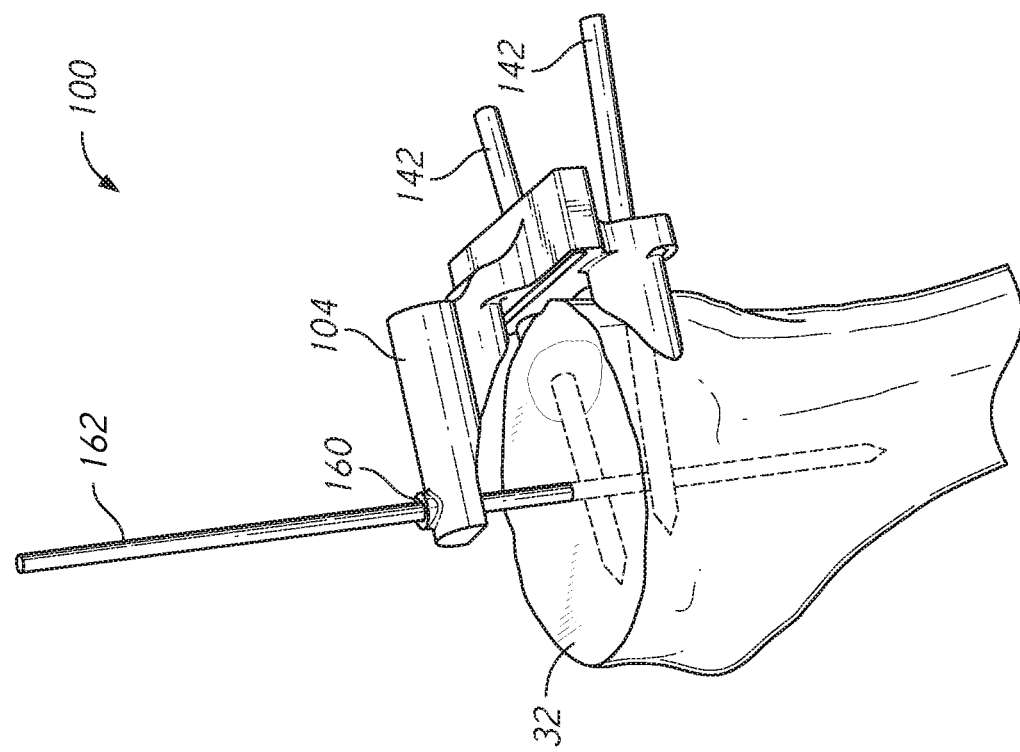
FIG. 8 shows a stage following that of FIG. 7 in which a guide pin is placed through a mounting pin aperture in a portion of the humeral cutting guide of FIG. 4, which portion is disposed over the resected face of the humerus.

FIG. 8 shows that by leaving the humeral cutting guide 100 in place after the head 10 has been removed allows the guide pin 162 to be placed through the guide pin aperture 160. Specifically, a distal end of the guide pin 162 can be advanced into the first side 106 of the guide through the pin aperture 160. The distal end of the guide pin 162 can continue to be advanced through the guide pin aperture 160 and thereafter into the resected surface 32. The guide pin 162 can be directed by the guide pin aperture 160 to a specific position of the resected surface 32 or to a specific position and at a specific orientation relative to the resected surface 32 to enable further preparation of the resected surface 32 to be carried out in a controlled manner as discussed further below. The guide pin 162 can be directed by the guide pin aperture 160 along a patient specific axis. More specifically, the axis 162 can be formed in the guide 100 in a location and along a direction defined by the process of FIG. 3 or a similar process taking patient images as an input and producing a patient specific guide with the axis 162 pre-defined.

Figure 9:
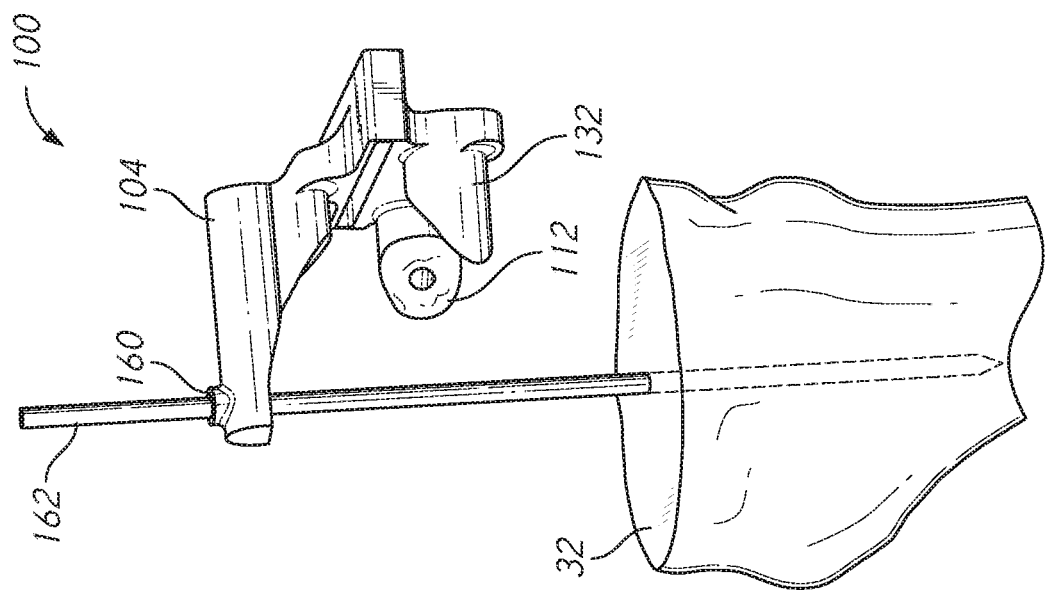
FIG. 9 shows a stage following that of FIG. 8 in which the humeral cutting guide of FIG. 4 is removed along the guide pin which is placed in and can be left in the resected face of the humerus after the humeral cutting guide has been removed.

FIG. 9 shows a further step of a process for preparing a proximal portion of the humerus 12. The humeral cutting guide 100 can be removed from the humerus 12 under the guidance of the guide pin 162. First the mounting pins 142 can be retracted out of the mounting pin apertures 140. Then the humeral cutting guide 100 can be slid along the guide pin 162 away from the resected surface 32. This can control the egress of the humeral cutting guide 100 from the surgical field to keep the progress of the surgical procedure as controlled as possible.

Figure 10:
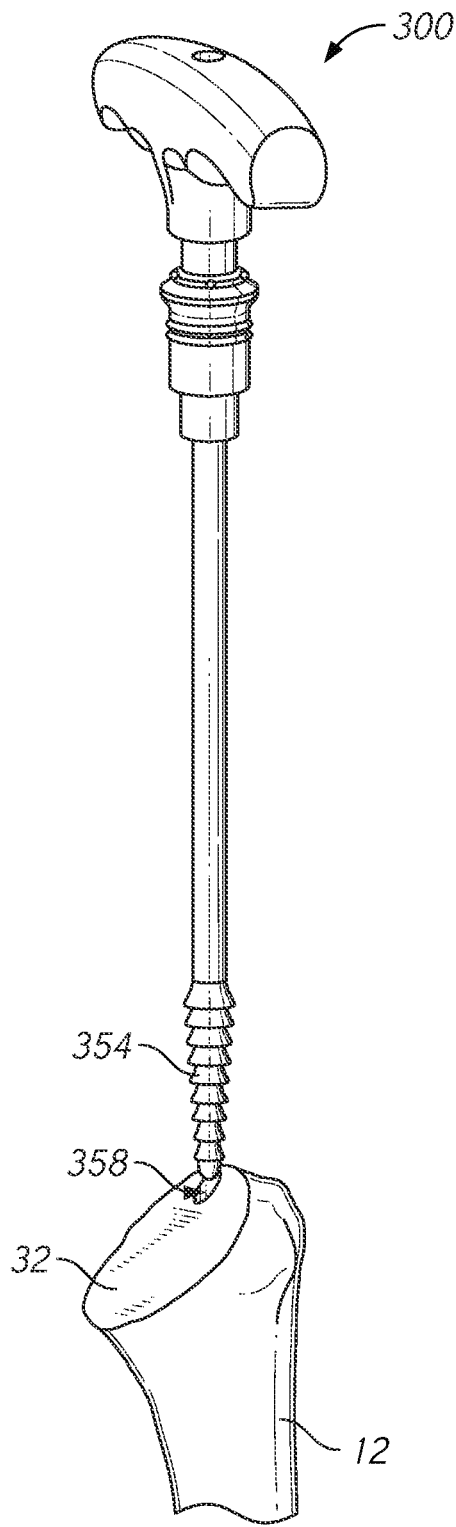
FIG. 10 shows a stage following that of FIG. 9 in which an instrument which can include or be an awl is inserted into a cavity formed with the guide pin.
Figure 11:
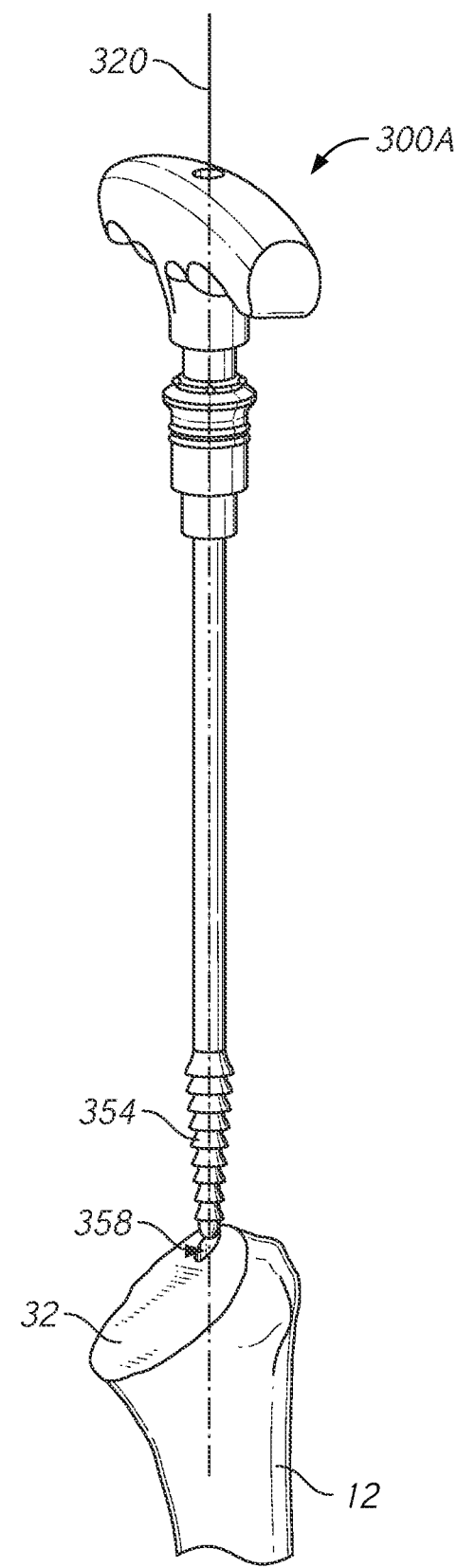
FIG. 11 shows a stage following that of FIG. 9 in which a cannulated instrument is advanced into the cavity over the guide pin which is placed using the humeral cutting guide of FIG. 4.

After the humeral cutting guide 100 has been removed from the free end of the guide pin 162 the process of preparing the resected surface 32 can proceed. FIGS. 10 and 11 illustrate two techniques for further processing the resected surface 32 of the humerus 12. FIG. 10 shows that the guide pin 162 can be removed from the resected surface 32 leaving a cavity 358 formed by a portion of the guide pin 162 that was embedded in the bone extending from the surface 32 toward the distal portion of the humerus 12. The cavity 358 can be disposed at a specific pre-operatively defined position that was one of the outputs 58 of the planning system 54. Specifically, the location of the guide pin aperture 160 on the first portion 104 caused placement of the guide pin 162 through the guide pin aperture 160 to form the cavity 358 in the resected surface 32. After the guide pin 162 is removed, the cavity 358 is left in place and can receive a distal portion of an instrument 300, which can be or can include an awl 354. The awl 354 can be directed along the patient specific axis which was that disposed through the guide pin aperture 160. The awl 354 can be followed by other tools to enlarge and specifically shape a recess in the resected surface 32 that is able to receive a portion of a humeral implant in a controlled manner.

FIG. 11 shows another step of a procedure in which a guide pin 320 is placed into the resected surface 32. The guide pin 320 can be the guide pin 162 as discussed above. In some methods, the guide pin 162 can be exchanged for the guide pin 320 which can be thicker, more rigid, or have other suitable properties for guiding a cannulated instrument 300A to the cavity 358. The cannulated instrument 300A can include a lumen that extends from a first end including a handle portion to a second end including the awl 354. The first end of the cannulated instrument 300A can be advanced over the free end of the guide pin 320 until the awl 354 is at and thereafter enters and forms the cavity 358. The guide pin 320 thus enables the cannulated instrument 300A to be directed along the patient specific axis that was defined through the guide pin aperture 160.

FIGS. 5A and 12-23 illustrate a number of advantageous embodiments each of which can have features that are combinable with the features of the other embodiments herein.

Figure 5A:
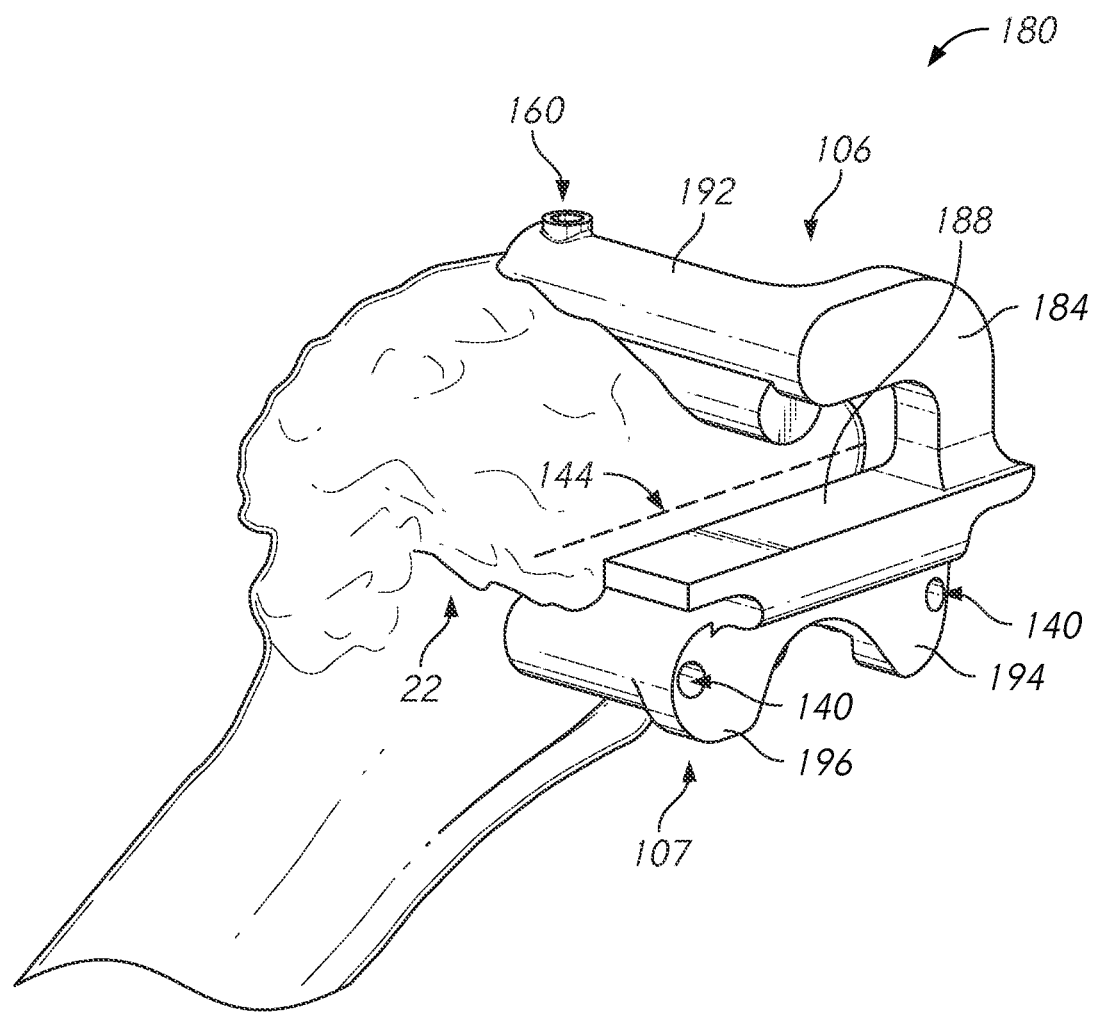
FIG. 5A is a lateral side perspective view of another embodiment of a humeral cutting guide shown mounted to a humerus.

FIG. 5A shows a humeral cutting guide 180 that is similar to the humeral cutting guide 100 except as described differently below. The humeral cutting guide 180 includes an extension member 184 that connects a cutting surface 188 to a first member 192. The cutting surface 188 extends away from one end of the extension member 184. The cutting surface 188 is open to allow the saw blade 26 to be placed directly on top of the surface 188 as the saw blade 26 is moved along the surface 188 toward the humerus 12 to separate the head 10 from the rest of the humerus 12 along the resection plane 144 to form the resected surface 32. When exposed in this manner the saw blade 26 is not prone to binding between close edges on the superior side 106 and inferior side 107 of the humeral cutting guide 180.

The extension member 184 extends from the cutting surface 188 to a first member 192. A distal side of the first member 192 is configured to conform to the proximal portion of the humerus 12. The first member 192 can have a patient specific, e.g., a complementary surface similar to the first portion 104 of the guide 100. The extension member 184 can form a bight together with the cutting surface 188 with a top portion of the extension member 184 extending over generally parallel to the cutting surface 188. FIG. 5A shows the extension member 184 disposed on a lateral side of the guide 180 (generally to the right in FIG. 5A). In another embodiment, the extension member 184 is disposed on a medial side of the guide 180 (generally to the left in FIG. 5A). A medial placement is advantageous in that when applied to the humerus as in FIG. 5A, there is more soft tissue on the lateral side of the guide 180. A medial location for the extension member 184, away from the soft tissue, provides a better view on the humeral head during the procedure. A gap between the top portion and the cutting surface 188 is much larger than the width of the saw blade 26. In contrast in the humeral cutting guide 100 the gap between the structures forming the cutting plane 114 is much smaller. The gap between the structures forming the cutting plane 114 in the humeral cutting guide 100 is close to the thickness of the saw blade 26 such that the blade may bind in the cutting plane 114.

The humeral cutting guide 180 includes a second member 194 and a third member 196. The second member 194 and the third member 196 can be analogous to the second portion 112 and the third portion 132 of the humeral cutting guide 100, providing similar function. Each of the second member 194 and the third member 196 has a medial side configured to conform to specific portions of the humerus distal the resection plane 144, e.g., adjacent to but distal the anatomical neck 22 of the humerus and conforming to an anatomical landmark in some implementations. The second and third members 194, 196 can each have a patient specific, e.g., a complementary surface similar to the second and third portions 112, 132 of the guide 100. As in the guide 100, medial ends and/or medial surfaces of the portions 192, 194, 196 are configured to be patient specific. As above-described, pre-operative scans can be utilized to configure patient specific surfaces to be complementary, e.g., negative, surfaces of the bone to which they are to mate such that the implant is seated according to the optimized fit as determined by the surgeon.

The second member 194 and the third member 196 can each have a mounting pin aperture 140 disposed therethrough. The mounting pins 142 can be advanced through the mounting pin apertures 140 and the rest of the methods described above can follow. A point of difference is that the saw blade 26 can be placed in the large area between the top portion of the extension member 184 and the cutting surface 188. This area is much larger than the width of the saw blade 26. The cutting plane 114 of the guide 100 is able to provide more control because the top and bottom surfaces of the blade 26 are both guided in a narrow slot defining the cutting plane 114. This guidance helps to reduce or eliminate diving or lifting of the saw blade 26. . Reducing or eliminating diving and/or lifting results in a more consistently precise resection of the humerus in the use of the guide 100. The enhanced consistency may mean that the guide 100 can facilitate a shorter procedure if all other variables are equal because less time and effort would be needed to assure that the saw blade 26 follows the intended trajectory rather than diving or lifting. Shortening the process for preparing the humerus 12 is valuable because a shoulder replacement procedure has many other steps and any configuration that shortens procedure time is of value. On the other hand, the guide 180 is simpler to manufacture. Also, the relatively large flat cutting surface 188 can provide better visibility to the surface of the humerus and thus provides the surgeon with more information from direct visualization during the procedure.

The cutting guide 180 also can be configured with the pin apertures 140 directly below the cutting surface 188. By placing the pin apertures 140 directly below the cutting plane, elongate pins can be placed through the apertures 140 and can be used to guide the lower side of the blade 26 to reduce or eliminate diving or lifting. The bottom side of the blade 26 can move across top portions of the pins disposed through the apertures 140 as the blade moves from medial to lateral (or lateral to medial) along the cutting surface 188. The top portions of the pins thus prevent excessive diving of the distal or working end of the blade 26. Free ends of the pins disposed through the apertures 140 could also or alternatively be used to guide the blade 26 indirectly. For example the saw to which the blade 26 is coupled could be guided by an exposed length of the pins disposed through the apertures 140 to reduce or eliminate lifting of the working end of the blade 26.

B. Patient Specific Humeral Guides with Patient Independent Cutting Guides

Figure 12:
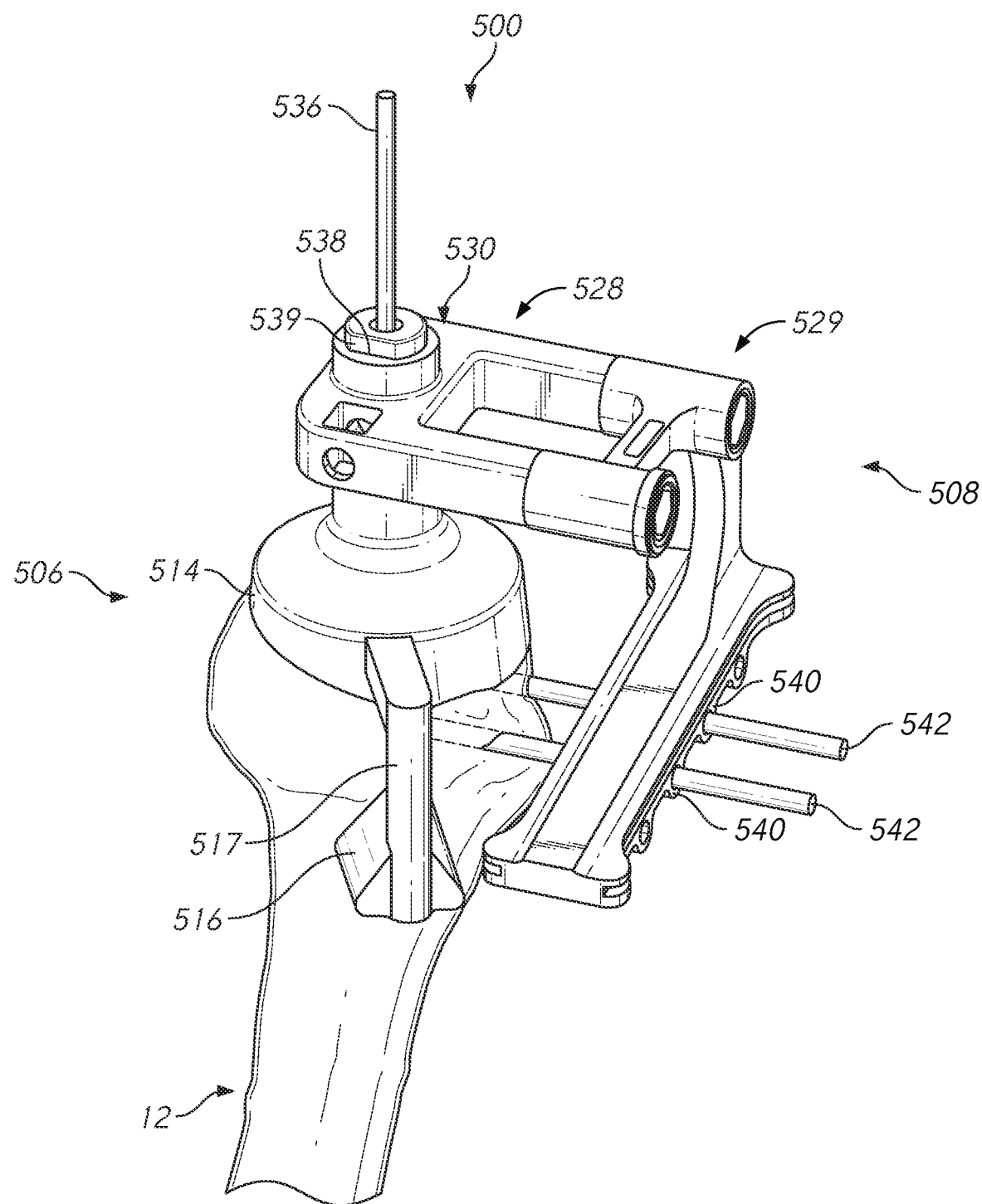
FIG. 12 is a cutting guide system coupled to the humerus prior to the resection thereof.
Figure 12A:
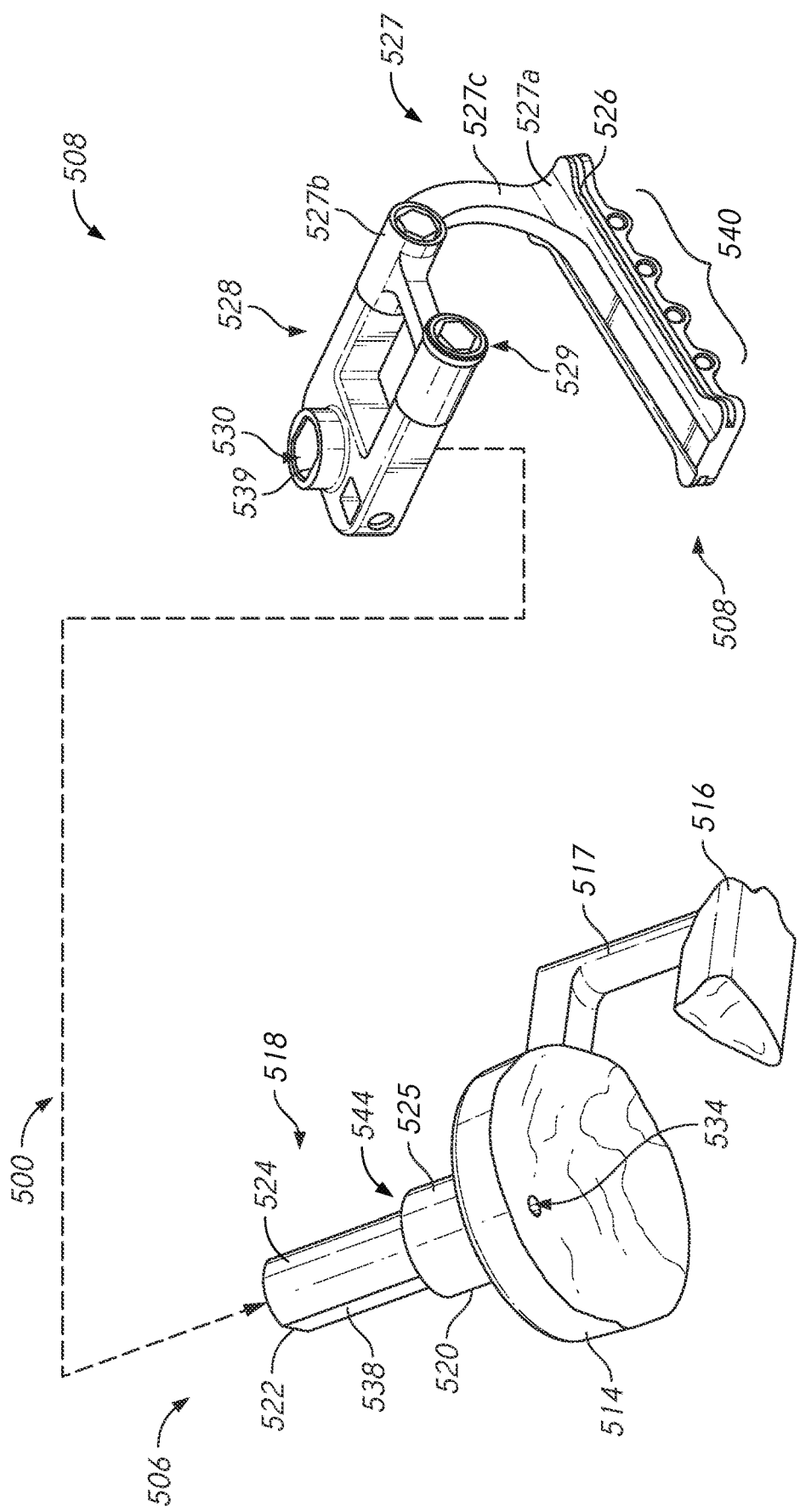
FIG. 12A is an exploded view of the cutting guide system of FIG. 12.

FIGS. 12 and 12A show a cutting guide system 500 that is able to employ a patient specific portion and a standard cutting component. The cutting component can be made of a more durable material that allows it to be refurbished for subsequent patients. The patient specific portion can be formed using the process of FIG. 3 or a variant thereof and can be discarded as it has only one patient shoulder to which it would be properly fitted. The cutting guide system 500 includes a guide body 506 and a cutting guide 508. The guide body 506 is the patient specific portion. The cutting guide 508 is not patient specific but rather is useable across a population of patients.

The guide body 506 includes a concave member 514 and a side member 516. The concave member 514 is connected to the side member 516 by an extension member 517. The extension member 517 extends from an edge of the side member 516 to an edge of the concave member 514. The side member 516 is located at a distal end of the guide body 506. The extension member 517 extends away from the edges of the side member 516 and the concave member 514 by a sufficient amount to avoid contact with the proximal portion of the humerus 12. One or both of the concave member 514 and the side member 516 is configured to conform to a specific portion of a specific humerus of a specific patient. The side member 516 can be configured to engage a side portion, e.g., a lateral side portion of the humerus at a convenient location such as at an anatomical neck 22 or another anatomical landmark adjacent to the anatomical neck 22. The side member 516 can be a neck member. That is the side member 516 can be configured to engage the humerus at or adjacent to, e.g., just distal to the anatomic neck 22 in a patient specific manner, e.g., having a complementary surface that can be formed as a substantial negative of the humerus at or adjacent to, e.g., just distal to the anatomic neck 22. The concave member 514 and the side member 516 can each have a patient specific, e.g., a complementary, surface similar to the first portion 104 and one or both of the second and third portions 112, 132 of the guide 100. As in the guide 100, bone facing ends or surfaces of the portions 514, 516 are configured to be patient specific. These ends or surfaces can be concave to mate with convex bone profiles of the proximal portion of the humerus 12. As above-described, pre-operative scans can be utilized to configure patient specific surfaces to be complementary, e.g., negative, surfaces of the bone to which they are to mate such that the implant is seated according to the optimized fit as determined by the surgeon.

A projection 518 of the guide body 506 is disposed away from the bone contacting side of the concave member 514. The projection 518 has a first end 520 and a second end 522. The projection 518 has an elongate body between the first end 520 and the second end 522. A first portion 524 extends from the second end 522 of the proximal projection 518. A second portion 525 extends from an end of the first portion 524 to the first end 520. The first portion 524 is longer than the second portion 525 in one embodiment. In one embodiment the first portion 524 is two, three, or four times longer than the second portion 525. A shoulder 544 can be provided between the first portion 524 and the second portion 525. The shoulder 544 provides a locator or position control device for the cutting guide 508.

In one embodiment, the guide body 506 includes a guide pin aperture 534 disposed therethrough. A bone facing end of the aperture 534 is located on a patient specific surface of the concave member 514. The guide pin aperture 534 can be centered on the patient specific surface of the concave member 514. The guide pin aperture 534 can extend from the patient specific surface to the proximal projection 518 to the second end 522 of the projection 518. The guide pin aperture 534 can extend through the proximal projection 518. The aperture 534 can be sized to slideably receive the first mounting pin aperture 164 discussed above. The guide pin aperture 534 can be considered to extend to the proximal end of the proximal projection 518 providing access for a flat edge guide pin 536 as discussed further below.

The cutting guide 508 can include a cutting plane 526 formed on a cutting plane body 527. The cutting plane body 527 can be coupled with a coupler 528. In one embodiment, the coupler 528 is releaseably coupled with the cutting plane body 527 at a joint 529. The joint 529 allows the proximal/distal position of the cutting plane 526 to be adjusted. For example, the cutting plane body 527 can include a first portion 527a having the cutting plane 526 formed therein. The cutting plane body 527 can include a second portion 527b configured to be disposed at the same proximal distal location as the coupler 528. The cutting plane body 527 can have an axial body 527c disposed along a proximal-distal axis or direction connecting the first and second portions of the cutting plane body 527 to each other. The cutting plane body 527 can form a bight between the second portion 527b, the axial body 527c, and the first portion 527a thereof. In the illustrated embodiment, the first portion 527a of the cutting plane body 527 is configured to be disposed on both sides of the cutting plane 526 such that when the saw blade 26 is inserted into the cutting plane 526 the cutting plane body 527 is disposed directly over both opposing sides of the saw blade 26. The cutting plane body 527 could be configured such that a structure is disposed on only a distal side or a proximal side of the cutting plane 526. For example, the axial body 527c of the distal body 527 can be directly coupled with a distal portion of the cutting plane body 527 that extends below (e.g., distal of when applied to the humerus) the cutting plane 526. In such embodiment, the distal portion is only distal of and is not proximal of the cutting plane 526 at least in the portion of the cutting plane 526 along which the resection of the humerus 12 is made.

In one embodiment the first portion 527a of the cutting plane body 527 comprises one or a plurality of, e.g., four, mounting pin apertures 540. Each of the mounting pin apertures 540 is configured to receive a corresponding mounting pin 542. The mounting pins 542 when disposed through the mounting pin apertures 540 can also be disposed into the lateral faces of the humerus 12 as shown in FIG. 12. Providing more than two mounting pin apertures 540 allows for intra-operative selection of the best locations to advance the mounting pins 542 into the humerus 12.

The coupler 528 can include an aperture 530 as noted above. In one embodiment, the coupler 528 is configured to slide over the projection 518 of the guide body 506 to couple the cutting guide 508 with the guide body 506. The coupling between the coupler 528 and the projection 518 can be one that resists relative rotation between the cutting guide 508 and the guide body 506. In one embodiment, one or more flats of the aperture 530 can mate with one or more flats of the projection 518. FIGS. 12 and 12A show that the projection 518 can have a flat edge 538 and the aperture 530 also can have a flat edge 539 that corresponds to the flat edge 538. To couple the cutting guide 508 with the guide body 506 the flat edges 538, 539 are rotationally aligned. The body 528 and the concave member 514 can be moved toward each other until the projection 518 is received in the aperture 530. Further relative movement toward each other can proceed until a distal face of the coupler 528 is contacting the shoulder 544. Such contact corresponds to the position shown in FIG. 12.

The combination of the guide body 506 and the cutting guide 508 enable the cutting guide system 500 to provide a patient specific resection 36 of the humerus 12. For example, the concave member 514 and the distal member 516 can be configured to mate with the humerus 12 in only one position on the humerus. When so positioned, the guide pin aperture 534 can be centered on a patient specific proximal-distal axis that provides guidance to post resection preparation of the humerus 12 at the resected surface 32. Also, the proximal distal location of the shoulder 544 and the configuration of the axial member 527c cause the cutting plane 526 to be at a pre-defined patient specific proximal distal location. These are some of the examples of how the cutting guide system 500 can provide patient specific preparation of the humerus 12. The concave member 514 can conform to, e.g. be a negative of, the convex shape of the head 10 of the humerus 12. The distal member 516 can be configured to mate with any predefined anatomical landmark, including any of those discussed above.

A method of using the cutting guide system 500 can be as follows. The humerus 12 is exposed in the manner discussed above, e.g., by forming an incision and separating the head 10 of the humerus 12 from the scapula 14. The guide body 506 can then be placed over the head 10 of the humerus 12. The side member 516 can then be aligned with and mated to an anatomical landmark on a portion of the humerus 12 distal the head 10, e.g., on a lateral portion or side of the humerus 12 distal the anatomical neck 22. The coupler 528 can be placed at the free end of the projection 518 and the flat edges 538, 539 can be rotationally aligned. Thereafter, the aperture 530 can be advanced over the proximal projection 518 until the distal side of the coupler 528 is contacting the shoulder 544. Thereafter one or more mounting pins 542 can be advanced through one or more mounting pin apertures 540 into an adjacent portion of the humerus 12. Thereafter, the guide pin 536 can be advanced through the guide pin aperture 534 into the head 10 of the humerus 12. The guide pin 536 is preferably not advanced to or distal to the cutting plane 526 to avoid interference with the saw blade 26 as the resected surface 32 is being formed. After the resected surface 32 is formed, the guide pin 536 can be advanced into the resected surface 32 to aid in subsequent preparation of the humerus 12 at the resected surface 32. In one variation, the guide pin 536 is inserted distal of the cutting plane 526 and then retracted, e.g., entirely out of the proximal projection 518. The resected surface 32 is then formed. A channel formed by the guide pin 536 will be accessible once the head 10 is removed from the resected surface 32. The instrument 300 can then be used at the channel. Or the guide pin 536 or the guide pin 320 can then be advanced into the channel formed by the guide pin 536 prior to resection after the cutting guide system 500 has been removed from the humerus 12.

Further methods including those discussed above can be carried out to further prepare the resected surface 32 of the humerus 12 to receive a humeral implant.

C. Patient Specific Humeral Guides with Distal Contact Points

Figure 13:
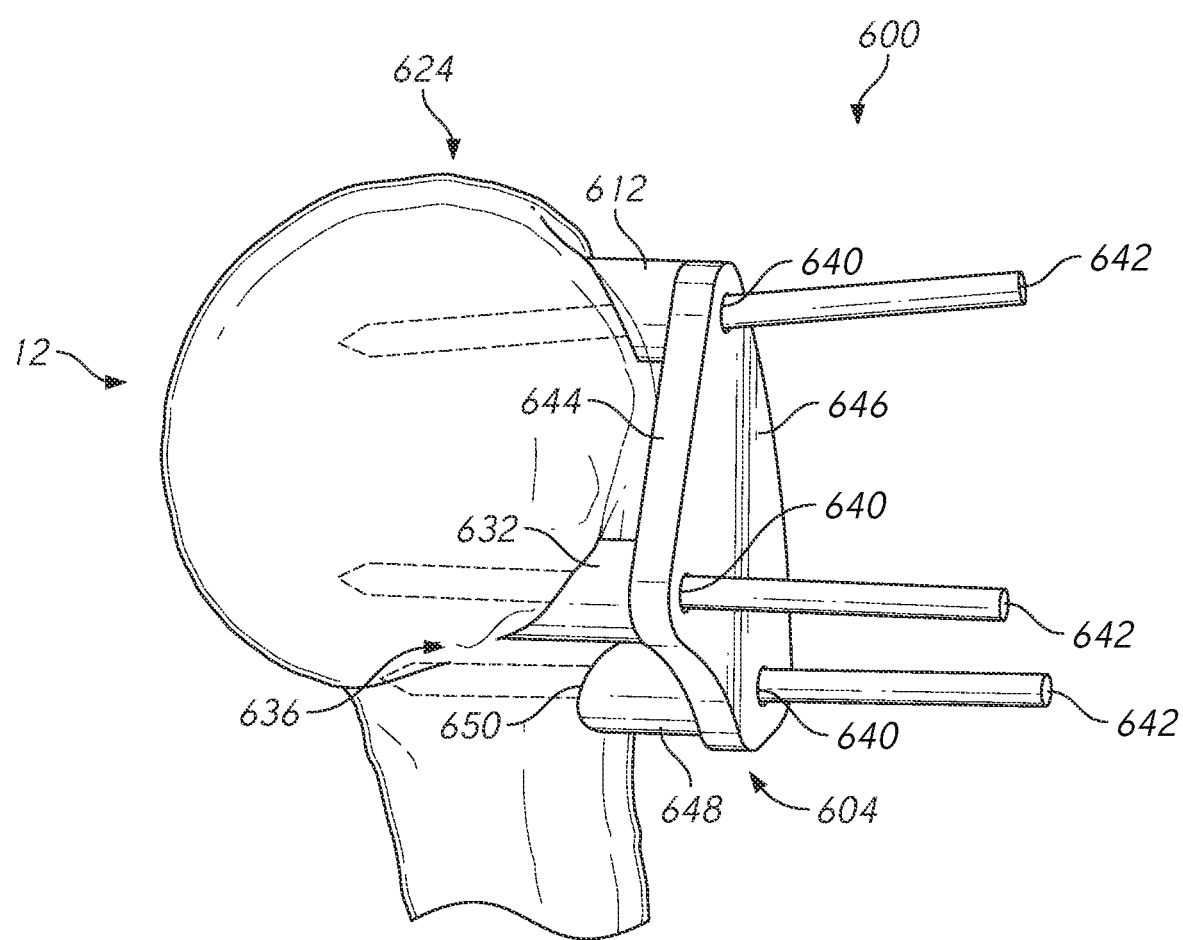
FIG. 13 is a proximal lateral view of another embodiment of a humeral cutting guide coupled with a humerus.

FIG. 13 shows a humeral cutting guide 600 which is another embodiment of a cutting guide that can employ patient specific features. The humeral cutting guide 600 includes a first portion 604, a second portion 612, and a third portion 632. The first portion 604 is configured to be patient specific, e.g., complementary to a portion of the humerus 12. The first potion 604 can have a patient specific, e.g., a complementary surface similar to the first portion 104 of the guide 100. As in the guide 100, medial ends and/or medial surfaces of the first portion 604 can be configured to be patient specific, such as having concave contours that can nest over or at least partially surround convex bone portions that are identified in pre-operative imaging. The above-described pre-operative scans can be utilized to configure patient specific surfaces to be complementary, e.g., negative, surfaces of the bone to which they are to mate such that the implant is seated according to the optimized fit as determined by the surgeon. FIG. 13 shows that the portion of the humerus 12 to which the first portion 604 can be complementary can be a portion distal to the anatomical neck 22. The first portion 604 can be complementary to the surgical neck of the humerus 12 or to another landmark located distally to the anatomical neck 22, distally to the greater and/or the lesser tubercle, distally to the bicipital groove.

The second portion 612 of the humeral cutting guide 600 can be configured to be complementary to a first lateral portion 624 of the humerus 12. The third portion 632 of the humeral cutting guide 600 can be configured to be complementary to a second lateral portion 636 of the humerus 12. The first lateral portion 624 and the second lateral portion 636 can be any of the landmarks discussed above and/or can include one or more osteophytes. The first lateral portion 624 of the humerus 12 and the second lateral portion 636 of the humerus 12 can be anatomical structures disposed distally of the anatomical neck 22.

The humeral cutting guide 600 includes a plurality of mounting pin apertures 640. The mounting pin apertures 640 preferably are formed through two or more of the first portion 604, the second portion 612, and the third portion 632 of the humeral cutting guide 600. The mounting pin apertures 640 are each preferably configured to slideably receive a corresponding plurality of mounting pins 642. A mounting pin 642 can be advanced through each mounting pin aperture 640 and further advanced into the lateral face of the humerus 12. The mounting pin apertures 640 and the mounting pins 642 can be disposed along non-parallel directions to help secure the humeral cutting guide 600 to the humerus 12.

In one embodiment, at least one of, e.g., all of, the first portion 604, second portion 612, and third portion 632 comprise a projection 648 that extends from a plate member 646 of the humeral cutting guide 600. FIG. 13 shows that the first portion 604 can include the projection 648 that extends form a medial side of the plate member 646 toward the humerus 12 in use. A medial end of the projection 648 comprises a bone contacting end 650. The bone contacting end 650 can be configured to be complementary, e.g., to be a substantial negative of a bone portion distal the anatomical neck 22 as discussed above. Each of the second portion 612 and the third portion 632 also includes a projection 648 and a bone contacting end 650 in one embodiment. The bone contacting ends 650 of the portions 604, 612, 632 can each have a patient specific, e.g., a complementary surface similar to that of the second and third portions 112, 132 of the guide 100. As above described, pre-operative scans can be utilized to configure the end 650 to be complementary, e.g., negative, surfaces of the bone to which they are to mate such that the implant is seated according to the optimized fit as determined by the surgeon.

The humeral cutting guide 600 also includes a cutting plane 644 disposed along one surface thereof. FIG. 13 shows that the cutting plane 644 can be disposed along the surface of the plate member 646 that faces proximally when the guide 600 is applied to the proximal portion of the humerus 12. The cutting plane 644 can be a smooth exposed plane that the saw blade 26 (or other cutting apparatus) can rest on and advance across. The cutting plane 644 advantageously is exposed so that the saw blade 26 will not bind to the humeral cutting guide 600 as it is inserted into the humerus 12 and reciprocated back and forth over the humeral cutting guide 600. The humeral cutting guide 600 provides the advantage of enabling patient specific contact with the humerus 12 without any portion thereof being disposed over the proximal end of the humerus 12, e.g., over the head 10. This allows the resected head 10 to be removed in any direction.

In one modified embodiment, the contact pattern of the first portion 604, second portion 612, and third portion 632 of the humeral cutting guide 600 is combined with a pin guide structure as in the humeral cutting guide 100 and the cutting guide system 500. The pin guide structure in the modified embodiment can be on a projection that is spaced apart from and does not make patient specific contact with the head 10. The pin guide structure can include a pin guide aperture that is located and/or oriented to form a channel in the head 10 or in the resected surface 32 that is at a pre-defined patient specific location to aid in preparation of the resected surface 32. The pin guide structure can extend from an end of the cutting plane 644 to a position proximal thereof, with a structure similar to the extension member 184 or the axial member 527c discussed above.

Figure 14:
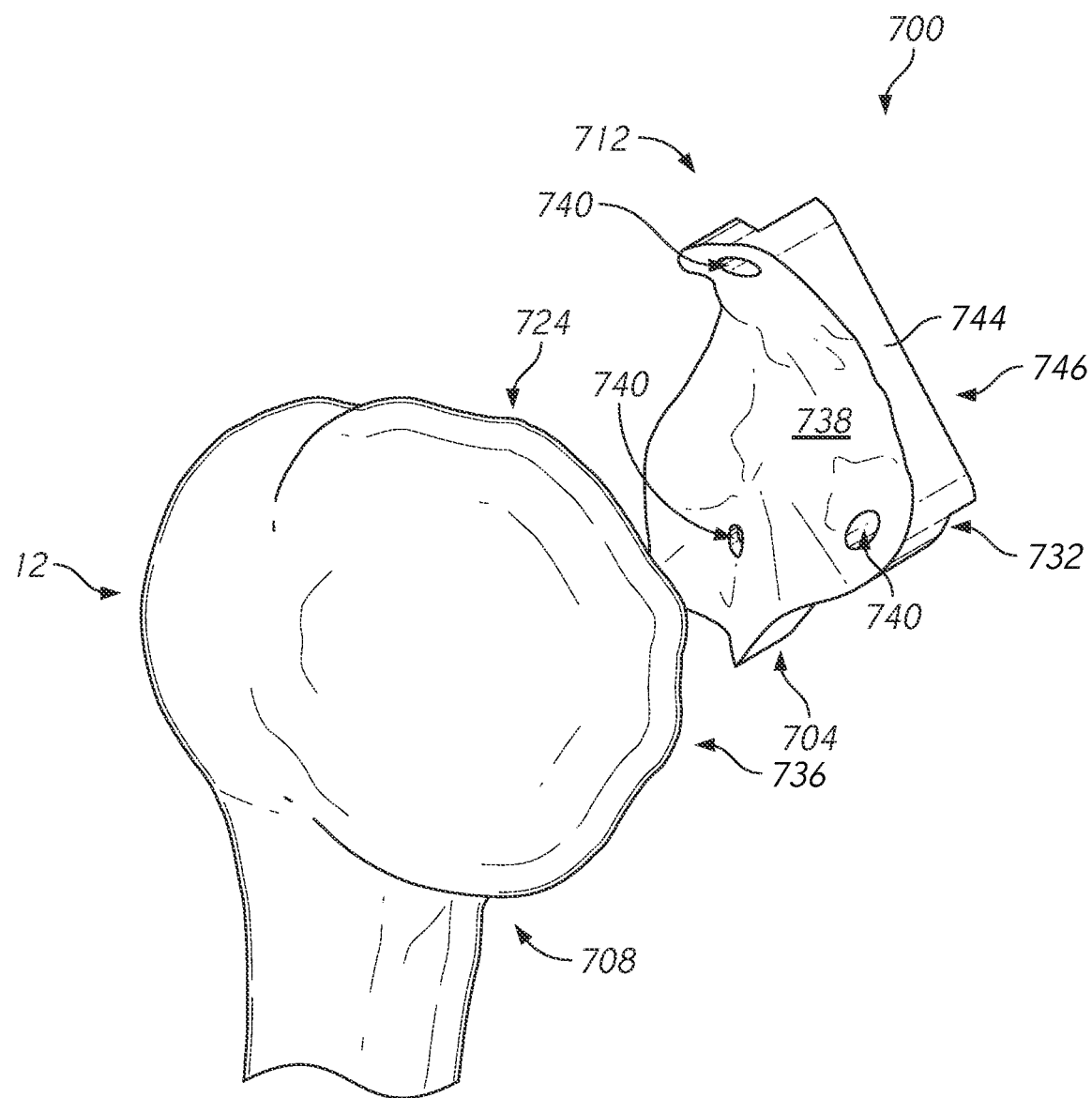
FIG. 14 is a proximal medial view of another embodiment of a humeral cutting guide being coupled with a humerus.

FIG. 14 shows a humeral cutting guide 700 which is another embodiment of a cutting guide that can employ patient specific features. The humeral cutting guide 700 can be similar to the humeral cutting guide 600 except as described differently below. The humeral cutting guide 700 includes a first portion 704, a second portion 712, and a third portion 732. At least two and preferably three of the first portion 704, the second portion 712, and the third portion 732 are configured to be complementary to, e.g., substantial negatives of corresponding bone portions, e.g., to a first portion 708, to a first lateral portion 724, and to a second lateral portion 736 of a humerus 12. For example, the first portion 704 can include a surface that is concave, the shape of the concavity corresponding to or matching so as to optimally fit over a corresponding convex portion of the bone at the first portion 708 of the humerus 12. The second portion 712 can also have a concave surface. The shape of the concave surface of the second portion 712 can be configured to optimally fit over a corresponding convex portion of the bone at the first lateral portion 724 of the humerus 12. The shape of the concave surface of the third portion 732 can be configured to optimally fit over a corresponding convex portion of the bone at the second lateral portion 736. Because the proximal portion of the humerus 12 has irregular shapes among its regions, the concavities of the first, second and third portions 704, 712, 732 can be all different from each other while providing optimal fit to the portions 708, 724, 736 of the humerus 12. As above described, pre-operative scans can be utilized to configure the first, second and third portions 704, 712, 732 to be complementary, e.g., negative, surfaces of the bone to which they are to mate such that the implant is seated according to the optimized fit as determined by the surgeon. The first portion of a humerus 708 can be disposed distal to both the first lateral portion 724 and the third portion 732. The first portion 704 can be complementary to at least a portion of the surgical neck 708 of the humerus 12.

The humeral cutting guide 700 preferably includes a monolithic member. In other words, the first portion 704, second portion 712, and the third portion 732 can all be formed as one unitary part that can be fitted over the proximal portion of the humerus 12. The humeral cutting guide 700 can comprise a plate member 746. The plate member 746 can be non-patient specific on one side, e.g., planar on one side and can be patient specific on the other side. The patient specific side can extend continuously in a patient specific manner from at least one of the first portion 704, second portion 712, and third portion 732 to at least one other of the first portion 704, second portion 712, and third portion 732. Thus the humeral cutting guide 700 can include a continuous bone contacting surface 738, which can comprise at least a portion of the medial side of the humeral cutting guide 700. Said another way, a patient specific contour can extend over and between the portions 704, 712, 732, which contour can be a complementary surface, similar to but much larger than that of the second surfaces 110 of the portion 104, 112, 132 of the guide 100. As in the guide 100, the patient contacting surface of the guide 700 is configured to be patient specific. As above-described, pre-operative scans can be utilized to configure patient specific surfaces to be complementary, e.g., negative, surfaces of the bone to which they are to mate such that the implant is seated according to the optimized fit as determined by the surgeon.

The humeral cutting guide 700 can include mounting pin apertures 740. The mounting pin apertures 740 can be disposed through the first portion 704, the second portion 712, and the third portion 732. The mounting pin apertures 740 can include three mounting pin apertures 740. Two mounting pin apertures 740 can be configured to be disposed adjacent to, e.g., just distal to the anatomical neck 22. One of the mounting pin apertures 740 can be configured to be disposed adjacent to the surgical neck or another anatomical landmark distal to the anatomical neck 22.

Preferably the humeral cutting guide 700 includes a cutting plane 744. The cutting plane 744 can be exposed along one edge of the humeral cutting guide 700. For example, the cutting plane 744 can be disposed on a proximal edge of the humeral cutting guide 700. The cutting plane 744 provides at least the same advantages as the cutting plane 744 discussed above, for example being exposed to allow the saw blade 26 to move thereover into the humerus 12 without binding to close edges as discussed above.

In one modified embodiment, the contact pattern of the humeral cutting guide 700 is combined with a pin guide structure as in the humeral cutting guide 100 and the cutting guide system 500. The pin guide structure in the modified embodiment can be on a projection that is spaced apart from and does not make patient specific contact with the head 10. The pin guide structure can include a pin guide aperture that is located and/or oriented to form a channel in the head 10 or in the resected surface 32 that is at a pre-defined patient specific location to aid in preparation of the resected surface 32. The pin guide structure can extend form an end of the cutting plane 744 to a position over the resected surface 32, with a structure similar to the extension member 184 or the axial member 527c discussed above.

Methods of using the humeral cutting guide 600 and the humeral cutting guide 700 can include placing the medial side of the humeral cutting guide 600 or the humeral cutting guide 700 again an exposed surface of the humerus 12. The placement of the humeral cutting guide 600 and the humeral cutting guide 700 can be patient specific. For example, the patient specific medial ends or surfaces of the guides 600, 700 can be moved into the surgical field. The medial ends can be placed onto exposed bone surface on a lateral side of the bone. The lateral portion of the humerus 12 to which the guides 600, 700 contact can have landmarks or contours which are noted and accounted for in the process discussed above in connection with FIG. 3. The guides 600 or 700 are configured to have complementary shapes to these landmarks or contours. As such the guides 600, 700 properly rest in only one position over the humerus 12. For example, the bone contacting end 650 of the projections 648 can be moved to be positioned over the landmarks to which they were formed to be complementary, e.g., to be substantial negatives. The continuous bone contacting surface 738 of the humeral cutting guide 700 can be moved to be positioned over the region of the humerus 12 to which it was formed to be complementary, e.g., to be a substantial negative. Thereafter mounting pins 642 can be advanced through the mounting pin apertures 640 or the mounting pin apertures 740. Thereafter the saw blade 26 can be moved over the cutting plane 644 or the cutting plane 744 to detach the head 10 from the rest of the humerus 12. The cut can be made at, adjacent to or just proximal of the anatomical neck 22. Thereafter the humeral cutting guide 600 or the humeral cutting guide 700 can be removed from the humerus 12 leaving the resected surface 32 exposed for further preparation if called for. Alternative, if the modified embodiments are employed such that a pin guide is placed into the head 10 to form a bone channel or cavity at the resected surface 32 as discussed above the further preparation of the resected surface 32 can be with reference to the bone channel or cavity. As examples, the instrument 300 can be used to access the bone channel or cavity as discussed above. Or the cannulated instrument 300A can be advanced over the mounting pins 304 into the channel or cavity as discussed above.

After the resected surface 32 is fully prepared a humeral stem or other anchor can be placed into or embedded in the cancellous bone beneath the resected surface 32. After the stem or stemless anchor is placed an anatomic or reverse style articular body can be attached thereto.

D. Patient Specific Humeral Guides Spanning Muscular Insertion Sites

Figure 16:
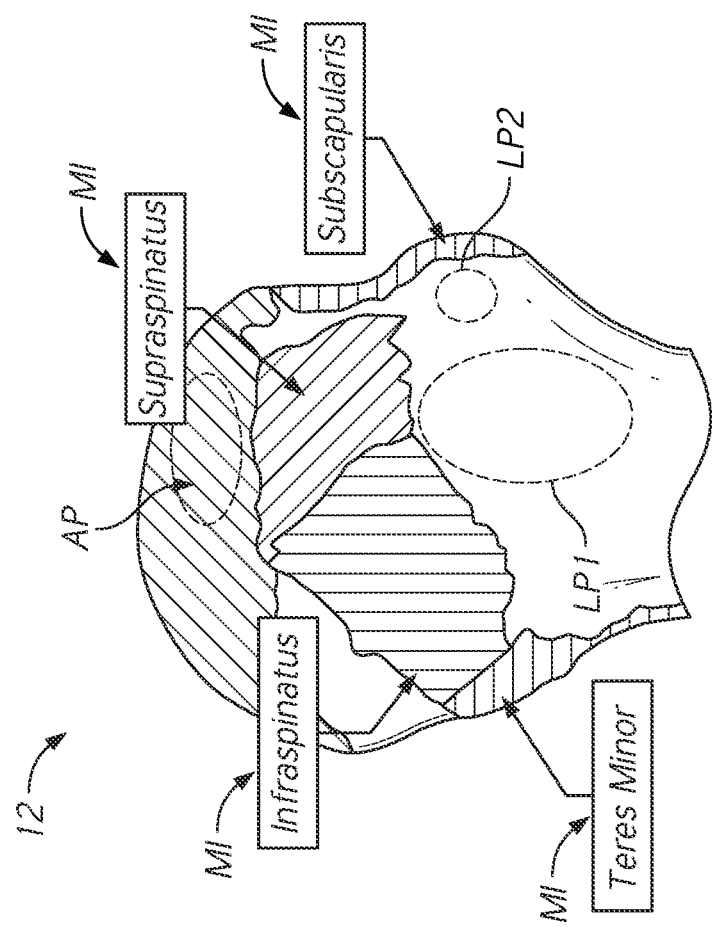
FIGS. 15-16 are lateral views of the proximal humerus identifying relevant anatomic locations.
Figure 15:
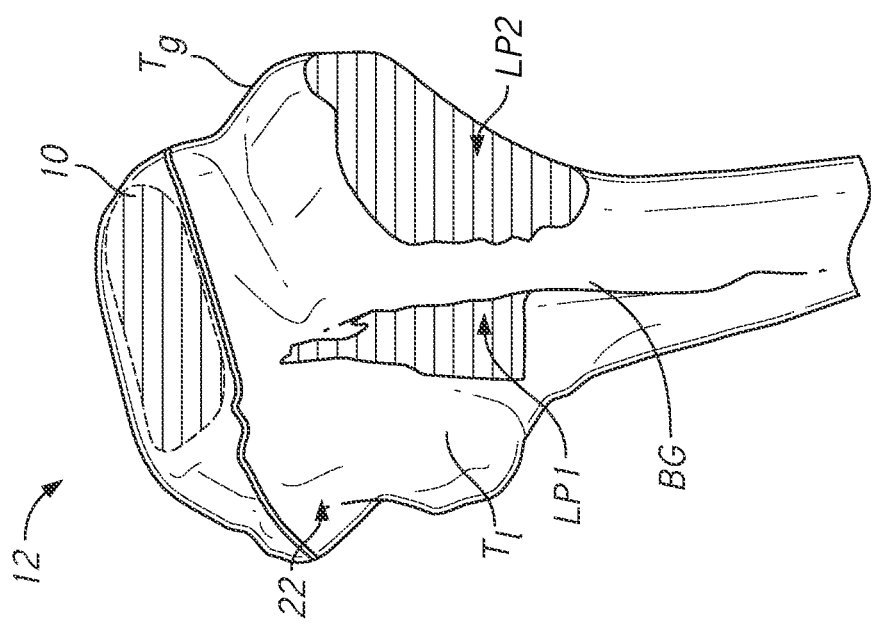

The foregoing embodiments describe humeral guides with patient specific contact points and surfaces. FIGS. 15-16 shows that it is also advantageous to consider as part of the design of a guide the location of various muscular insertion sites MI. FIG. 15 shows that the head 10 of the humerus 12 is disposed superior or proximal of the anatomical neck 22. The bicipital groove BG, the lesser tubercle $T_l$ and the greater tubercle $T_g$ can be disposed distal or inferior of the anatomical neck 22. In various methods and techniques the bicipital groove BG can comprise a first lateral portion LP1 and the greater tubercle $T_g$ can comprise a second lateral portion LP2. FIG. 16 shows that various muscular insertion sites MI are located between these possible anatomic landmarks. The muscular insertion site MI can include the insertion site for the Teres Minor muscle, the Infraspinatus muscle, the Supraspinatus muscle, the Subscapularis muscle, and/or other muscles and/or soft tissues. These muscular insertion sites MI can be located between an articular portion AP of the head 10 and one or both of the first lateral portion LP1 and the second lateral portion LP2. Because the muscular insertion sites MI involve soft tissues placement of a guide directly on these sites can be problematic. First, the contact on the muscular insertion sites MI may not be stable because the tissues at the muscular insertion sites MI may be soft and compressible. So, the contact may not be as intended, as planned or as desired. Also, the tissues at the muscular insertion sites MI may be subject to damage if put under pressure in the surgery or if guide pins are passed there through. Therefore advantageous guides can be produced by both providing complimentary contact surfaces to certain bone landmarks and yet avoiding any locating contact with the muscular insertion sites MI. In this contact, locating contact refers to the mating of a negative surface on the guide with a corresponding positive surface on the humerus 12 to which the negative surface has been specifically and complimentarily made.

FIGS. 17-20 show various aspects of a humeral patient specific cutting guide 800. The humeral guide 800 is configured to provide patient specific contact as well as generally avoid locating contact with any tissues that may be located at a muscular insertion site MI. FIGS. 17-18 show the humeral guide 800 located on a humerus 12. The humeral guide 800 includes a first portion 804, a second portion 808, and a third portion 812.

The first portion 804 is disposed on a portion of the humeral guide 800 that is configured to be placed over the head 10 of the humerus 12. The first portion 804 includes a first patient specific surface 806 that is configured to be complimentary, e.g., a substantial negative, of a region of the head 10, e.g., of an articular portion AP. The first portion 804 can include an arm that spaces the first patient specific surface 806 away from a more lateral portion of the humeral guide 800 which arms can span across soft tissues located at and extending from the muscular insertion sites MI. The first patient specific surface 806 can be located on a first side of the first portion 804 while a protrusion 820 can be located on a second side opposite the first side. The first side with the first patient specific surface 806 can be an inferior side. The second side with the protrusion 820 can be a superior side of the first portion 804. As used in this context inferior and superior (or distal and proximal) refer to the relative position on the bone based on the location and orientation of the corresponding bone portions in the patient when upright. That is the head 10 is generally superior (or proximal) to the shaft of the head 10, which is considered inferior (or distal).

Figure 21:
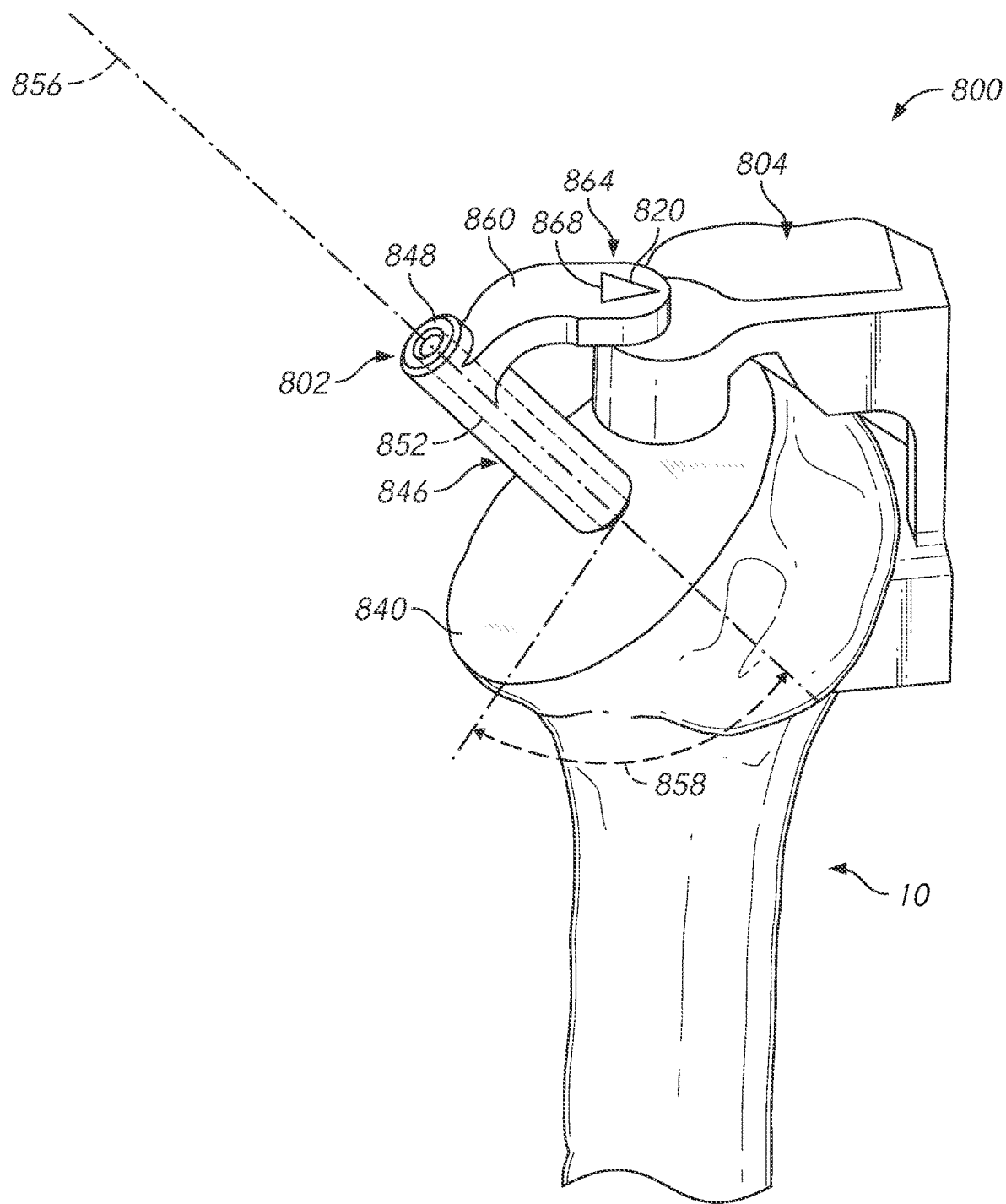
FIG. 21 is a perspective view of the guide of FIG. 17 with a guide tube coupled therewith.
Figure 22:
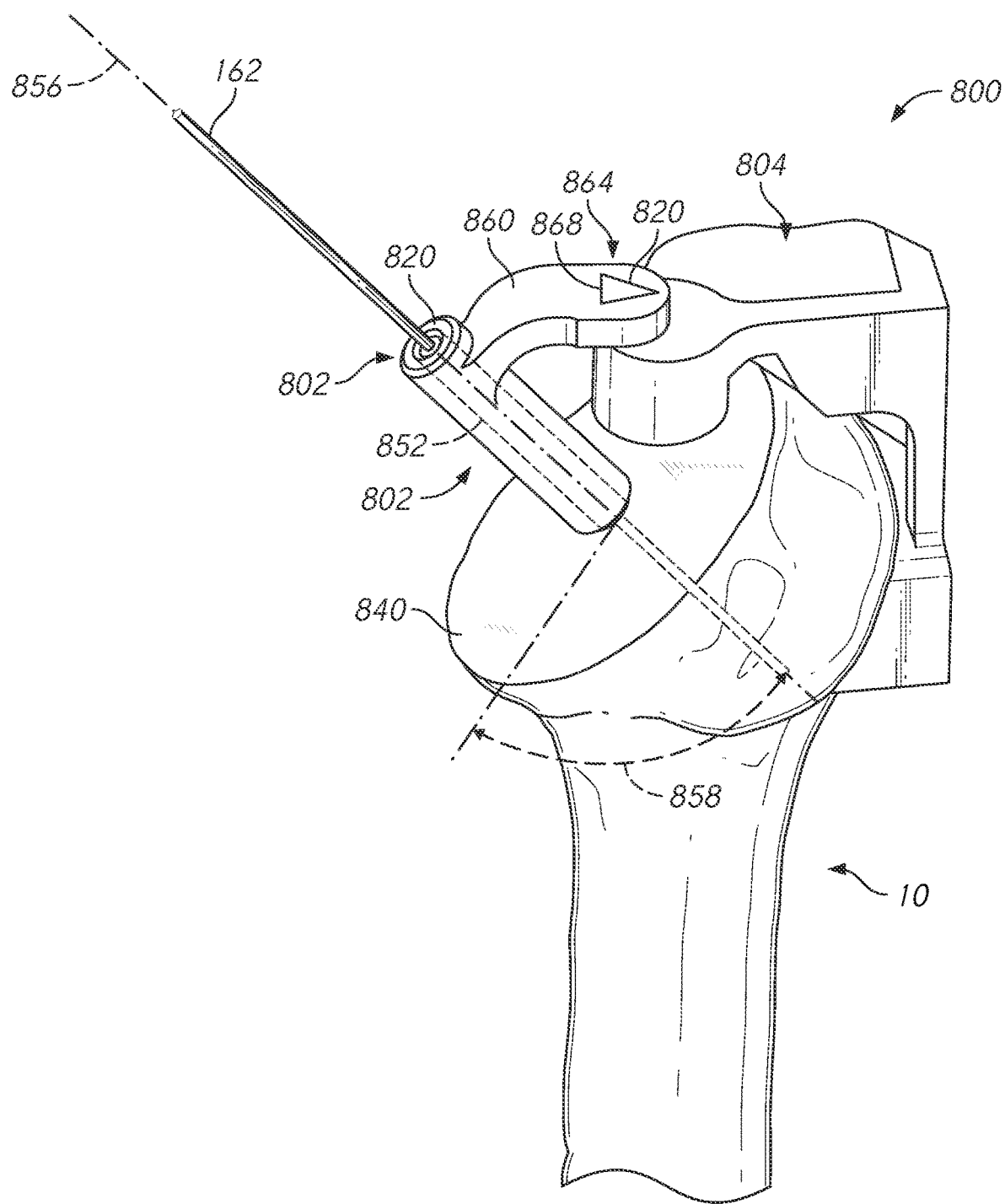
FIG. 22 illustrates a portion of a method implanting humeral implant in which a guide pin is advanced through the guide tube illustrated in FIG. 21.

FIG. 17 shows that the protrusion 820 can extend away from the arm of the first portion 804. The protrusion 820 can have a length in a direction away from the first patient specific surface 806, e.g., in a superior or proximal direction. FIG. 21 shows that the protrusion 820 can have one or more flat surfaces that facilitate mounting a guide tube 802, as discussed further below. Thus, the protrusion 820 enables a guide tube 802 to be detachably mounted to the humeral guide 800 as discussed further below.

Figure 20:
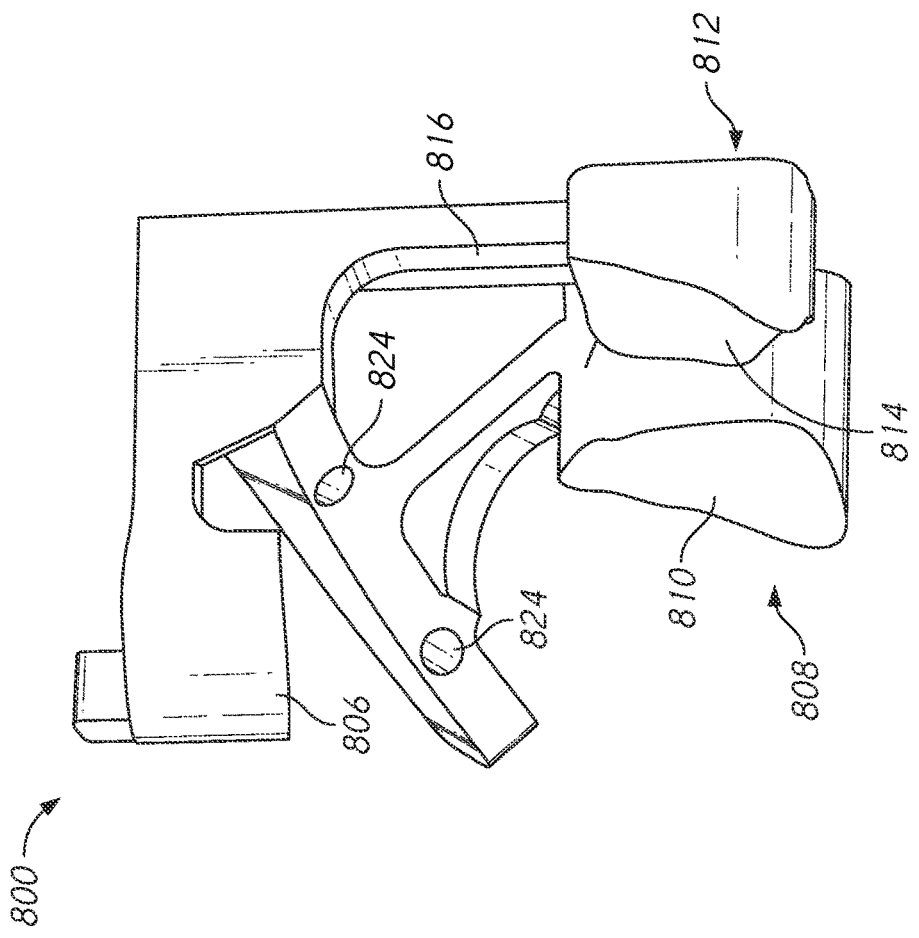
FIGS. 19-20 are perspective views of the guide illustrated in FIG. 17.
Figure 19:
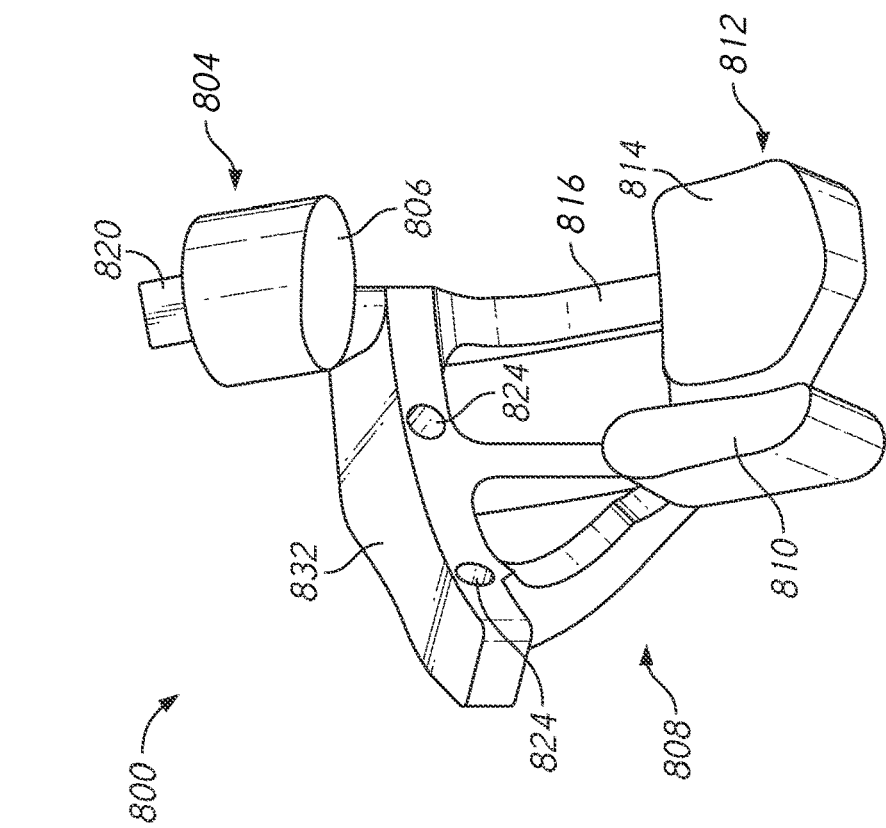

FIGS. 18-20 show the second portion 808 in greater detail. The second portion 808 includes a second patient specific surface 810 (see FIGS. 19-20) that is configured to be complimentary to a bone surface. The second patient specific surface 810 can be configured to be complimentary to the first lateral portion LP1 of the humerus 12 of a specific patient. The first lateral portion LP1 can be or comprise any prominent landmark of the humerus 12, such as the bicipital groove BG. The second portion 808 can include one or a plurality of arms that extend between the second patient specific surface 810 and a cutting plane 832 of the humeral guide 800. FIG. 19 shows that the second portion 808 can include two arms that converge on the portion of the humeral guide 800 including the second patient specific surface 810. The two arm configuration reduces the amount of material used in the guide, but in other embodiments a more continuous structure or a single arm structure can be provided to connect the second patient specific surface 810 to the cutting plane 832 or another part of the humeral guide 800.

FIGS. 17 and 19-20 show the third portion 812 in greater detail. The third portion 812 includes a third patient specific surface 814 (see FIGS. 19-20). The third patient specific surface 814 is configured to be complimentary to a bone surface. The third patient specific surface 814 can be configured to be complimentary to the second lateral portion LP2 of the humerus. The second lateral portion LP2 can be or comprise any prominent landmark of the humerus 12, such as the greater tubercle Tg. The second lateral portion LP2 can be spaced apart from the first lateral portion LP1 without contact therebetween. The third portion 812 can include one or more arms disposed between the third patient specific surface 814 and the cutting plane 832 and/or between the third patient specific surface 814 and the second patient specific surface 810.

FIGS. 17, 19 and 20 show that the humeral guide 800 can include a medial surface 816. The medial surface 816 can be disposed on a side of the humeral guide 800 facing the humerus 12. FIG. 17 shows that the humeral guide 800 is configured such that the medial surface 816 is spaced away from the humerus 12 between the third portion 812 and the first portion 804. The medial surface 816 can be spaced part from the humerus 12 between the first patient specific surface 806 and the third patient specific surface 814. In some embodiments, the medial surface 816 is spaced apart from the humerus 12 at least in the region of the anatomical neck 22. In some embodiments, the medial surface 816 is spaced apart from the humerus 12 in a manner providing a gap 818. The medial surface 816 is located such that the gap 818 will be sized to accommodate the muscular insertion sites MI.

In one embodiment, the gap 818 is sized to provide space to accommodate the attachment of the supraspinatus muscle. The gap 818 can be sized to provide space to accommodate the attachment of the Subscapularis muscle. In one embodiment, the gap 818 is sized to provide space to accommodate the attachment of the Infraspinatus muscle. In one embodiment, the gap 818 is sized to provide space to accommodate the attachment of the Teres Minor muscle. The gap 818 can be sized to provide space to accommodate the attachment of one or more of the foregoing muscles or other soft tissues including any other muscular insertion sites MI in the area.

The humeral guide 800 can have other helpful features including a plurality of mounting pin apertures 824. The humeral guide 800 also includes a cutting plane 832 as discussed above. The cutting plane 832 can be an exposed surface on the superior or proximal side of the humeral guide 800. The cutting plane 832 can be located on the humeral guide 800 between the first portion 804 and the second portion 808. The cutting plane 832 can be located on the humeral guide 800 between the first portion 804 and the mounting pin apertures 824. As discussed in the foregoing embodiments, the mounting pin apertures 824 can be used to hold the humeral guide 800 onto the lateral side of the humerus 12. The mounting pin apertures 824 can be disposed along longitudinal axes that are parallel to each other. The mounting pin apertures 824 can be disposed along longitudinal axes that are non-parallel to each other, e.g., converging toward ends disposed deeper within the humerus 12.

The humeral guide 800 can be used in a method to prepare the head 10 of the humerus 12 to receive a humeral implant. The cutting plane 832 can be used to guide a bone saw to cut off the articular portion AP of the head 10. Thereafter a resected surface is formed on the humerus 12. The humeral guide 800 can advantageously be combined with the guide tube 802 after the resected surface is formed. The guide tube 802 can include a first end to be disposed adjacent to a central portion 844 of the resected surface or resected area 840 and a second end opposite the first end. The guide tube 802 can have a mounting projection 860 coupled with and extending from the second end of the guide tube 802. The mounting projection 860 can be releaseably coupled with the humeral guide 800 at the protrusion 820. The mounting projection 860 can have a mounting aperture 864. The mounting aperture 864 can include a plurality of flats 868 that can help rotationally orient the guide tube 802 relative to the protrusion 820. The flats 868 can assure that the only one coupling position is provided to place the guide tube 802 directly over the resected area 840. More particularly, the guide tube 802 includes a cylindrical body 846 that has a guide pin aperture 848 at the second end and a central lumen 852 disposed through the cylindrical body 846 toward the central portion 844 of the resected surface.

The humeral guide 800 and the guide tube 802 can be configured to be mated in a patient specific manner to align the central lumen 852 in a pre-defined orientation to the central portion 844 of the resected surface of the humerus 12. For example, in one embodiment, the orientation of the resected surface is defined by the shape of the humeral guide 800. Thereafter the guide tube 802 can be coupled to the humeral guide 800 and when so coupled places the longitudinal axis 856 at a pre-defined orientation to the central portion 844, e.g., at an angle 858. The angle 858 can be 90 degrees in one embodiment. In other embodiments, the angle 858 can be within about 10 degrees of 90 degrees, e.g., between about 80 degrees and 110 degrees in a medial-lateral plane including the longitudinal axis of the humerus 12 or between about 80 and 110 degrees in a plane perpendicular to the resected surface of the 12.

Figure 23:
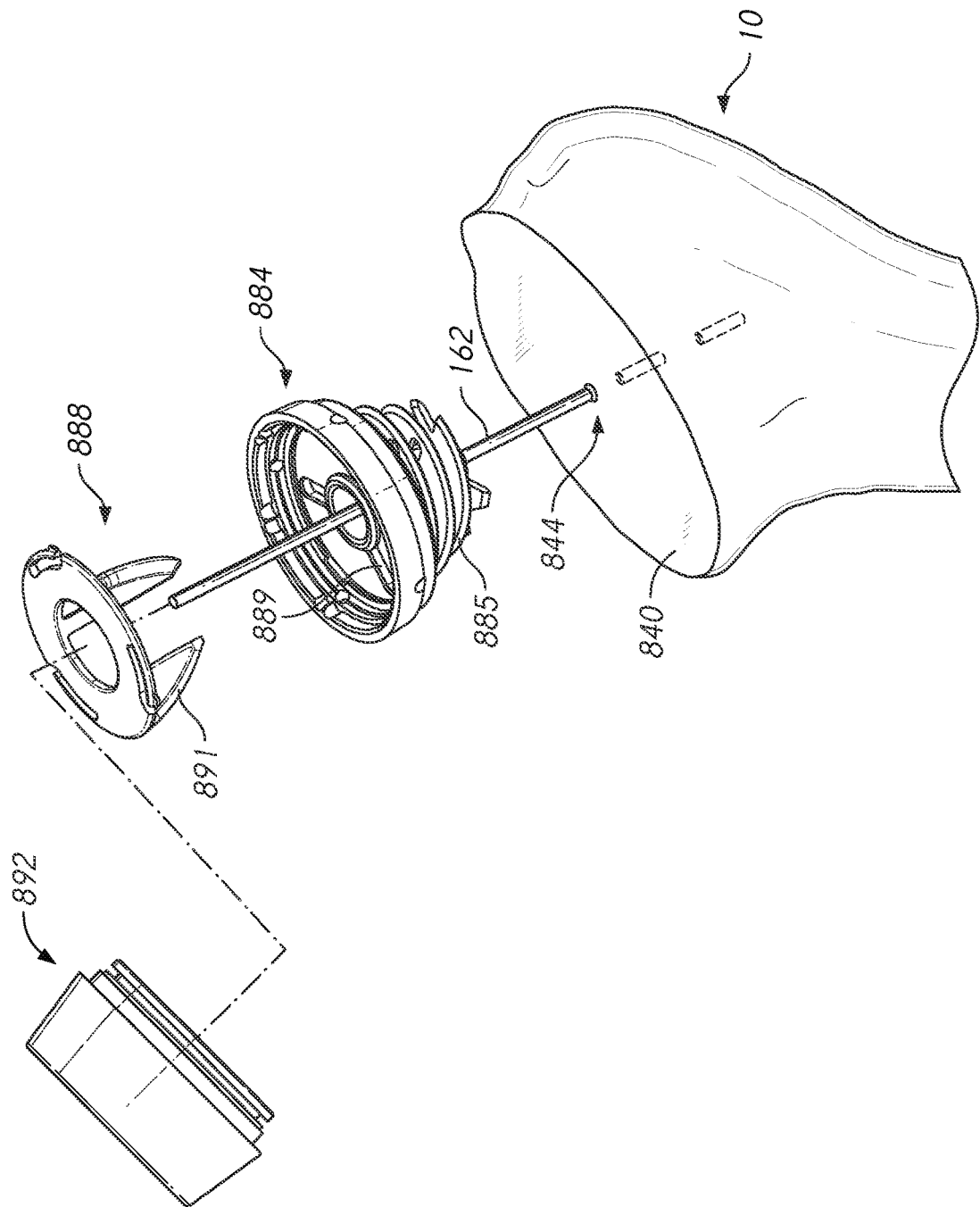
FIG. 23 illustrates an exploded view of a stemless implant that can be implanted along the guide pin illustrated in FIG. 22.

The guide tube 802 can be used to guide the guide pin 162 into the resected area 840, e.g., in the central portion 844. The guide pin can be directed at the angle 858 by advancing the guide pin 162 into the guide pin aperture 848. Further advancement can position a first end of the guide pin 162 within the bone below the resected area 840. A second end of the guide pin 162 can be accessible outside the humerus 12. Once the guide pin is in place the guide tube 802 can be removed from the protrusion 820. Thereafter, the humeral guide 800 can be removed from the lateral side of the humerus 12 leaving the guide pin 162 in place. Thereafter, a humeral anchor can be advanced along the guide pin 162. For example, the stemless anchor 884 can include a helical structure 885 to be advanced over the guide pin 162 as shown in FIG. 23. The stemless anchor 884 can include an aperture configured to receive the second end of the guide pin 162. The stemless anchor 884 can be advanced over the guide pin 162 using a tool or free hand. The helical portion or structure 885 of the stemless anchor 884 can aid in advancing the stemless anchor 884 into the central portion 844 of the resected area 840. The stemless anchor 884 can be further retained in the humerus 12 using a locking device 888. The stemless anchor 884 can one or a plurality of, e.g., three, aperture(s) 889 to receive a portion of the locking device 888. As with the stemless anchor 884 the locking device 888 can be advanced over the guide pin 162 or can be advanced freehand. The locking device 888 can include flanges or arms 891 to prevent counter-rotation of the stemless anchor 884 out of the bone beneath the resected area 840.

Once the stemless anchor 884 and the locking device 888 are secured to the resected area 840 of the humerus 12 an articular body 892 can be secured to the stemless anchor 884. The articular body 892 is illustrated as a reverse shoulder prosthesis insert, having a concave articular surface. However, a convex articular head for an anatomical configuration can be used as well. Further details of stemless anchors that can be implanted in the humerus 12 are discussed in US 2016/0324648, US2017/0273800, WO 2018/022227, U.S. 62/562,966, and U.S. 62/597,283, each of which is incorporated by reference herein in their entireties.

E. Humeral Guides Capable of having Contact Portions on Separable Components

FIGS. 24-44D illustrates multi-component patient specific humeral guides. These guides advantageously enable humeral preparation in multiple phases where one or more components of the guides can be coupled to the humerus. One or more components can be removed from the humerus in phases of the procedure. SECTION III(E)(1) illustrates embodiments in which multiple components of a guide assembly are connected by edge clips. SECTION III(E)(2) illustrates embodiments in which multiple components of a guide assembly are connected by a post and channel coupling.

1. Mulitiple Component Humeral Guide with Edge Clip Configurations

Figure 31A:
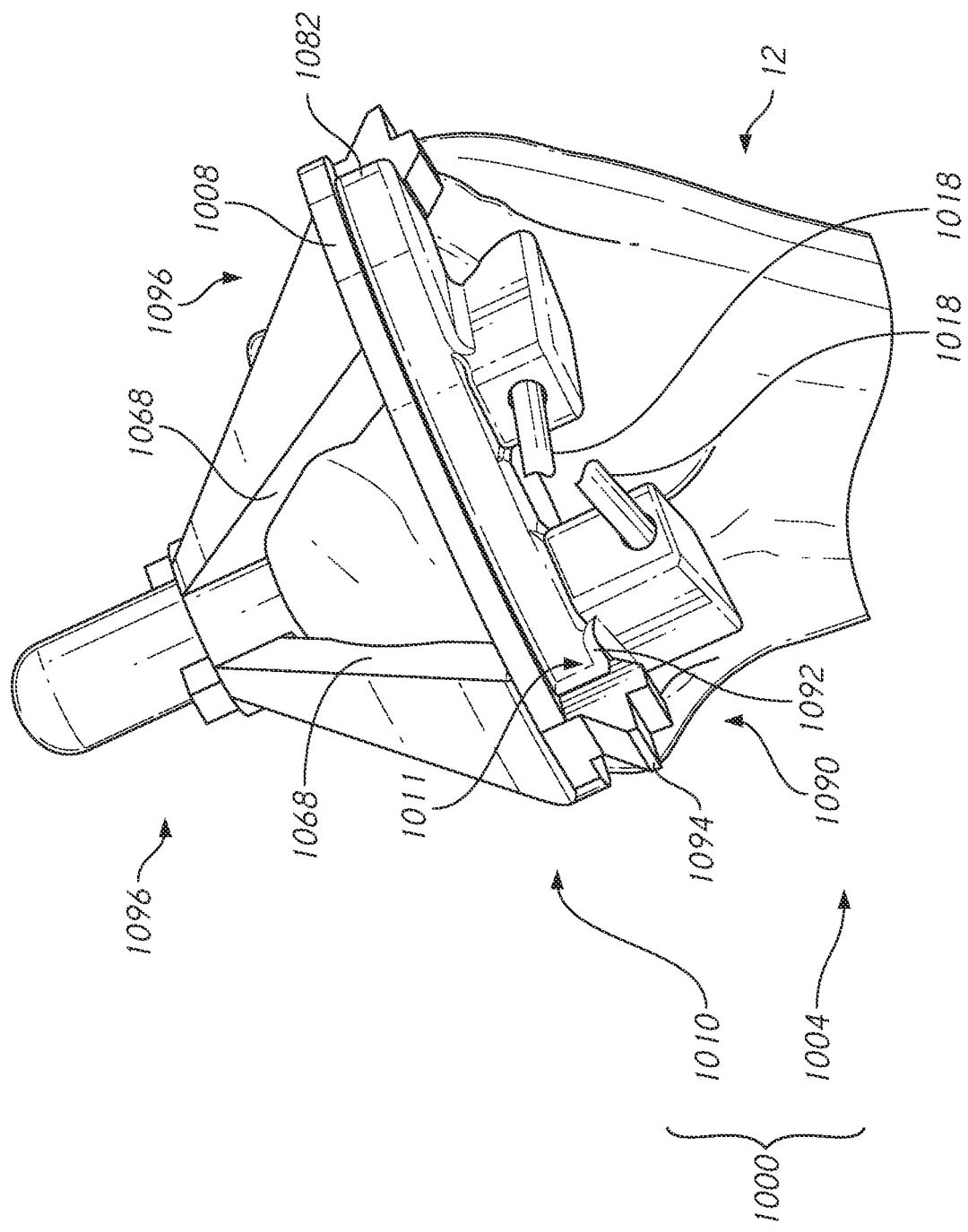
FIG. 31A shows a cutting guide assembly including the support portion of FIG. 24 and the releasable positioning jig of FIG. 29.

FIG. 31A shows a two-part humeral cutting guide 1000 that includes a support portion 1006 and a releasable positioning jig 1012. In some applications the guide 1000 is well suited for an anterior approach in resecting the humerus 12 as discussed further below. In other applications the guide humeral cutting guide 1000 can be configured for posterior, lateral or another approach. To facilitate this approach, the guide 1000 is configured to engage specific anatomy available through an anterior approach, such as one or both of the lesser tuberosity and bone at and/or between the medial calcar and the lesser tuberosity. The support portion 1006 can be used to resect the humerus 12. The positioning jig 1012 can also be configured for patient specific contact with the humeral head when combined with the support portion 1006 to form the humeral cutting guide 100.

FIGS. 24-27 show the support portion 1006 separate from the releasable positioning jig 1012. The support portion 1006 includes a first side 1008 and a second side 1010. The first side 1008 can include a resection surface 1004. As discussed below, the resection surface 1004 is used to guide a saw or other implement to cut the humerus 12 to remove the head 10 from the humerus 12. The first side 1008 also includes a surgical cue 1009, which can be in form of an arrow or other directional indicia for aligning another instrument with the support portion 1006. The use of the surgical cue 1009 to guide aspects of the procedure is discussed below in connection with FIGS. 31A-31H.

A jig retention zone 1011 that can be disposed on the support portion 1006. The jig retention zone 1011 can be configured as slots that are disposed on a side of the support portion 1006 extending between the first side 1008 and the second side 1010. The slots can be configured to receive a locking device or connector or other portion of the releasable positioning jig 1012 to retain the releasable positioning jig 1012 on the support portion 1006.

Figure 24:
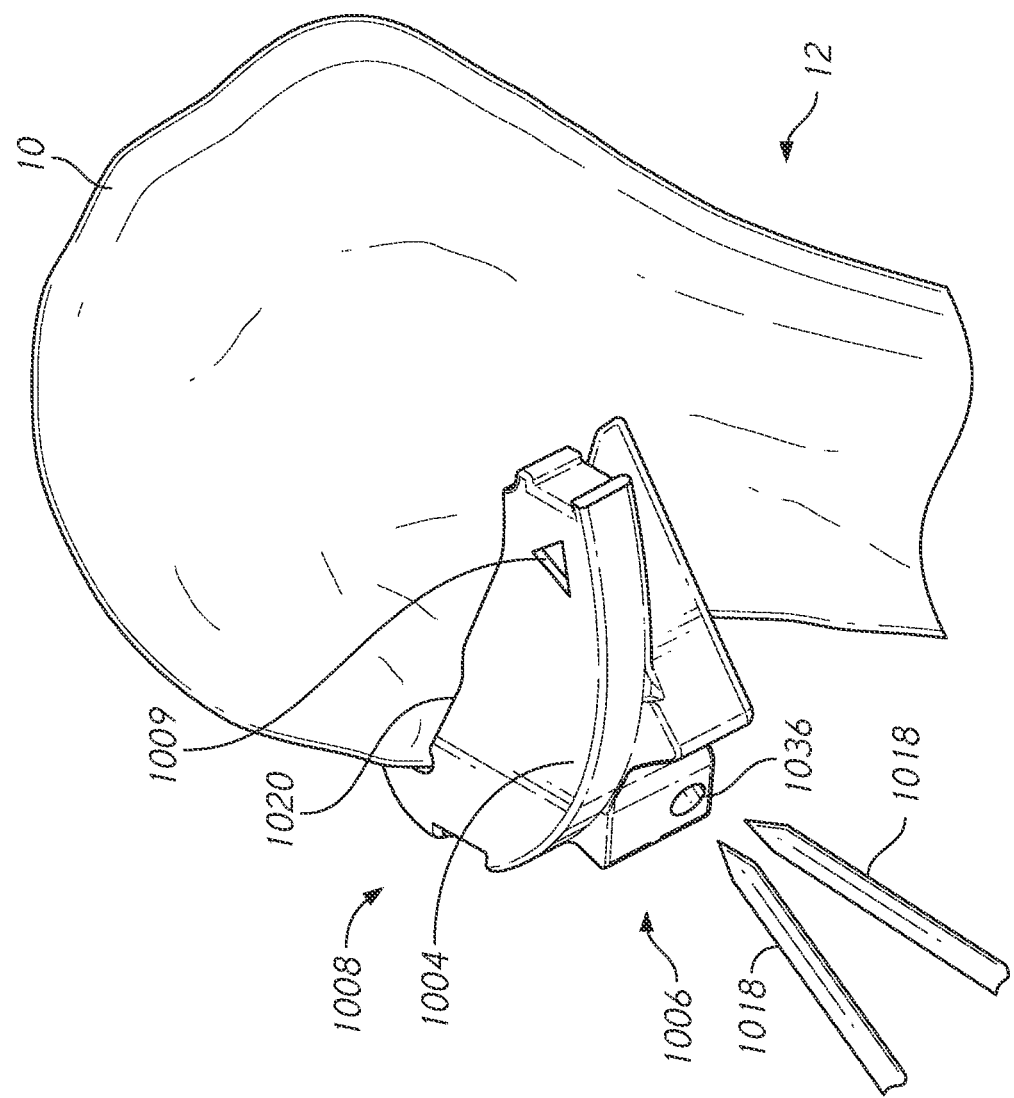
FIG. 24 shows a support portion of a humeral cutting guide and a plurality of mounting pins schematically.
Figure 25:
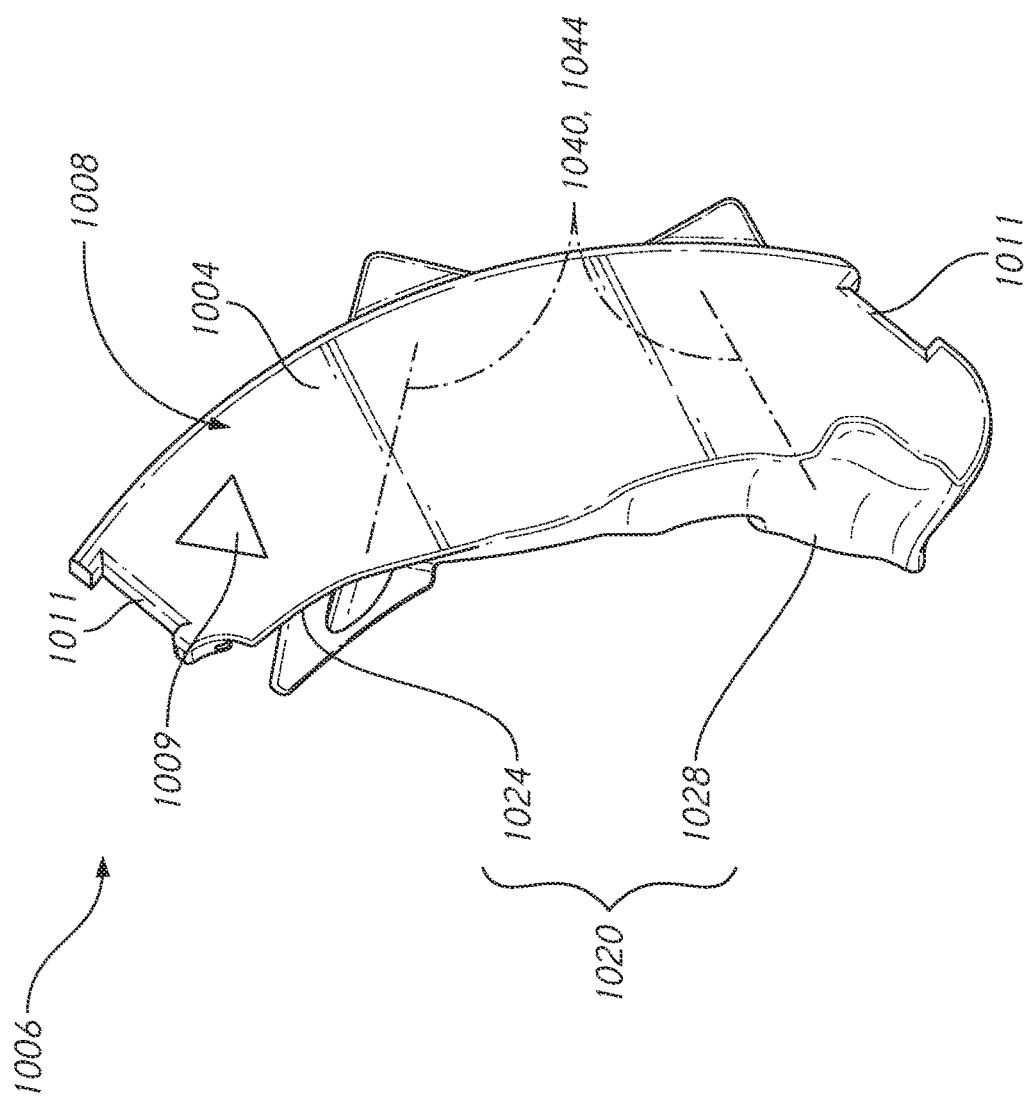
FIG. 25 is a top view of the support portion of FIG. 24 showing a resection surface thereof.
Figure 26:
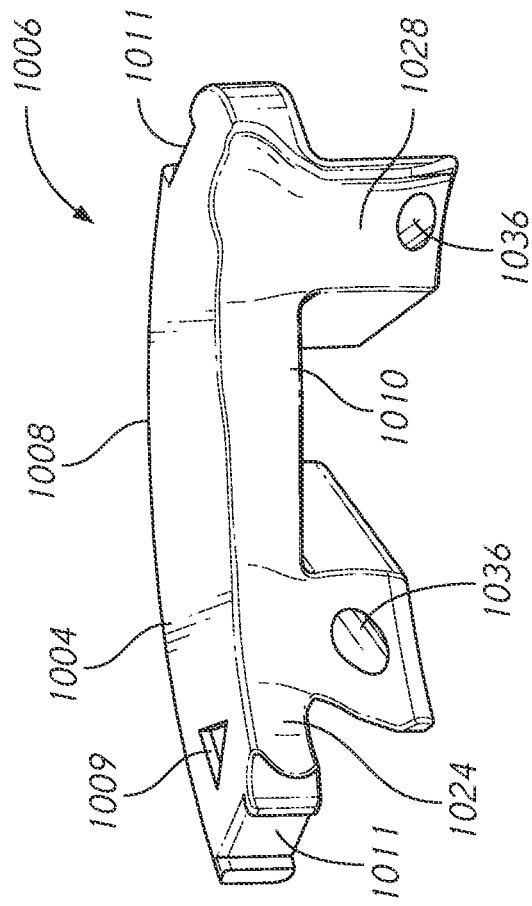
FIG. 26 is a perspective view of a side of the support portion having a contact area, the contact area configured to contact anatomy of the humerus.
Figure 27:
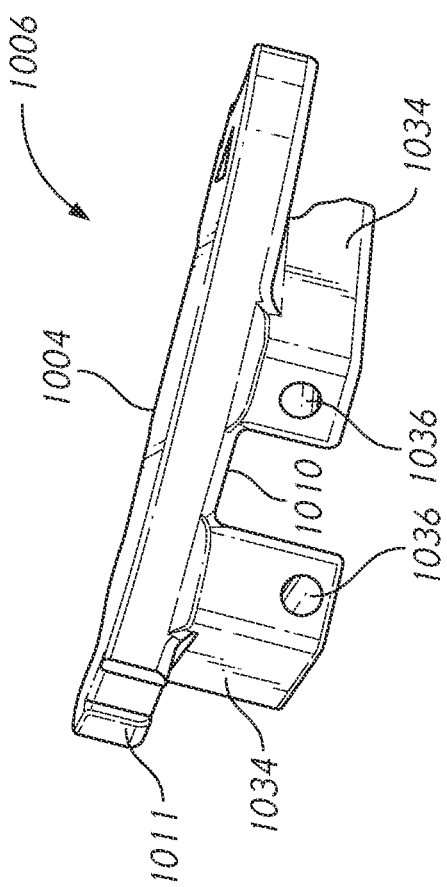
FIG. 27 is a perspective view of a side of the support portion opposite to the side illustrated in FIG. 26.
Figure 31B:
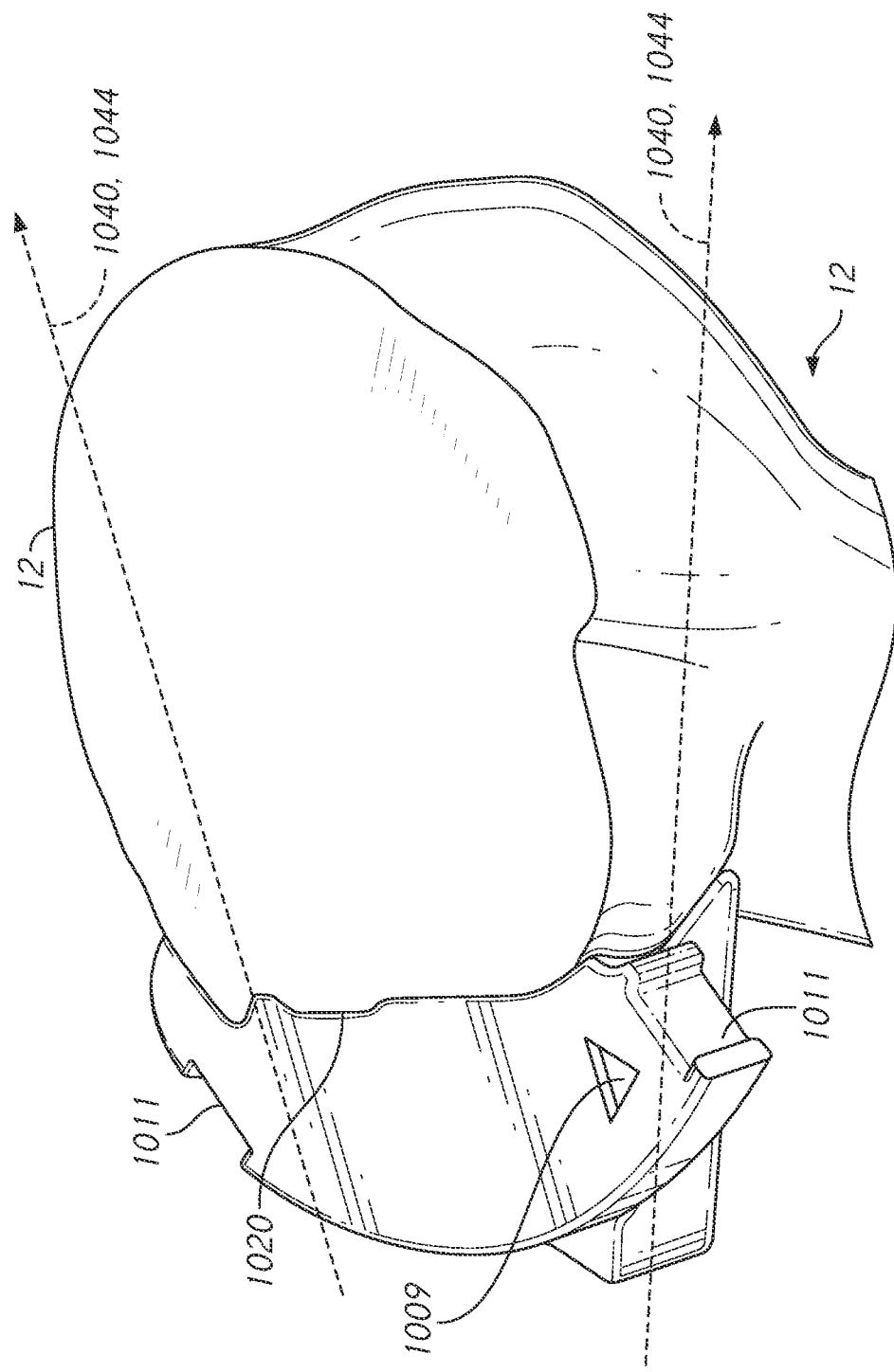
FIG. 31B shows the support portion of the cutting guide of FIG. 24 mounted to the resected humerus, and also shows the trajectory of mounting pins disposed therethrough.

The support portion 1006 has a contact area 1020 configured to receive a specific portion of a humerus of a specific patient. The contact area 1020 can comprise a substantial negative of a corresponding bone portion of the specific patient. When the contact area 1020 is disposed against the humerus 12, the support portion 1006 can be held in place with one or a plurality of stabilization pins 1018. FIGS. 24-25 and 31B show that the stabilization pins 1018 can be inserted along diverging paths 1040. A longitudinal axis 1044 can be defined through the support portion 1006 into the humerus 12 along which the longitudinal axis of the stabilization pins 1018 can be inserted. The longitudinal axis 1044 can be divergent, following or defining the diverging paths 1040.

The diverging paths 1040 can be defined by a plurality of, e.g., two mounting pin holes 1036. The holes 1036 or apertures can be formed in or on the second side 1010 of the support portion 1006. The mounting pin holes 1036 can be formed in a projection 1034 that extends from the second side 1010 to a free end of the projection. The projection 1034 can be disposed along diverging paths. The mounting pin holes 1036 can extend through a generally central portion of the support portion 1006 to the side of the support portion 1006 having the contact area 1020 from a side of the support portion 1006 opposite the side with the contact area 1020. The configuration of the projection 1034 and the mounting pin holes 1036 disposed therethrough can be generic or can be patient specific, as is discussed further below in connection with FIGS. 47-49.

In the illustrated embodiment the contact area 1020 extends generally entirely across the bone facing edge of the support portion 1006 between the first side 1008 and the second side 1010. The contact area 1020 can include sub-regions configured to engage specific portions of the humerus 12. For instance, there can be a first portion 1024 configured to be complementary to at least a portion of a lesser tuberosity of the humerus 12. The support portion 1006 can include a second portion 1028 that extends between the first side 1008 and the second side 1010. The second portion 1028 can be disposed at an opposite end of the bone facing side of the support portion 1006 from the first portion 1024. The second portion 1028 can be configured to be complementary to at least a portion of the medial calcar of the humerus 12 or can be complimentary to bone disposed at or at least partially or entirely between the medial calcar and the lesser tuberosity.

The humeral cutting guide 1000 can be formed by coupling the releasable positioning jig 1012 to the support portion 1006. In other embodiments similar to FIGS. 4, 5A, and 12 the support portion 1006 can be formed as a monolithic body with three points of contact, with a third contract region spaced away from the first portion 1024 and second portion 1028, proximal or distal to the anatomical neck.

FIG. 28 shows a 1006A that is similar to the support portion 1006 except as described differently below.

Figure 30:
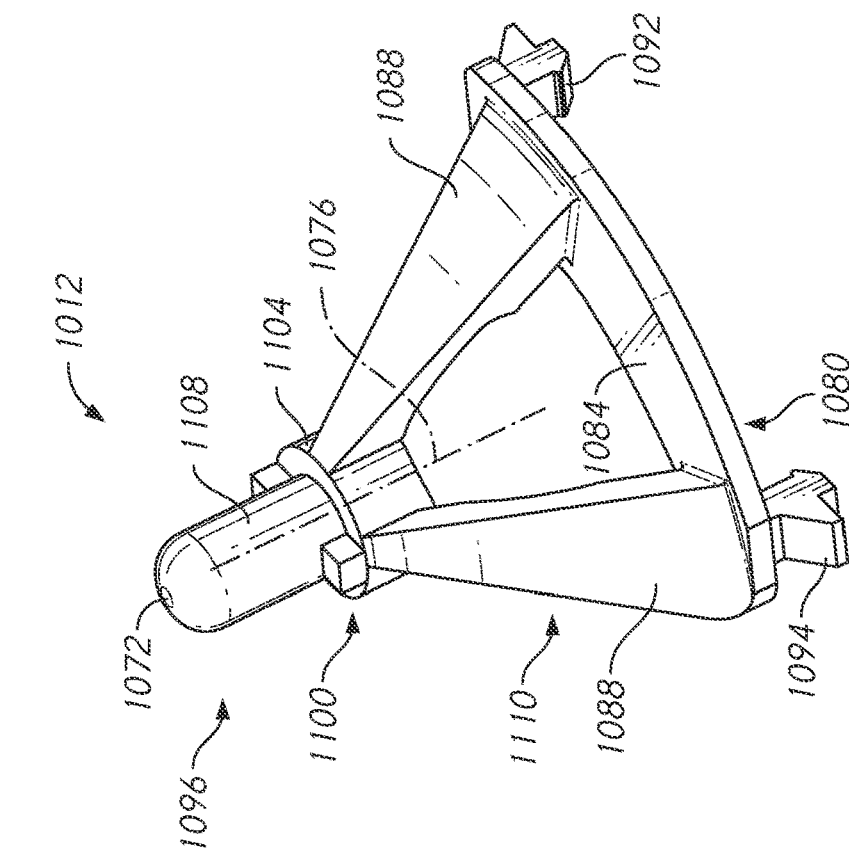
FIG. 30 is a perspective view of a side of the positioning jig opposite to the side illustrated in FIG. 29.
Figure 29:
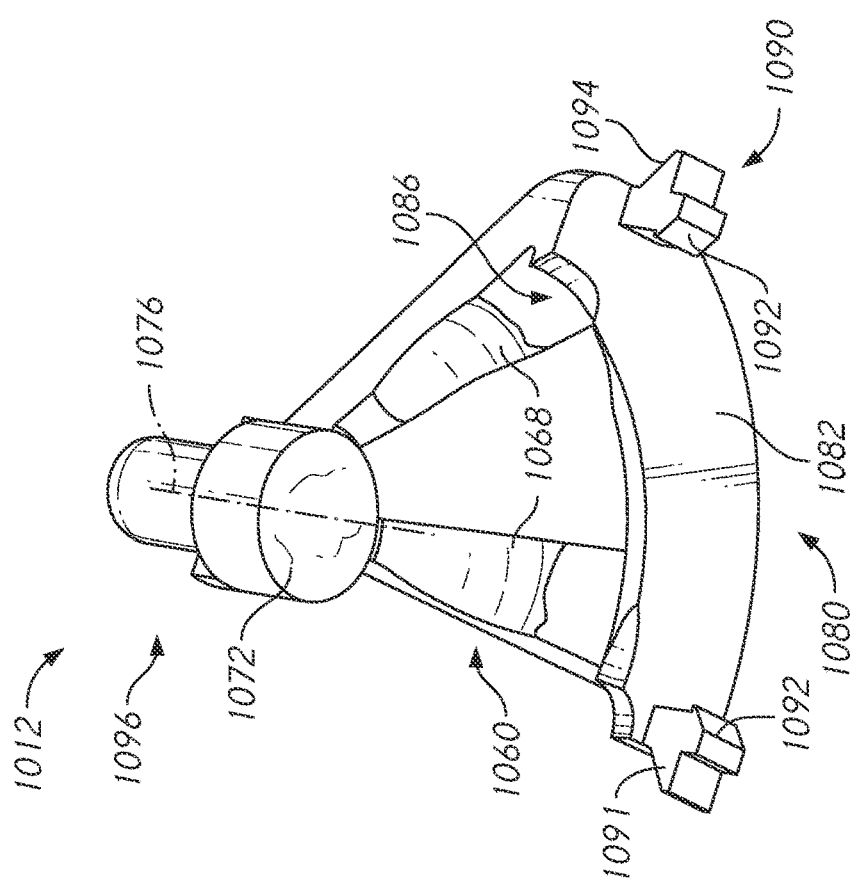
FIG. 29 is a perspective view of a side of a releasable positioning jig of a humeral cutting guide having a contact area, the contact area configured to contact anatomy of a head portion of the humerus.

FIG. 29-30 show details of the releasable positioning jig 1012. The releasable positioning jig 1012 includes a bone facing surface 1060. The releasable positioning jig 1012 has a side opposite the bone facing surface 1060. The opposite side faces away from the humerus 12 in use. The bone facing surface 1060 includes a contact area 1068. The contact area 1068 can be disposed on a bone facing side of one or a plurality of projections 1110 of the releasable positioning jig 1012. The contact area 1068 can be configured to be patient matched to a side surface of the head 10 of the humerus 12.

The releasable positioning jig 1012 can also include an aperture 1072 formed in a boss 1096 configured to rest on top of the head 10 of the humerus 12. The aperture 1072 can extend along and define an axis 1076. The axis 1076 is used to direct an instrument 1016, such as a guide pin, in to the resected humerus as discussed below.

The releasable positioning jig 1012 includes a base 1080 that has a first side 1082 and a second side 1084. A base contact area 1086 is disposed on an edge of the base 1080 that extends between the first side 1082 and the second side 1084. The base contact area 1086 can be at discrete spaced apart regions of the edge of the base 1080 that extends between the first side 1082 and the second side 1084 or can extend entirely between opposite ends of that edge. In one embodiment one end of the edge of the base 1080 that extends between the first side 1082 and the second side 1084 is configured to mate with a superior portion of a lesser tuberosity and a second end of the edge is configured to mate with a superior portion of the bone at or near the medial calcar or to a bone in a region between the medial calcar and the lesser tuberosity.

The releasable positioning jig 1012 has a generally vaulted configuration with the aperture defining boss 1096 disposed at an elevation above the base 1080. The boss 1096 is held in a predefined position and orientation by one or a plurality of, e.g., by two arms 1088. The arms 1088 can be disposed at opposite ends of the base 1080. The arms 1088 can extend from a first end coupled with the second side 1084 of the base 1080 to a second end coupled with a first portion 1104 of the boss 1096. One of the arms 1088 can be coupled with a portion of the releasable positioning jig 1012 configured to be disposed adjacent to the lesser tuberosity when the support portion 1006 is coupled to the humerus 12 and the releasable positioning jig 1012 is coupled to the support portion 1006. A bone facing side of the arms 1088 can be configured to be patient matched, e.g., to have a contact area 1068 patient matched to a portion of the head 10 of the humerus 12 superior to the lesser tuberosity. One of the arms 1088 can be coupled with a portion of the releasable positioning jig 1012 configured to be disposed adjacent to the medial calcar when the support portion 1006 is coupled to the humerus 12 and the releasable positioning jig 1012 is coupled to the support portion 1006. A bone facing side of the arms 1088 can be configured to be patient matched, e.g., to have a contact area 1068 patient matched to a portion of the head 10 of the humerus 12 superior to the medial calcar or to a region of bone disposed at or between the medial calcar and the lesser tuberosity.

The arms 1088 can have any suitable configuration. In one embodiment, the arms 1088 are tapered such that the first end coupled with the base 1080 is wider than is a second end coupled with the boss 1096. The wider dimension can be in a direction transverse to the longitudinal axis of the arms 1088.

The releasable positioning jig 1012 is connectable with the support portion 1006 in any of a number of connection mechanisms. In the illustrated embodiment, the releasable positioning jig 1012 includes one or a plurality of prongs 1090. The prongs 1090 facilitate quick and secure connection of the releasable positioning jig 1012 to the support portion 1006 and also quick disengagement to enable a surgeon using the humeral cutting guide 1000 to quickly attach or remove the releasable positioning jig 1012 from the support portion 1006. The prongs 1090 can include a projection 1091 that extends away from the first side 1082 toward the support portion 1006 when the releasable positioning jig 1012 is disposed adjacent to but not connected to the support portion 1006. The projection 1091 preferably has a length that extends greater than the thickness of the support portion 1006 between the first side 1008 and second side 1010. This configuration enables a catch mechanism 1092 of the prongs 1090 disposed at a free end of the projection 1091 to engage the support portion 1006.

In one embodiment, the support portion 1006 includes a jig retention zone 1011, as discussed above. The jig retention zone 1011 can include a groove or slot on one or both ends of the resection surface 1004. The jig retention zone 1011 can receive at least a portion of the thickness of the projection 1091 to prevent the releasable positioning jig 1012 from shifting laterally off of the support portion 1006. The catch mechanism 1092 can extend around to the second side 1010 of the support portion 1006 to resist upward or superior movement, e.g., away from the first side 1008 of the support portion 1006.

The prongs 1090 can be quickly disengaged from the support portion 1006. The prongs 1090 can have a release member 1094 at a side opposite the catch mechanism 1092. The release member 1094 can be gripped by a surgeon finger to deflect projection 1091 from the side of the projection 1091 upon which the release member 1094 is located to cause the catch mechanism 1092 to move out from under the second side 1010 of the support portion 1006. Such movement causes the catch mechanism 1092 to move outward of the second side 1010 of the support portion 1006. Outward movement of the catch mechanism 1092 allows the releasable positioning jig 1012 to disengage or to be released from the support portion 1006. Other coupling mechanisms to secure a releasable positioning jig to the support portion 1006 can be utilized, as discussed below. Also, in some techniques, the releasable positioning jig 1012 is not required and the head 10 can be resected using the support portion 1006 without requiring the releasable positioning jig 1012.

The releasable positioning jig 1012 can facilitate placement of an instrument, such as a guide pin 1016 in the humerus. For example, the boss 1096 can have an aperture 1072, as discussed above. The aperture 1072 can extend from a first end of a first portion 1104 to a second end of a second portion 1108. The first portion 1104 can extend from the first end to a second end where the first portion 1104 is coupled with the second portion 1108. The second portion 1108 can extend from a first end at the first portion 1104 to the second end where the aperture 1072 opens above the boss 1096. When the releasable positioning jig 1012 is mounted to the support portion 1006 the aperture 1072 allows a pin or other instrument 1016 to be delivered into the humerus 12 as discussed further below.

The boss 1096 can include an orientation feature 1100 that allows for a confirmation of orientation during surgery. For example, although the support portion 1006 is patient matched by having a surface or having surfaces configured to engage specific portions of the humerus 12, the correct positioning of the humeral cutting guide 1000 can be confirmed by visually confirming alignment of the orientation feature 1100 with an anatomical feature or orientation of the humerus 12. The orientation feature 1100 also could be used to confirm orientation of a surgical instrument relative to the releasable positioning jig 1012. The orientation feature 1100 can mate with a corresponding surface having a recess or recesses with the same shape as the orientation feature 1100 to allow for only one or two or a limited number of confirmed orientations relative to the releasable positioning jig 1012.

FIG. 28 shows a support portion 1006A that can be used alone to support a surgical saw or can be combined with another instrument, such as the releasable positioning jig 1012 to form another embodiment of the humeral cutting guide 1000. Connection between the support portion 1006A and the releasable positioning jig 1012 can be by way of the jig retention zone 1011, as shown. The support portion 1006A can have a contact area 1020 that is patient matched, e.g., that is a substantial negative of the surface of the humerus 12 to which the support portion 1006A is to be mated. The contact area 1020 can be mated to one or both of the lesser tuberosity and the bone adjacent to the medial calcar. FIG. 28 shows that in one variation, the contact area 1020 can extend from the lesser tuberosity continuously toward the medial calcar. The support portion 1006A can include many of the same features as the support portion 1006, such as a first side 1008 having a resection surface 1004. The support portion 1006A also can include one or a plurality of mounting pin holes 1036 disposed therethrough. As discussed above in connection with support portion 1006, the mounting pin holes 1036 can be disposed through a projection 1034A of the support portion 1006A.

The support portion 1006A can include a second contact portion, such as a second contact level 1030. The second contact level 1030 can be disposed distally relative to the contact area 1020. The second contact level 1030 can be configured to mate with any specific patient bone, such as a portion of the humerus 12 disposed at or adjacent to the junction between the metaphyseal and diaphyseal portions of the humerus 12. In some cases, the humerus 12 has a depression or groove in the portion thereof where the diaphysis and the metaphysis come together. This depression or groove can be disposed generally transverse to the longitudinal axis of humerus 12 on an anterior side surface of the humerus 12. The support portion 1006A thus provides a plurality of contact zones spaced apart in a proximal-distal direction of the humerus 12. The support portion 1006A also provides contact at a plurality of spaced apart anatomies at one or more of such contact zones. As discussed above, the contact area 1020 can contact a continuous area at and between the lesser tuberosity and the medial calcar and/or can contact these anatomies while leaving a portion therebetween out of contact with the support portion 1006A.

When the support portion 1006A is combined with the releasable positioning jig 1012 into a variation of the humeral cutting guide 1000 there is contact with the head 10. Thus the humeral cutting guide 1000 including the support portion 1006A can provide contact with the humerus 12 at three areas including the humerus, the area at one or both of or entirely between the lesser tuberosity and the medial calcar and at the metaphyseal-diaphyseal junction.

FIGS. 31A-31H show methods of using the humeral cutting guide 1000, including the support portion 1006. Although the support portion 1006 is shown in these figures in connection with a method, the support portion 1006A illustrated in FIG. 28 and described above can be used for the methods described in connection with FIGS. 31A-31H. The support portion 1006 can be coupled with the humerus 12. The support portion 1006 is held against the humerus 12 in a position that is pre-determined. The position is predetermined by surgical planning, as described above in connection with FIG. 3 and below in connection with FIGS. 47-49. The support portion 1006 is then secured to the humerus 12 by a plurality of stabilization pins 1018. The stabilization pins 1018 preferably have longitudinal axes 1044 that are oriented along diverging paths 1040 through the humerus 12. Examples of these paths are shown in FIG. 31B, but as discussed below in connection with FIG. 47-49, the paths can vary from patient to patient based on a number of criteria carried out in surgical planning.

FIG. 31A shows the releasable positioning jig 1012 coupled with the support portion 1006. This can be accomplished by moving the first side 1082 of the releasable positioning jig 1012 toward the first side 1008 of the support portion 1006 until the catch mechanism 1092 abuts the first side 1008. Further movement causes the projection 1091 to deflect laterally away from the central area of the first side 1008. Once the catch mechanism 1092 moves past the second side 1010 of the support portion 1006 the catch mechanism 1092 deflects back to overlap a portion of the second side 1010. A portion of the thickness of the projection 1091 comes to rest on or in a slot or other similar feature of the jig retention zone 1011. This connection can be made pre-operatively or can be made after the support portion 1006 is secured to the humerus 12. By providing contact along the contact area 1020 of the support portion 1006 and also along the contact area 1068 of the releasable positioning jig 1012, the surgeon can clearly see and feel that the humeral cutting guide 1000 is in the proper position. In one method, after the releasable positioning jig 1012 is coupled to the support portion 1006 the humeral cutting guide 1000 is placed against the humerus 12 with these contacts areas in contact with the head 10 and with portions distal the anatomical neck 22, e.g., with the lesser tuberosity and at or adjacent to the medial calcar. Thereafter the stabilization pins 1018 can be secured to the humerus 12 through the mounting pin holes 1036.

FIG. 31B shows that the humerus 12 following resection along the resection surface 1004, located on the first side 1008 of the support portion 1006. In the illustrated embodiment, the first side 1008 and the first side 1082 are in direct contact when the support portion 1006 is coupled with the releasable positioning jig 1012. To resect the humerus 12 the releasable positioning jig 1012 is removed by disengaging the catch mechanism 1092 from the support portion 1006. The releasable positioning jig 1012 can be taken out of the surgical field. A saw blade can be brought into the surgical field and can resect along the resection surface 1004. The surgical cue 1009 can indicate a direction of initial resection, though the resection can proceed across the resection surface 1004 in any suitable manner.

In some variations there is a gap between the first side 1008 and the first side 1082, similar to the gap forming the cutting plane 114 in the humeral cutting guide 100, such that a saw can be inserted therebetween.

With the releasable positioning jig 1012 removed a continuous zone of contact can be seen at the contact area 1020 between the support portion 1006 and the humerus 12. The contact area 1020 can extend between jig retention zones 1011 on each end of the support portion 1006.

Figure 31C:
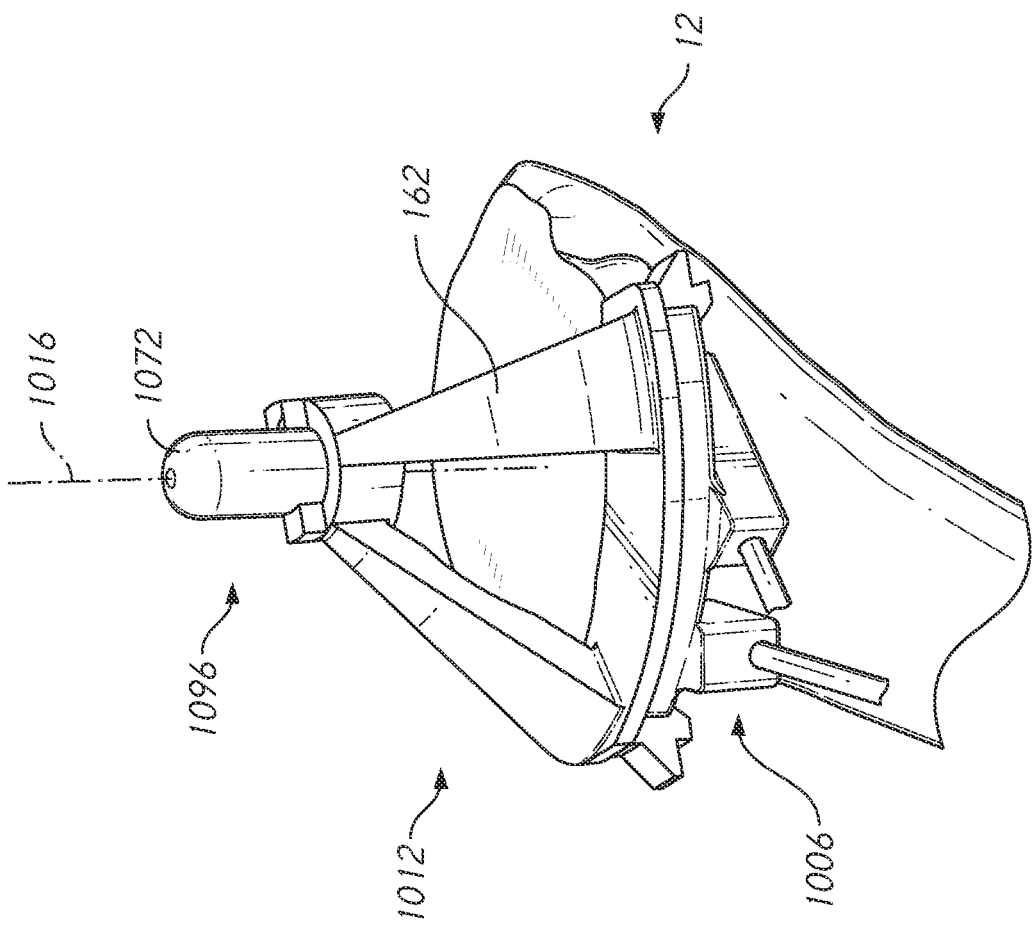
FIG. 31C shows a portion of a method in which a resected head portion has been removed from the humerus and the releasable positioning jig illustrated in FIG. 29 has been reconnected to the support portion, the jig enabling placement of a guide pin into the resected humerus.

FIG. 31C shows that following resection as shown in FIG. 31B, the releasable positioning jig 1012 can be mounted to the support portion 1006 (or re-mounted if the jig had been removed prior to resection). The releasable positioning jig 1012 can provide a guide to placing an instrument such as the guide pin 1016. The guide pin 1016 can be advanced through the aperture 1072 toward the resected surface of the humerus 12 and into the cancellous bone therebelow.

Figure 31D:
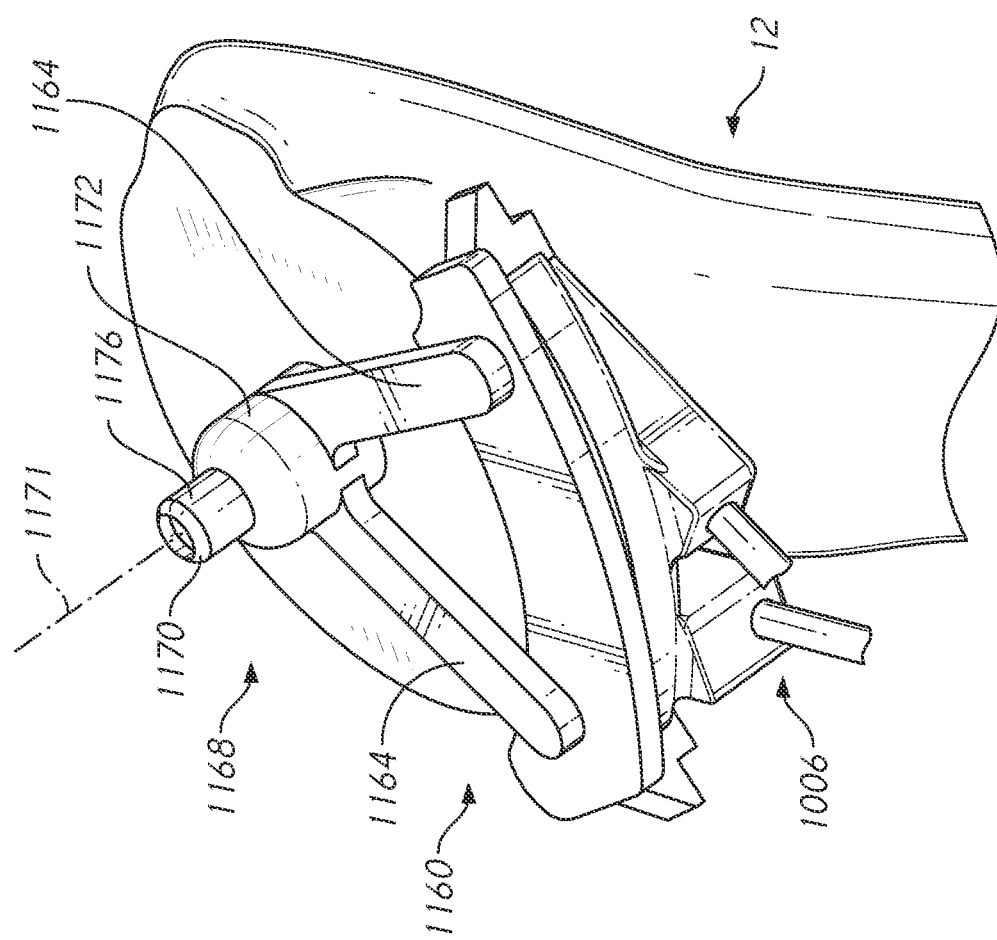
FIG. 31D shows another embodiment of a releasable positioning jig that can be coupled with the support portion of FIG. 24 for placement of a guide pin.

FIG. 31D shows that in some embodiment, another embodiment of a releasable positioning jig 1160 can be used to place the guide pin 1016 or another instrument. The releasable positioning jig 1160 can be similar to the releasable positioning jig 1012 but in one embodiment is not required to be configured with a patient specific surface. Rather, the releasable positioning jig 1160 can have a generally flat configuration in which projections 1164 extend from a base that is similar to the base 1080. The projection 1164 can have a first end coupled with the base and a second end spaced away from the base. The projection 1164 can have a second end coupled with a boss 1168. The boss 1168 can be disposed in a patient specific location or can be in a generic position or location. The boss 1168 can have an aperture 1170 that defines an axis 1171 that extend therethrough. The aperture 1170 is configured to guide the guide pin 1016 into the humerus 12. The boss 1168 can be configured with a larger first portion 1172 that is coupled with the projection 1164 and a smaller second portion 1176 disposed above the first portion 1172. The larger first portion 1172 provides greater rigidity than had the boss 1168 had the same dimension as the second portion 1176.

The releasable positioning jig 1160 can provide the same function as the releasable positioning jig 1012, but can provide more accurate placement of the guide pin 1016 because the releasable positioning jig 1160 may be supported by the resected surface of the humerus 12. Also, the projection 1164 can have a shorter extent than the arms 1088 of the releasable positioning jig 1012.

Figure 31E:
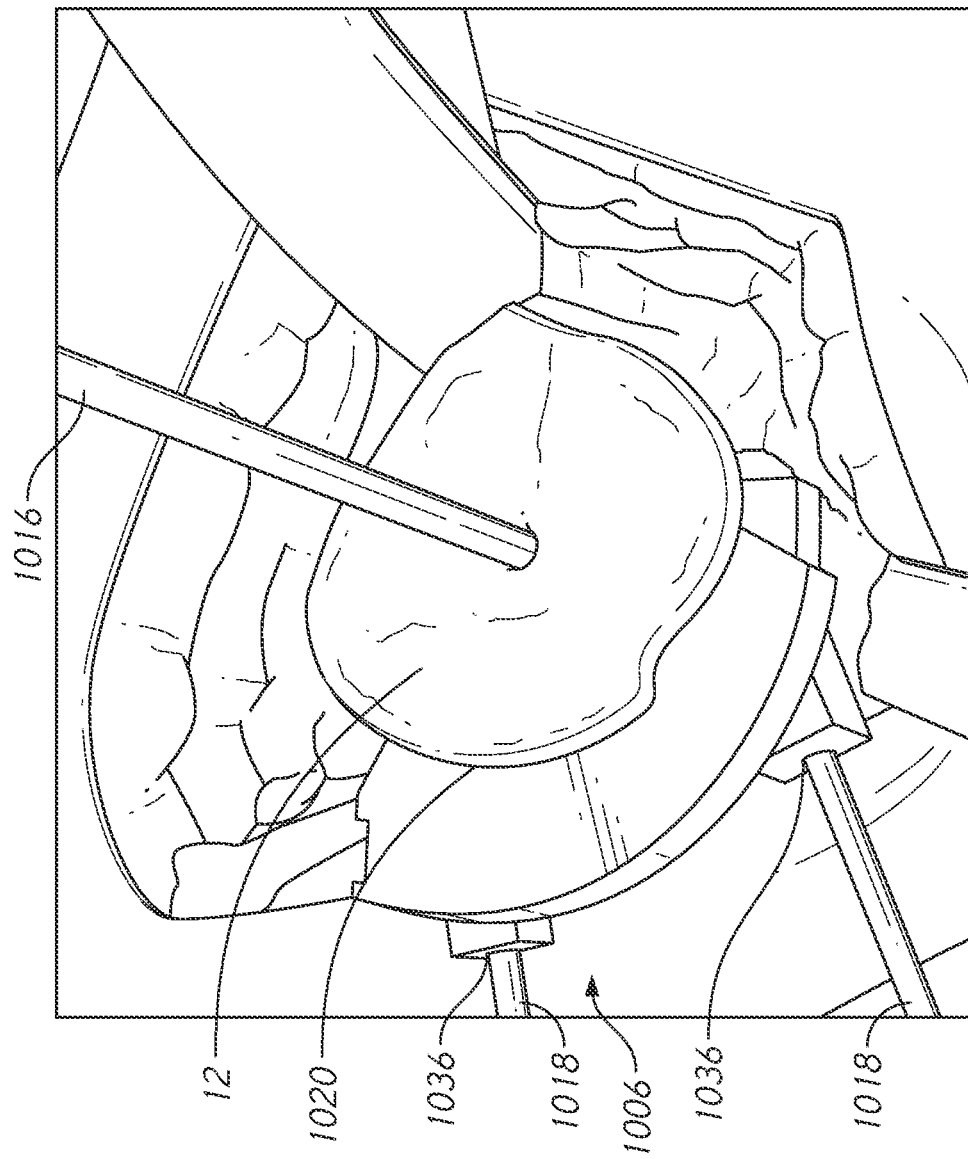
FIG. 31E shows the guide pin placed into the resected surface of the humerus and the positioning jig removed from the support portion.

FIG. 31E shows the support portion 1006 supported by a plurality of divergent stabilization pins 1018 against an anterior portion of the resected humerus 12. The guide pin 1016 is shown extending out of the humerus 12. The contact area 1020 is shown closely following the natural shape of the humerus 12. The guide pin 1016 can be accessed to further prepare the humerus 12, as discussed further below.

Figure 31F:
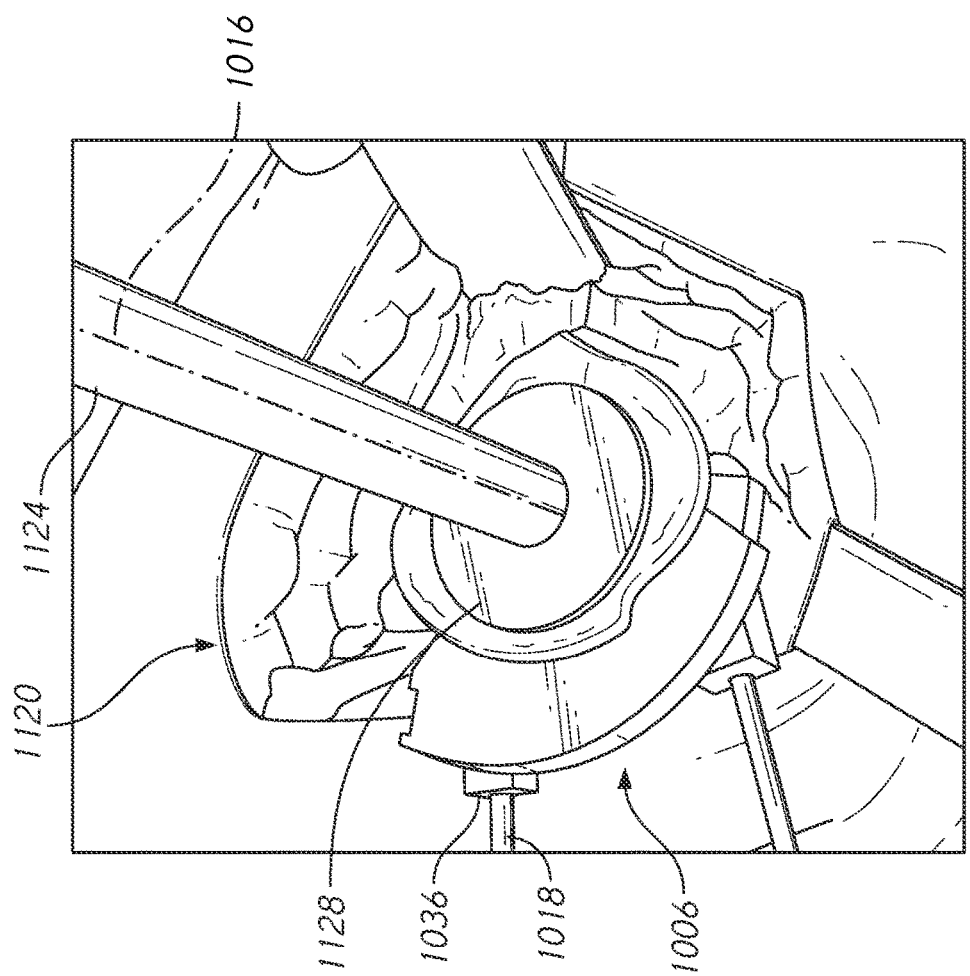
FIG. 31F shows preparation of the cancellous bone of the humerus using a cannulated reamer device.

FIG. 31F is a step following that of FIG. 31E, in which a reamer 1120 is advanced over the guide pin 1016. The reamer 1120 can include a reamer head 1128 and a shaft 1124. The shaft 1124 is cannulated, that is, having a lumen therethrough sized to receive the guide pin 1016 such that the shaft 1124 can be advanced over the guide pin 1016. The reamer head 1128 can be configured to form a recess in the humerus 12 distal the resection to receive an implant.

Figure 31G:
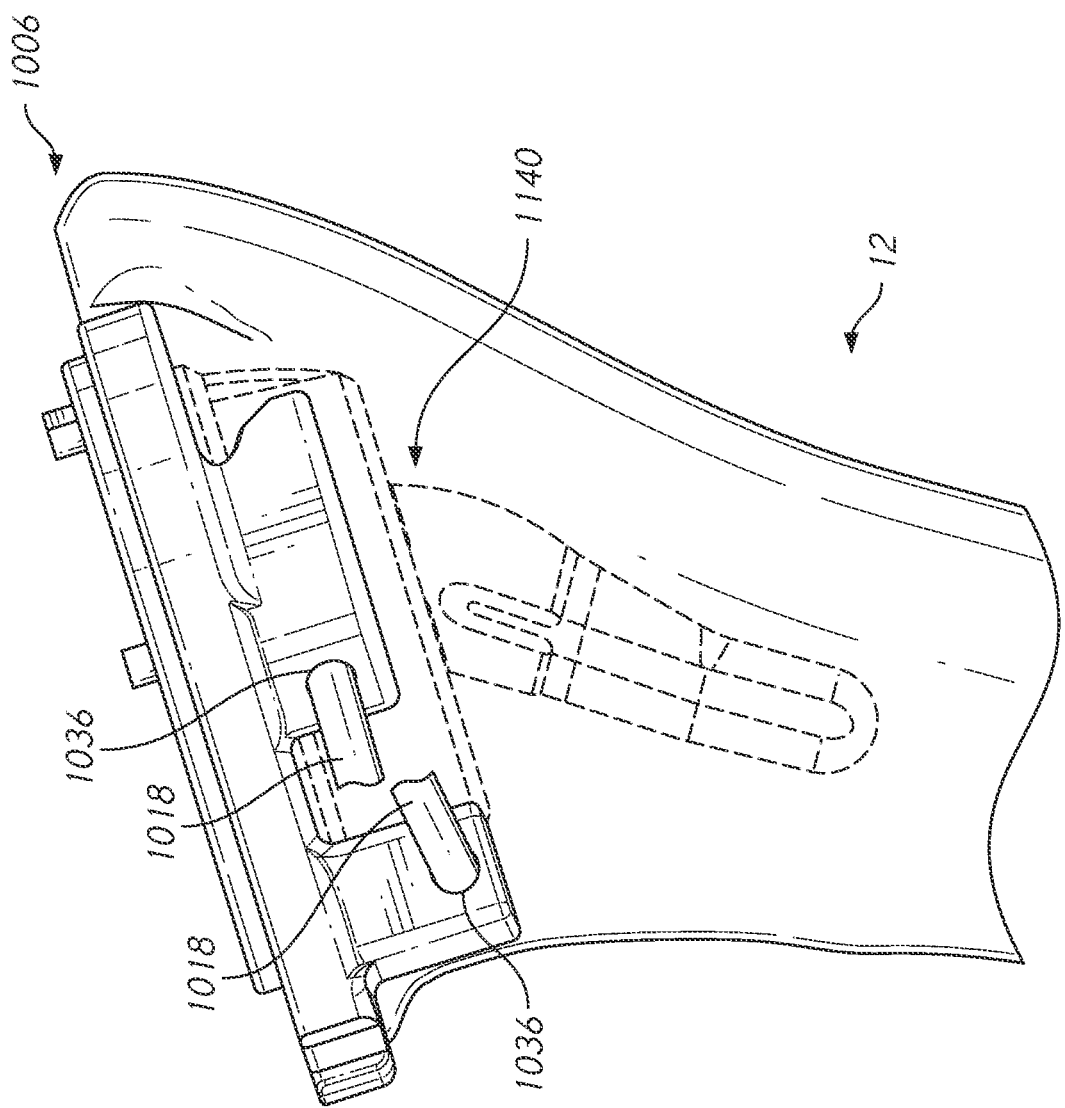
FIG. 31G shows placement of a humeral anchor with a stem with the support portion of FIG. 24 remaining in place on the side of the humerus.
Figure 31H:
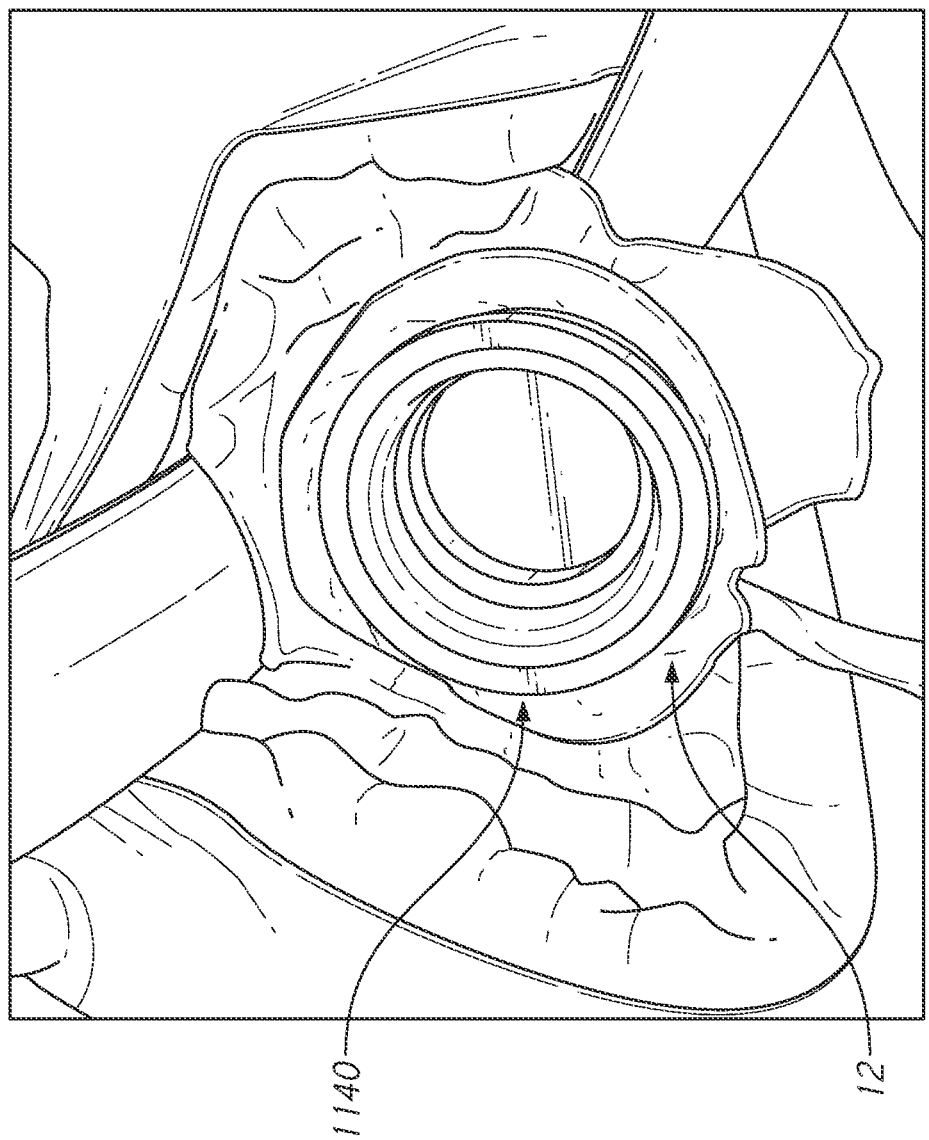
FIG. 31H shows the humeral anchor from a superior perspective, the support portion of the cutting guide having been removed.

FIGS. 31G and 31H show that the process follows to placement of a stem 1140 in the humerus 12. The placement of the stem 1140 can be achieved even with the support portion 1006 in place, as shown in FIG. 31G. FIG. 31H shows the stem 1140 in place after the support portion 1006 has been removed from the humerus 12.

The humeral cutting guide 1000 provides several advantages, including enabling one or more removable positioning jigs to be coupled with the support portion 1006 to facilitate the placement of the stem 1140. Also, the support portion 1006 has divergent stabilization pins 1018, which divergent paths can be patient specifically determined, as discussed in connection with FIGS. 47-49 below.

2. Mulitiple Component Humeral Guide with Post Locking Configuration

FIGS. 32-44D shows humeral cutting guides 1200, 1500 and related components. These guides allow for two component assembly to facilitate slideable connection for convenient preparation of the humerus.

a. Guides with Enhanced Access Configurations and Capable of Lateral or Posterior Approaches FIGS. 32-37G shows humeral cutting guides 1200. The guide 1200 is similar in some respects to the guide 1000 discussed above. The description of the guide 1000 may supplement the description of the guide 1200 where similar and vice versa. Differences between the guide 1000 and the guide 1200 are discussed below.

As discussed further below, the humeral cutting guide 1200 is configured for a lateral and posterior approach to the humerus. For example, the guide 1200 can be configured for patient specific or patient matched contact with anatomy accessible from a lateral or a posterior approach. The guide humeral cutting guide 1200 could be configured for an anterior or another approach. The guide 1200 can have a plurality of contact areas. The guide 1200 can have a contact area configured to contact the bicipital groove. The guide 1200 can have a contact area configured to contact a greater tuberosity. In one form the guide 1200 has a support portion 1206 and a positioning jig 1212 are used, the guide 1200 can also be configured for patient specific contact with the head 10 of the humerus 12.

Figure 32:
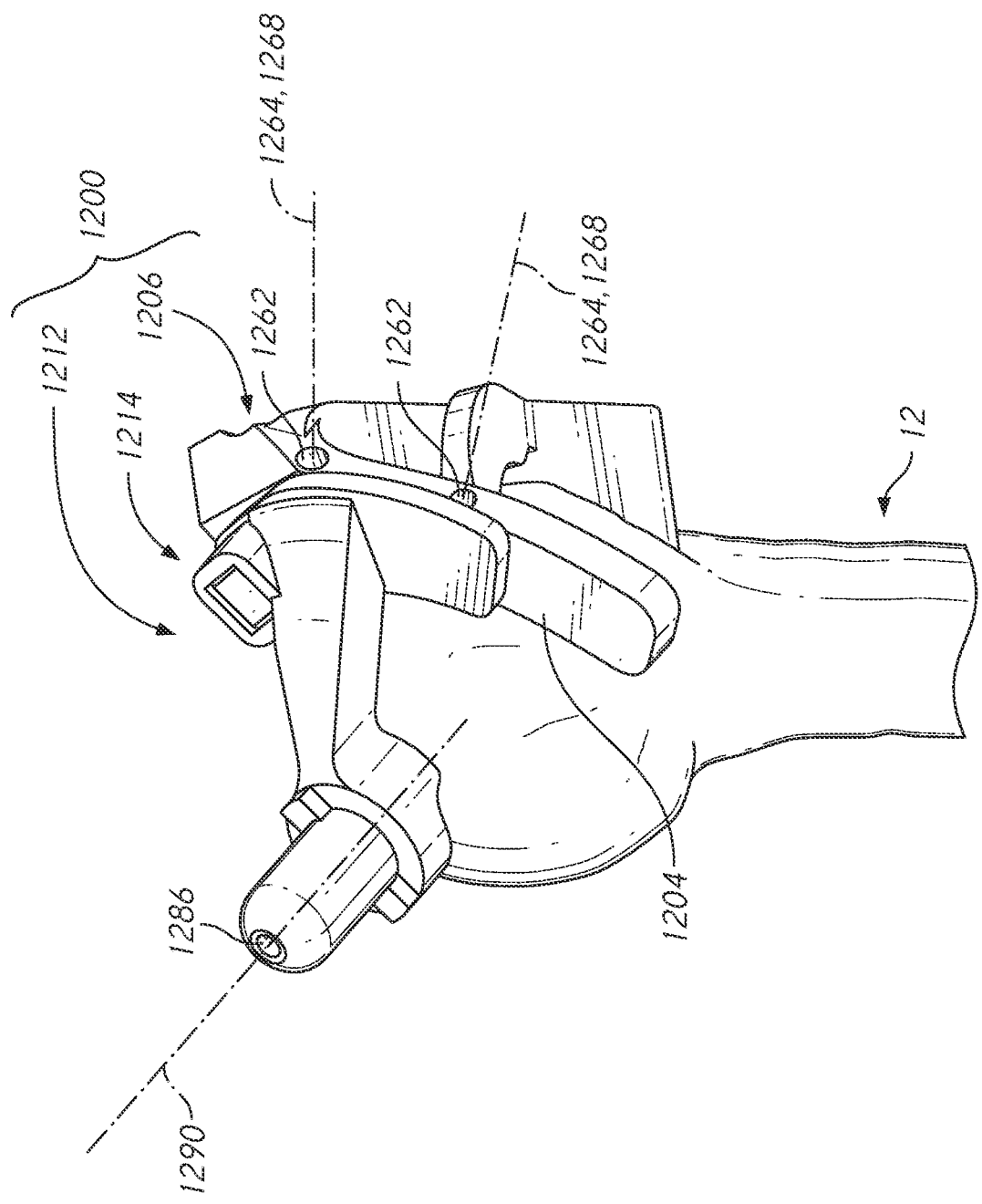
FIGS. 32-33 show a humeral guide coupled with a humerus, the humeral guide having a support portion and a releasable positioning jig.

FIG. 32 shows that the humeral cutting guide 1200 has a resection surface 1204 that is adapted for cutting the head 10 off of the proximal end of the humerus 12. The resection surface 1204 is at least partially exposed when the releasable positioning jig 1212 is coupled with the support portion 1206. The positioning jig 1212 can be coupled to the support portion 1206 by a connection mechanism 1214, which differs from that of the humeral cutting guide 1000. The support portion 1206 includes a first side 1208 upon which the resection surface 1204 is formed and a second side 1210 opposite the first side 1208. The support portion 1206 can also have a surgical cue 1209 disposed thereon. The surgical cue 1209 can convey a direction for another instrument as discussed further below.

Figure 36:
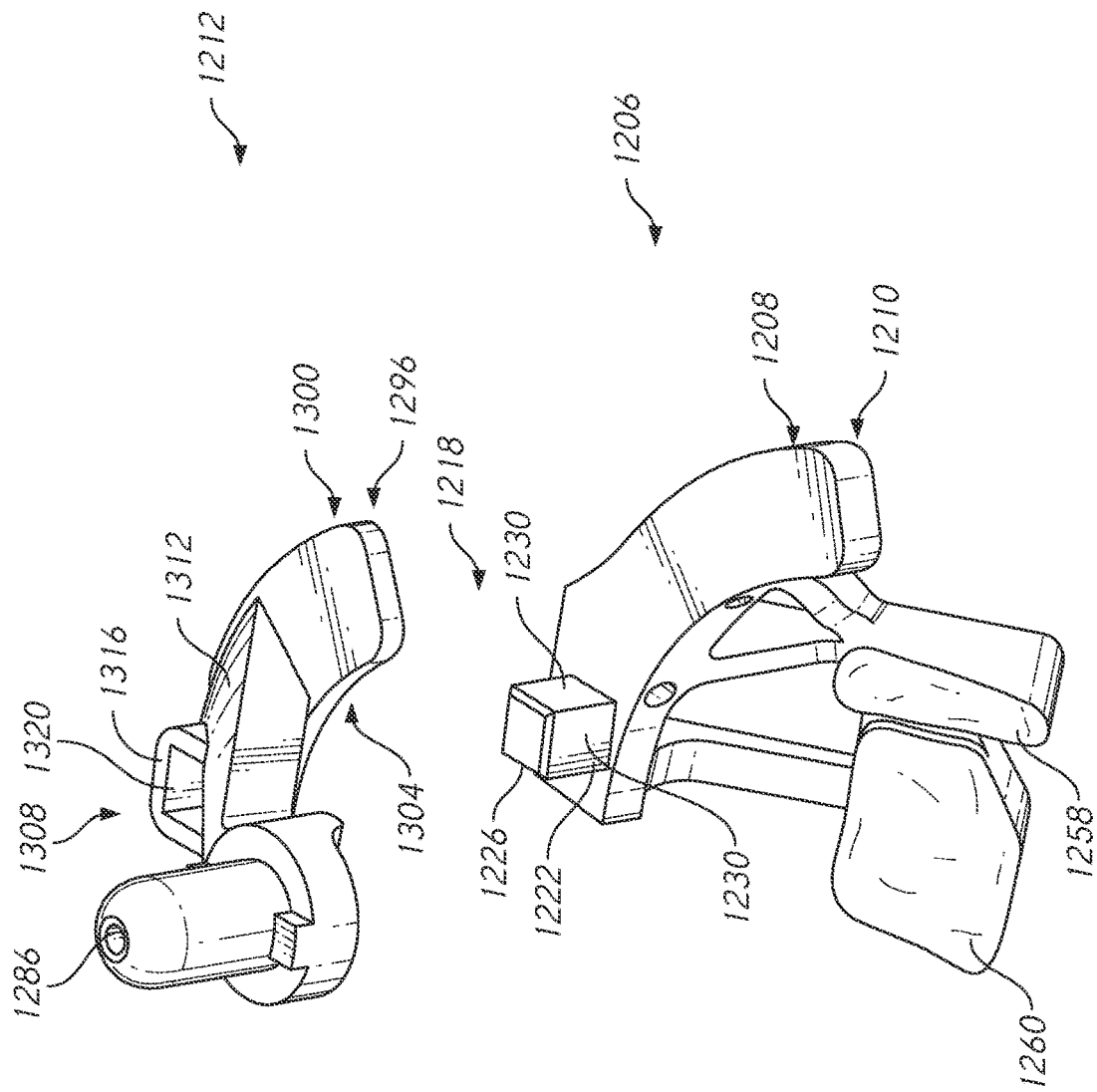
FIG. 36 is an exploded view of the humeral guide of FIG. 34.

The connection mechanism 1214 includes a projection 1218 disposed on the support portion 1206 that is adapted to extend into an aperture 1308 of the positioning jig 1212. FIG. 36 shows that the projection 1218 can have a fixed end 1222 disposed on the first side 1208 of the support portion 1206. The projection 1218 can have a free end 1226 disposed away from the fixed end 1222. The projection 1218 can have a flat side 1230. The free end 1226 can be advanced into an aperture 1308 formed on the positioning jig 1212. The flat side 1230 can be mated against a corresponding flat side 1320 of the aperture 1308, as discussed further below.

The support portion 1206 has a second projection 1248 disposed on the second side 1210 of the support portion 1206. The projection 1248 extends from the second side 1210 in a direction away from the first side 1208. The projection 1248 have a first support member 1250 and a second support member 1252. One or both of the first support member 1250 and the second support member 1252 can be elongate members. The second elongate member 1252 extends down to be disposed at, adjacent to or over a bicipital groove of the patient in use. The first elongate member 1250 extends down to be disposed at adjacent to, or over a portion disposed laterally of the bicipital groove, e.g., at, adjacent to or over the greater tuberosity when the humeral cutting guide 1200 is applied to the humerus 12.

The support portion 1206 can also include a third support member 1254 disposed adjacent to the second member 1252. The third support member 1254 can be an elongate member in some embodiments. The third elongate member 1254 can be configured to enhance the structural integrity of the support portion 1206.

Figure 33:
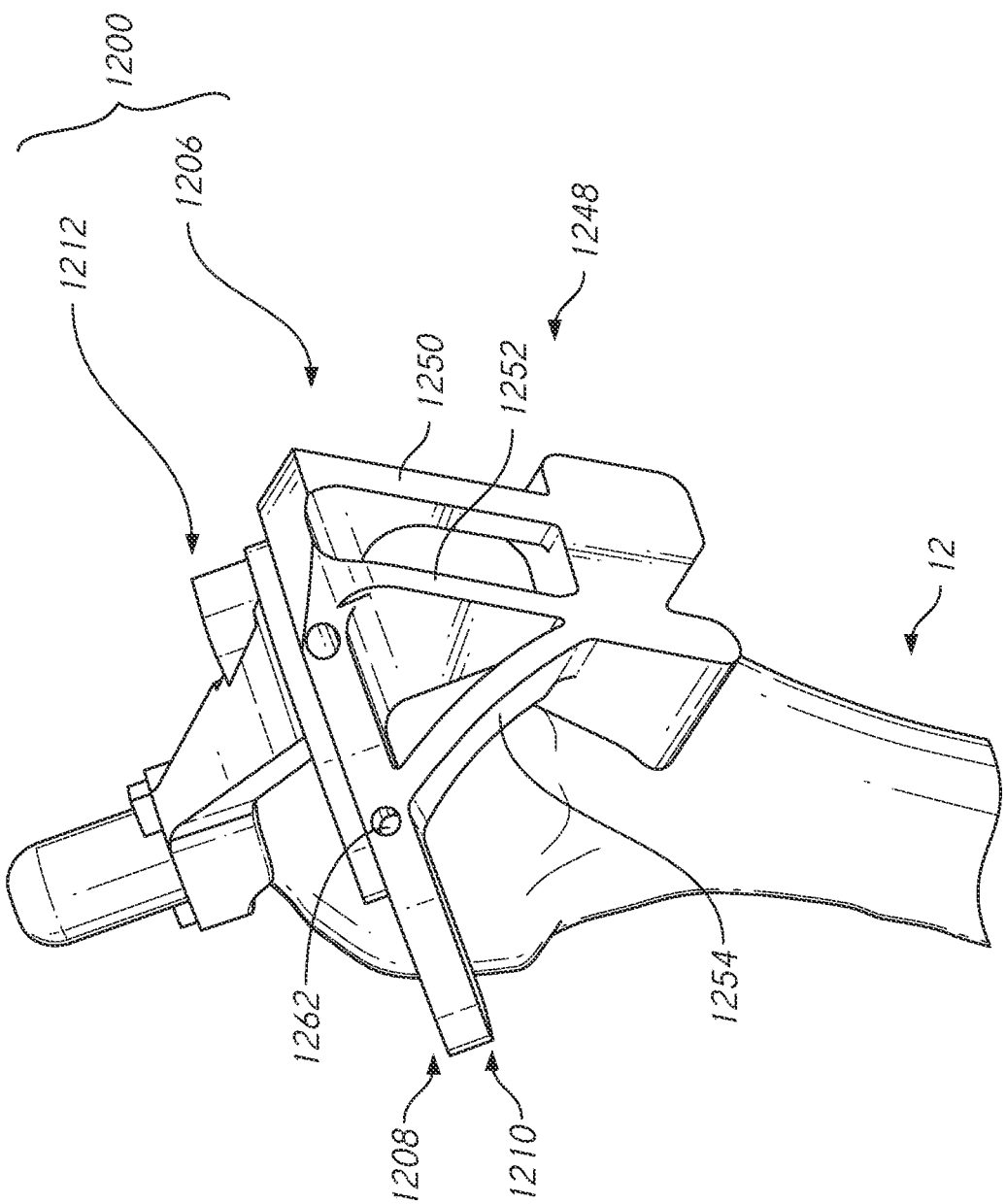
Figure 34:
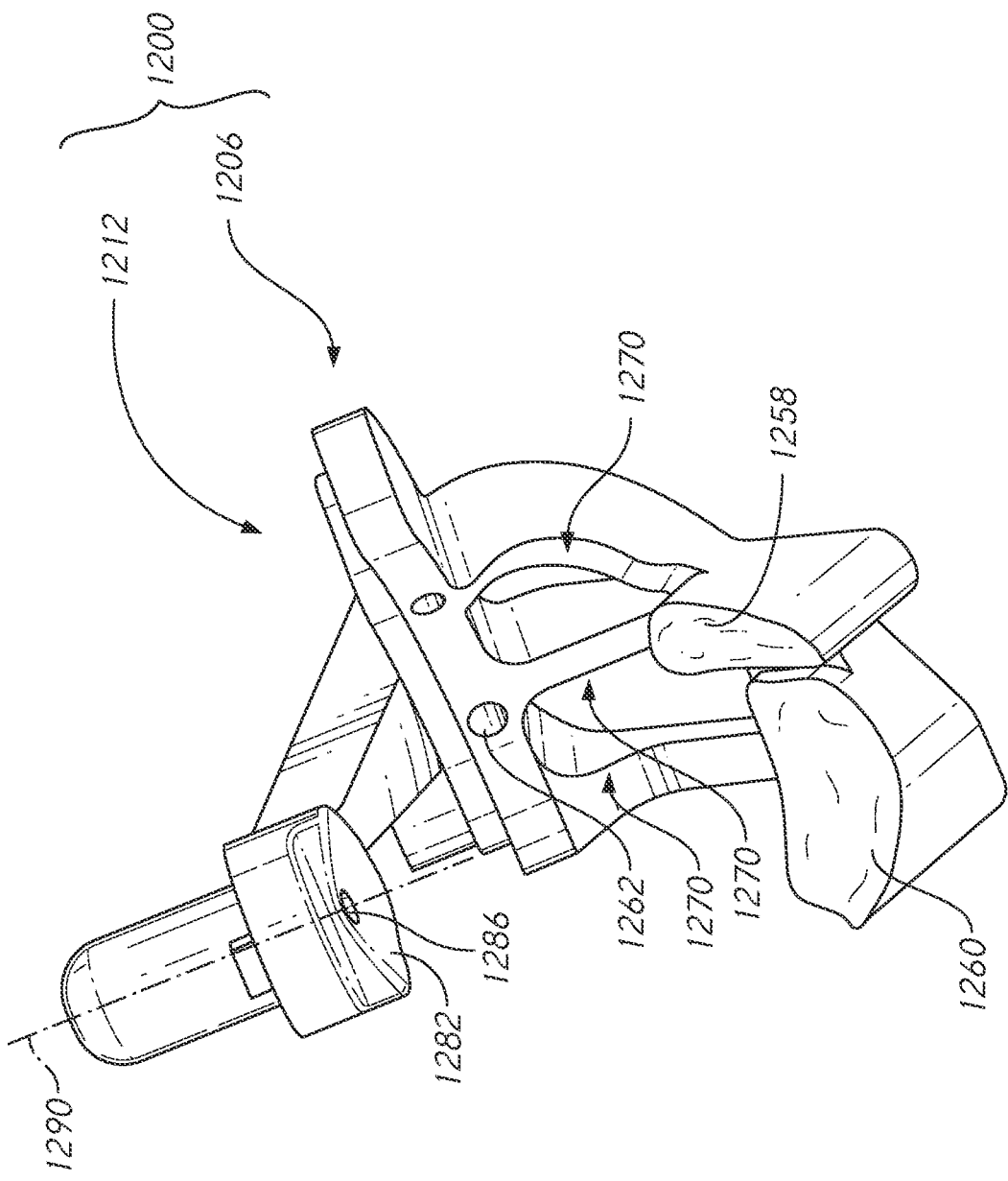
FIG. 34 is a perspective view of a side of the humeral cutting guide having contact areas configured to contact anatomy of the humerus on and distal to the humeral head portion.
Figure 35:
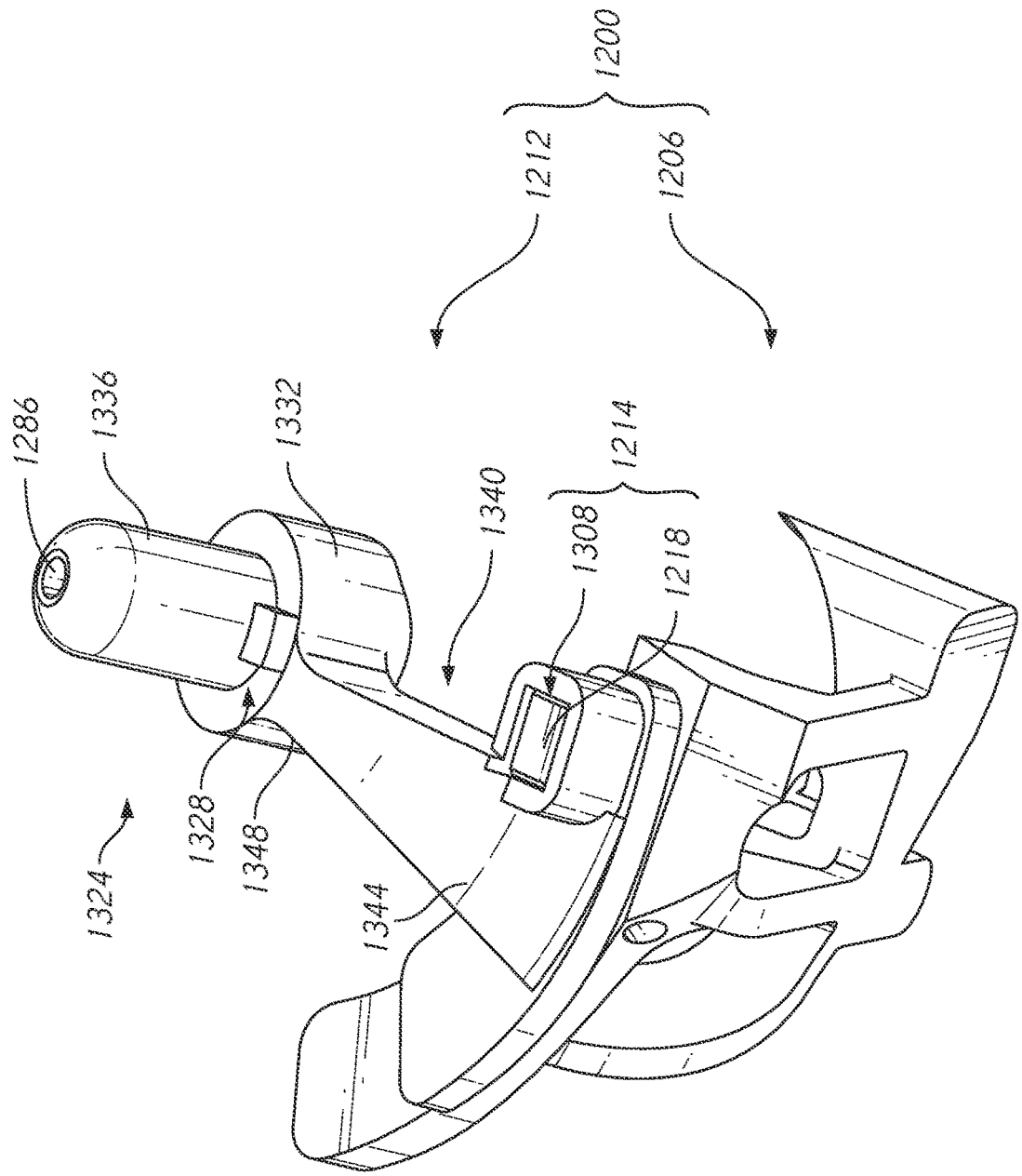
FIG. 35 is a perspective view of a side of the humeral guide opposite to the side illustrated in FIG. 34.

FIGS. 33 and 34 show that opposite the support members 1250, 1252, 1254, the support portion 1206 can include one or more contact area(s) 1256. The contact areas or area 1256 has at least a portion that is a substantial negative of a corresponding bone portion of the specific patient. The contact area 1256 can include a first portion 1258. The first portion 1258 can be configured to be complementary to a bicipital groove of the humerus. The first portion 1258 can be supported by one or both of the second elongate member 1252 and/or the third elongate member 1254. The contact area 1256 can include a second portion 1260 configured to be complementary to a portion of the humerus distal to an anatomical neck of the humerus of the specific patient, e.g., spaced apart from the bicipital groove. The second portion 1260 can be matched to a surface of the greater tuberosity of the patient.

FIG. 34 shows a medial surface 1270 of the support portion 1206 is configured to arch away from first portion 1258 and the second portion 1260 of the contact area 1256. Such arched configuration enables the first elongate member 1250, second elongate member 1252, and/or the third elongate member 1254 to be spaced away from the bone when the support portion 1206 is applied to the humerus 12. The arch or arched configuration provides a gap 1272 between the support portion 1206 and anatomy of and around the humerus 12. The gap 1272 allow soft tissue attachments to the humerus 12 to be accommodated under the support portion 1206 when the second portion 1260 is applied to the humerus 12 and the contact area 1256 is in contact with the intended portions of the humerus 12. This configuration provides several advantages. First, the support portion 1206 can be more quickly and easily connected to the humerus 12. Also, the connection to the humerus 12 can be more confidently confirmed because soft tissue will not obstruct the connection. Further if the support portion 1206 is not configured to accommodate the soft tissue, the procedure will be more complicated, requiring removal of soft tissue prior to proper seating of the support portion 1206.

FIG. 32 shows that the humeral cutting guide 1200 can have a plurality of mounting pin holes 1262. The plurality of mounting pin holes 1262 can each have a longitudinal axis 1268, which axes can be disposed along diverging paths 1264. The plurality of mounting pin holes 1262 can enable stabilization pins 1018 to be advanced through the support portion 1206 into the humerus 12.

FIG. 34 shows that the humeral cutting guide 1200 can have a contact area 1282 disposed on the positioning jig 1212. The contact area 1282 is configured to be matched to the specific anatomy of the head 10 of the humerus 12 of the patient. The positioning jig 1212 can have a base 1292 that has a first side 1296 and a second side 1300. The base 1292 can be configured to avoid soft tissue attachments in the same manner as the support portion 1206. For example, if soft tissues may be located where the base 1292 would be positioned adjacent to the humerus 12 the base 1292 can have a base gap area 1304. The base gap area 1304 is an area that is spaced away from the surface of the humerus 12 by an amount sufficient to allow the soft tissue that may be located superior to but between the bicipital groove and the greater tuberosity to be left in place without significant or any compression when the humeral cutting guide 1200 is applied.

As discussed above, the positioning jig 1212 has an aperture 1308 that can receive the projection 1218 of the support portion 1206. The aperture 1308 can extend upward from a second end 1316 of the base 1292 opposite a first side 1296. The first side 1296 is configured to engage the first side 1208 of the support portion 1206 when the positioning jig 1212 is coupled with the support portion 1206. The aperture 1308 can extend between a first end 1312 at the first side 1296 to a second end 1316 disposed above the second side 1300. The aperture 1308 can have a flat side 1320 formed therein configured to mate with the flat side 1230 of the projection 1218 discussed above. In one embodiment, the projection 1218 comprises a square cross-section parallelepiped extending away from the first side 1208. The aperture 1308 is a square cross-section lumen extending away from the second side 1300 of the base 1292. The projection 1218 and the aperture 1308 can be configured for a slip fit such that the surgeon can advance the aperture 1308 over the projection 1218 after the support portion 1206 is secured to the humerus 12 without requiring any tool or any significant force. This configuration also enables quick release of the positioning jig 1212 from the support portion 1206 by slip fit.

The positioning jig 1212 has a boss 1324 that is suspended from the base 1292 at a position over the head 10 of the humerus 12 when the humeral cutting guide 1200 is assembled over and on the humerus 12. The boss 1324 can have a first portion 1332 and a second portion 1336. The first portion 1332 can be coupled with a projection 1340 that extends from a first end 1344 coupled with the second end 1316 of the base 1292 to a second end 1348. The first portion 1332 can be coupled with the second end 1348 of the projection 1340. The second portion 1336 can be disposed above the first portion 1332. An annular ledge can be disposed between the first portion 1332 and the second portion 1336. The second portion 1336 can extend from the first portion 1332 to a free end of the boss 1324. The aperture 1286 can be disposed through the boss 1324 from the free end of the second portion 1336 of the boss 1324 to an opposite end of the first portion 1332.

A surface of the boss 1324 opposite the opening aperture 1286 can be patient matched, e.g., a substantial negative of a portion of the head 10 to which the positioning jig 1212 will contact when assembled to the support portion 1206 on the humerus 12. The contact area 1282 engaged with the head 10 of the humerus 12 can be disposed at or around an aperture 1286. In various embodiments, the humeral cutting guide 1200 provides patient specific contact at three spaced apparat locations, e.g., at the bicipital groove, the greater tuberosity, and the head 10 of the humerus 12. This contact is advantageously provided while at the same time that the gap 1272 can accommodate soft tissues that may be disposed between the medial surface 1270 and the humerus 12.

The second end 1348 of the projection 1340 can be coupled with a side surface of the boss 1324. In one embodiment, the distal-proximal thickness or dimension of second end 1348 of the projection 1340 can be the same as the distal-proximal thickness or dimension of first portion 1332 of the boss 1324 providing a rigid connection therebetween. The first end 1344 of the projection 1340 is wider in a direction corresponding to the longitudinal axis of the base 1292 than the second end 1348. The enhanced width near the base 1292 enables the projection 1340 to form a rigid construction with the base 1292 such that unwanted deflection or deformation of the positioning jig 1212 can be reduced, minimized or eliminated.

Figure 37A:
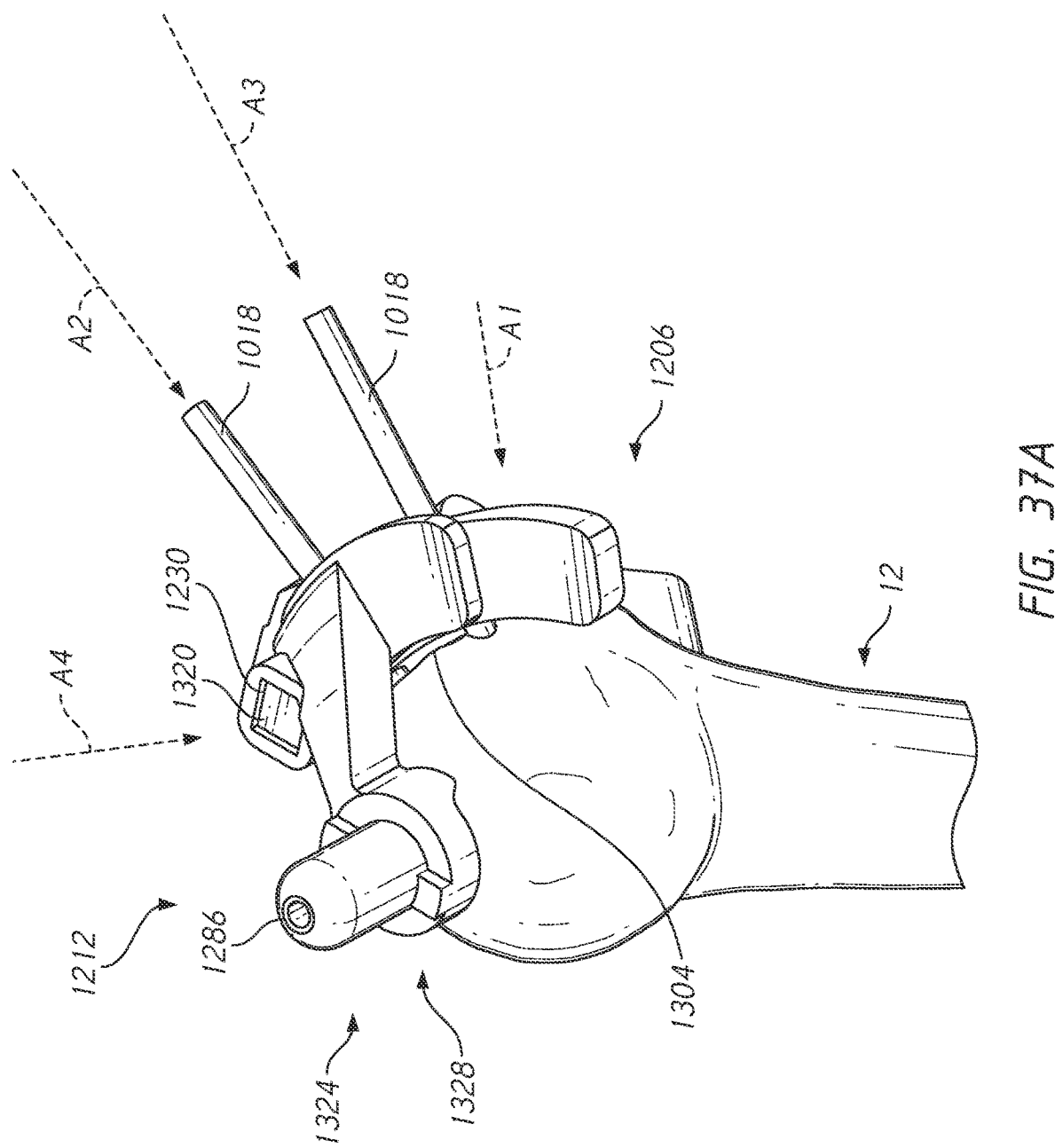
FIGS. 37A-37G illustrate various stages of a method of using the humeral guide of FIG. 32-36 to prepare the humerus for implanting a humeral anchor.

FIGS. 37A-37G illustrate various methods that can be performed using the humeral cutting guide 1200 to surgically modify and prepare the humerus 12 for a shoulder prosthesis. Prior to that portions of the method illustrated in FIG. 37A the shoulder would be accessed by forming an incision in the skin. Thereafter, the humerus 12 would be exposed and accessed. The approach that would be a lateral and/or a posterior approach. In other words, the incision that would be formed would be made on the side of the arm and/or toward the back of the patient. Access to the incision may be enhanced by use of distractors or other spreader devices. After the humerus 12 is accessible in the incision the support portion 1206 is advanced toward the humerus 12 as indicated by the arrow A1. If the position of the support portion 1206 is confirmed, the support portion 1206 can be immobilized on the humerus 12. For example, a first stabilization pin 1018 can be advanced according to the arrow A2 through the one of the apertures or holes of the plurality of mounting pin holes 1262. Then, a second stabilization pin 1018 can be advanced through another hole of the plurality of mounting pin holes 1262 according to the arrow A3. FIG. 37A shows that in the method the stabilization pins 1018 are advanced along divergent, convergent, or non-parallel directions. After the stabilization pins 1018 are fully advanced, the support portion 1206 is immobilized on the humerus 12. When so placed, the medial surface 1270 can be disposed around soft tissue attachments to the humerus 12. The soft tissues can be accommodated between the humerus 12 and the bone facing aspects of the first elongate member 1250, the second elongate member 1252, and the third elongate member 1254.

In one method, after the support portion 1206 is fixed to the humerus 12 the positioning jig 1212 can be coupled with the support portion 1206. The positioning jig 1212 can be coupled by rotationally aligning the boss 1324 over the head 10 of the humerus 12 and further rotationally aligning the flat side 1320 of the aperture 1308 with the flat side 1230 of the projection 1218. Upon such alignment, the positioning jig 1212 can be advanced according to the arrow A4 toward the support portion 1206 until the first side 1296 of the base 1292 comes to rest on the first side 1208 of the support portion 1206. When in such position the base gap area 1304 also can accommodate any soft tissue attachment that may be in the vicinity of the base 1292. The steps can be performed in other orders. For example, the motion according to the arrow A4 can come before the placement of the stabilization pins 1018 according to the arrow A2 and arrow A3.

Figure 37B:
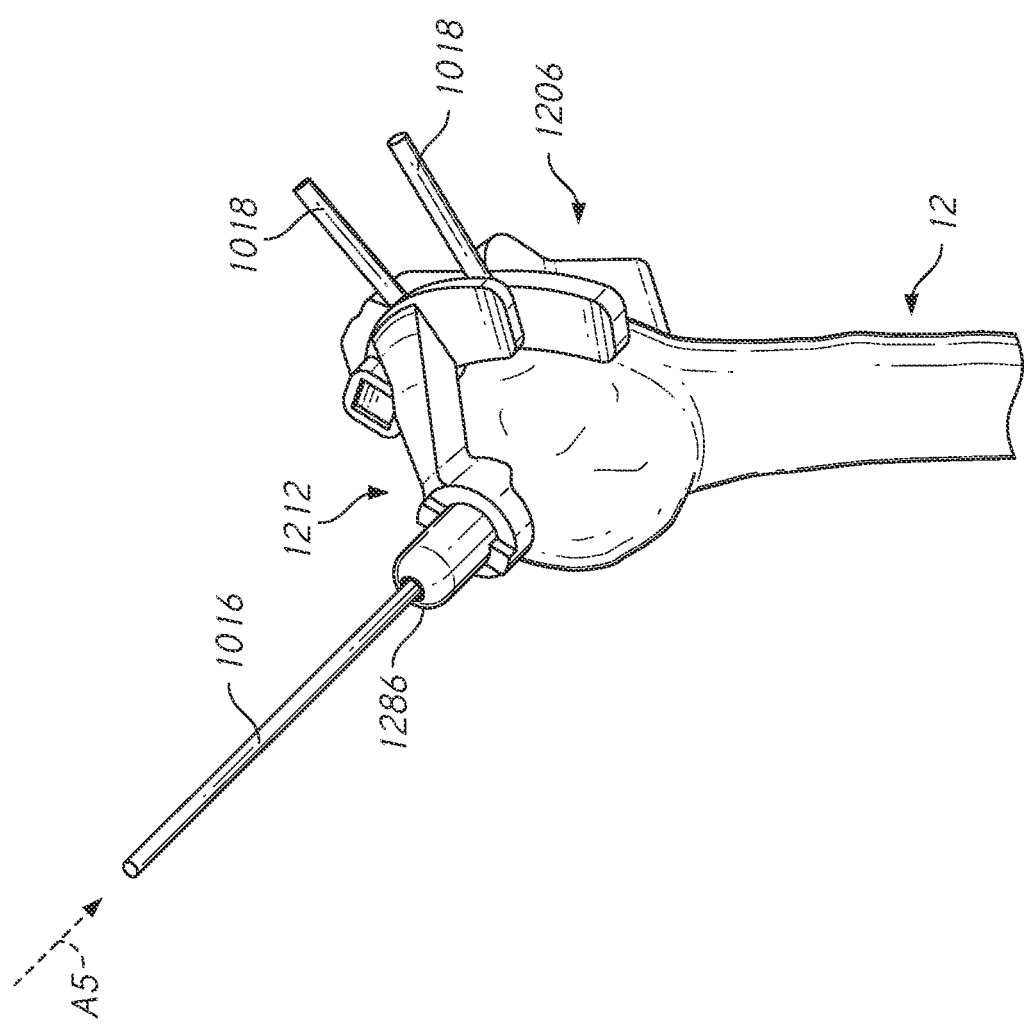

FIG. 37B shows that in one embodiment, the guide pin 1016 can be placed through the aperture 1286 prior to resection of the head 10 according to the arrow A5. The placement of the guide pin 1016 can form a pin channel in the head 10 or in the humerus 12 distal the head 10. The guide pin 1016 can be removed in a direction opposite the arrow A5 so that the humerus 12 can be further prepared using the humeral cutting guide 1200.

Figure 37C:
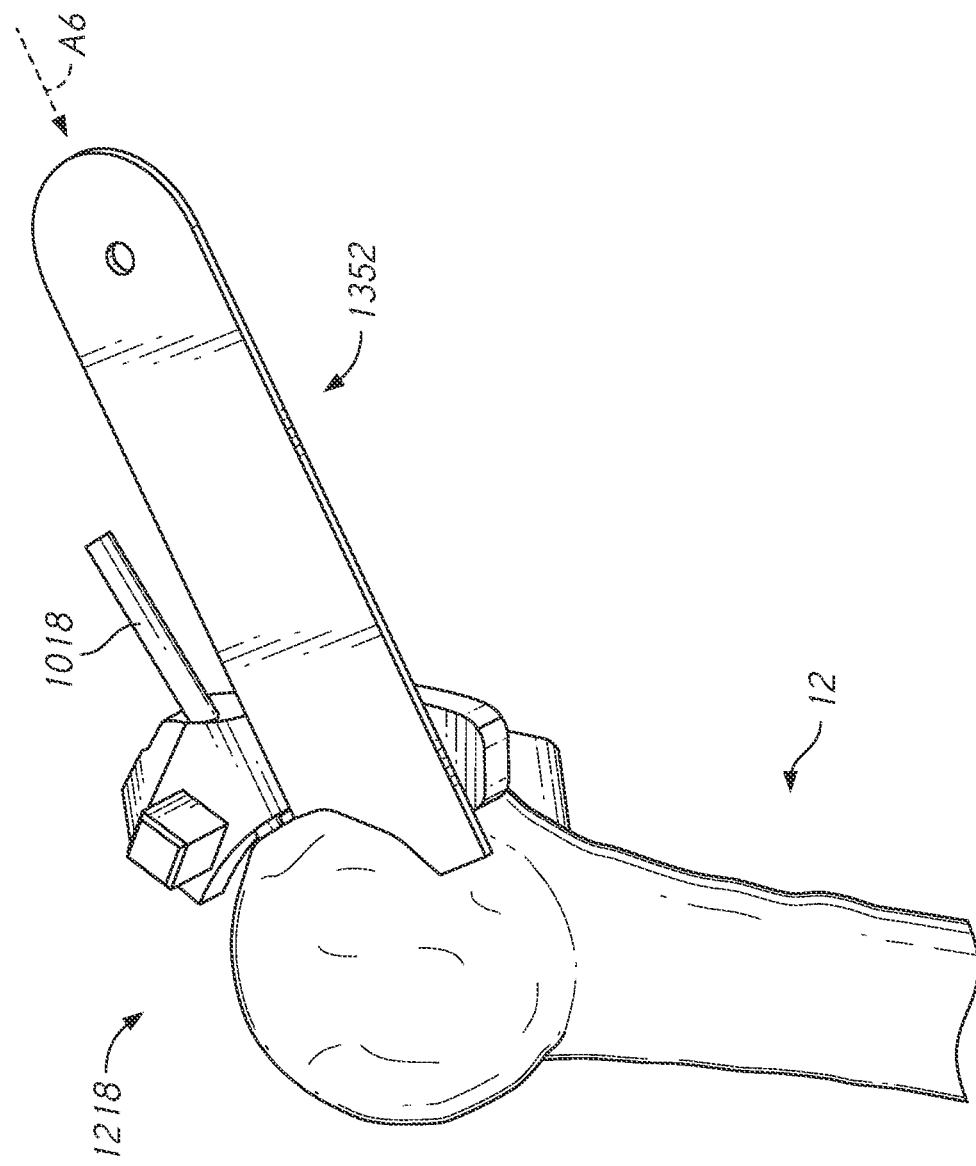

FIG. 37C shows that in one method, the positioning jig 1212 can be removed from the support portion 1206 and thereafter, a saw 1352 can be advanced according to an arrow A6 along the first side 1208, e.g., along the resection surface 1204 to resect the head 10 and remove the head from the humerus 12. FIG. 37C show that the support portion 1206 advantageously exposes a lateral side of the first side 1208 for resection while the projection 1218 remains available for subsequent mounting of positioning jigs, as discussed below.

Figure 37D:
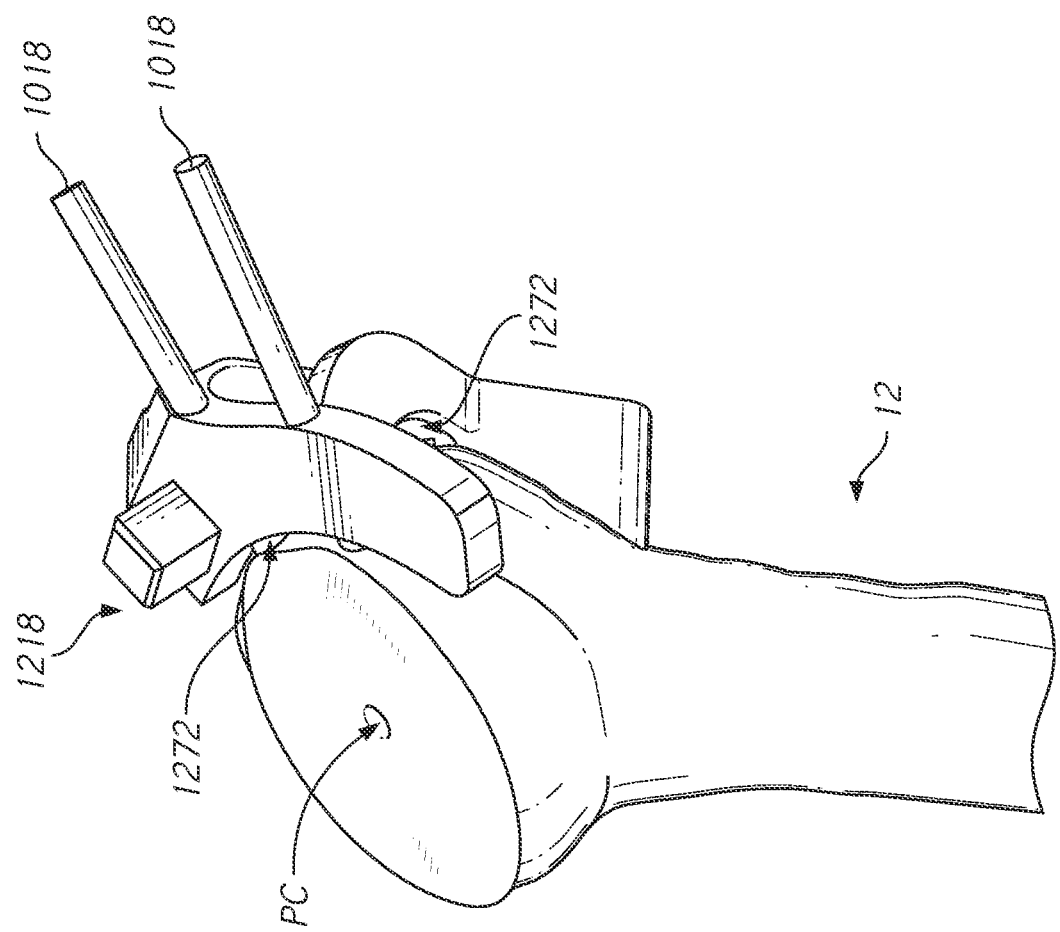

FIG. 37D shows that after the resection has been completed the resected head is separated from the surgical field. If the advancement of the guide pin 1016 according to the arrow A5 was sufficient, a pin channel PC can be already provided and available in the resected surface.

Figure 37E:
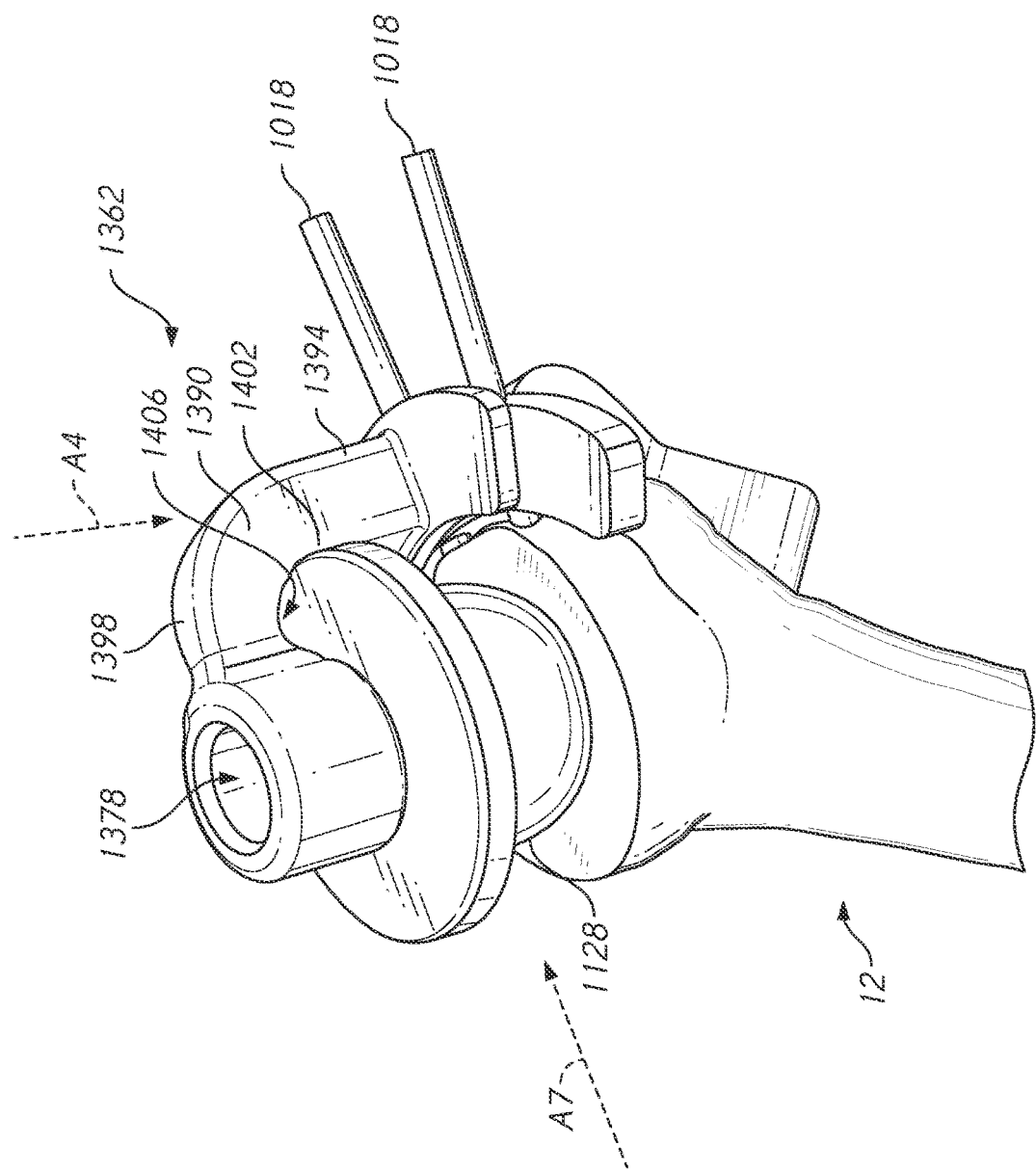

FIG. 37E shows a further aspect of certain methods in which a releasable positioning jig 1362 for guiding a reamer is coupled with the support portion 1206. The releasable positioning jig 1362 includes a base 1366 having a first side 1370 configured to mate with the first side 1208 of the support portion 1206 and a second side 1374 opposite the first side 1370. The second side 1374 has an aperture 1308 similar to that of the support portion 1206. The releasable positioning jig 1362 has an aperture 1378 disposed opposite to the base 1366 and coupled thereto by a projection 1390. The aperture 1378 has a first end 1394 facing away from the base 1366 and a second end 1398 facing the base 1366. The aperture 1378 is configured to receive and guide a shaft 1124 of a reamer as discussed below.

The aperture 1378 disposed at a free end of a projection 1390 of the releasable positioning jig 1362. The projection 1390 has a first end 1394 disposed adjacent to the base 1366 and a second end 1398 spaced away from the base 1366. The aperture 1378 is located adjacent to the second end 1398. The projection 1390 has an inner surface 1402 that faces toward the resected humerus 12 when the releasable positioning jig 1362 is mounted to the support portion 1206 following resection. The inner surface 1402 forms a reamer clearance 1406 that is sized to enable a reamer head 1128 to be rotated beneath the projection 1390 without contact therebetween.

FIG. 37E illustrates a portion of a method in which the reamer head 1128 is advanced according to the arrow A7 into a space between the projection 1390 and the resected humerus 12 such that the reamer head 1128 is within the reamer clearance 1406.

Figure 37F:
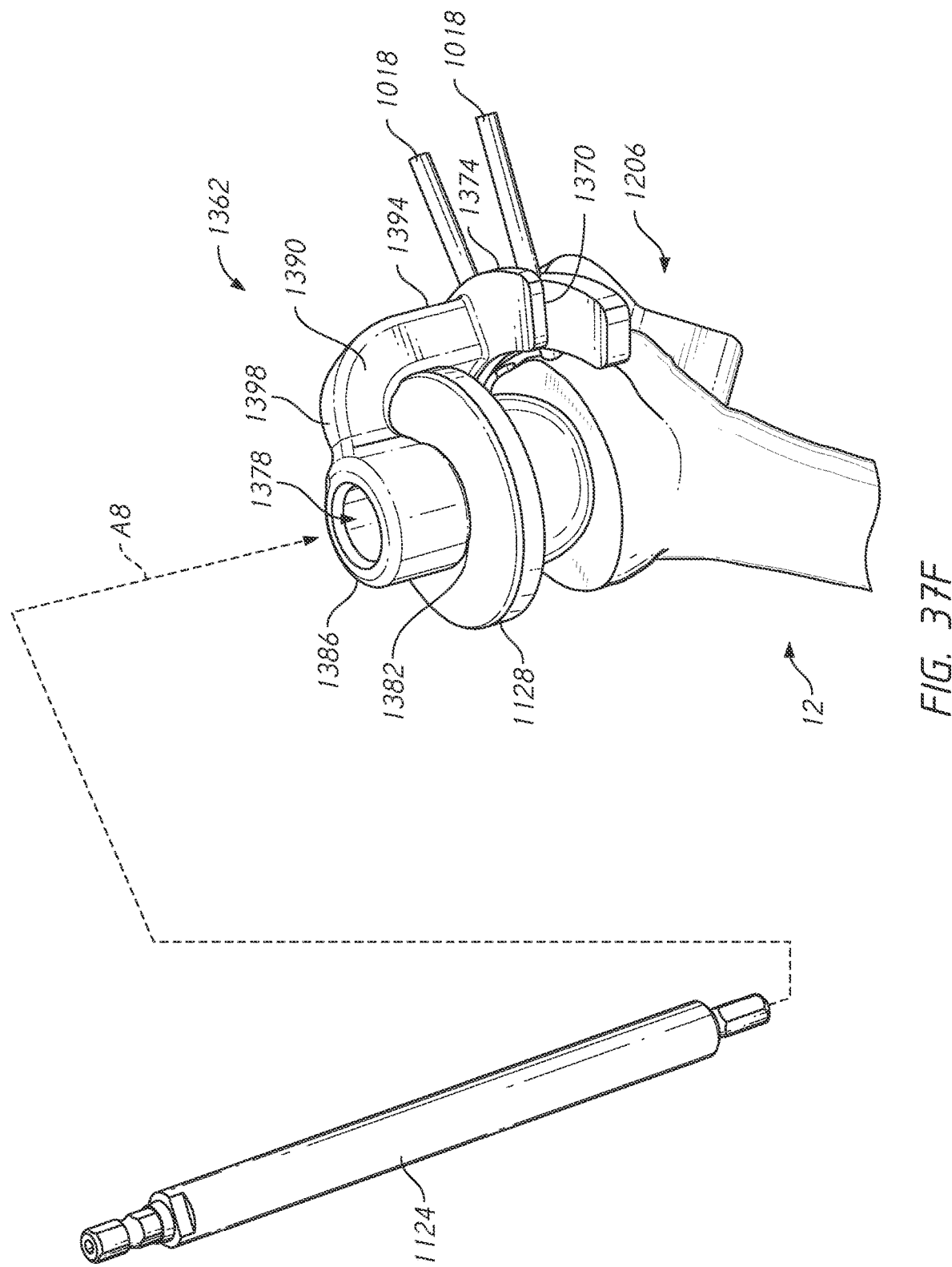
Figure 37G:
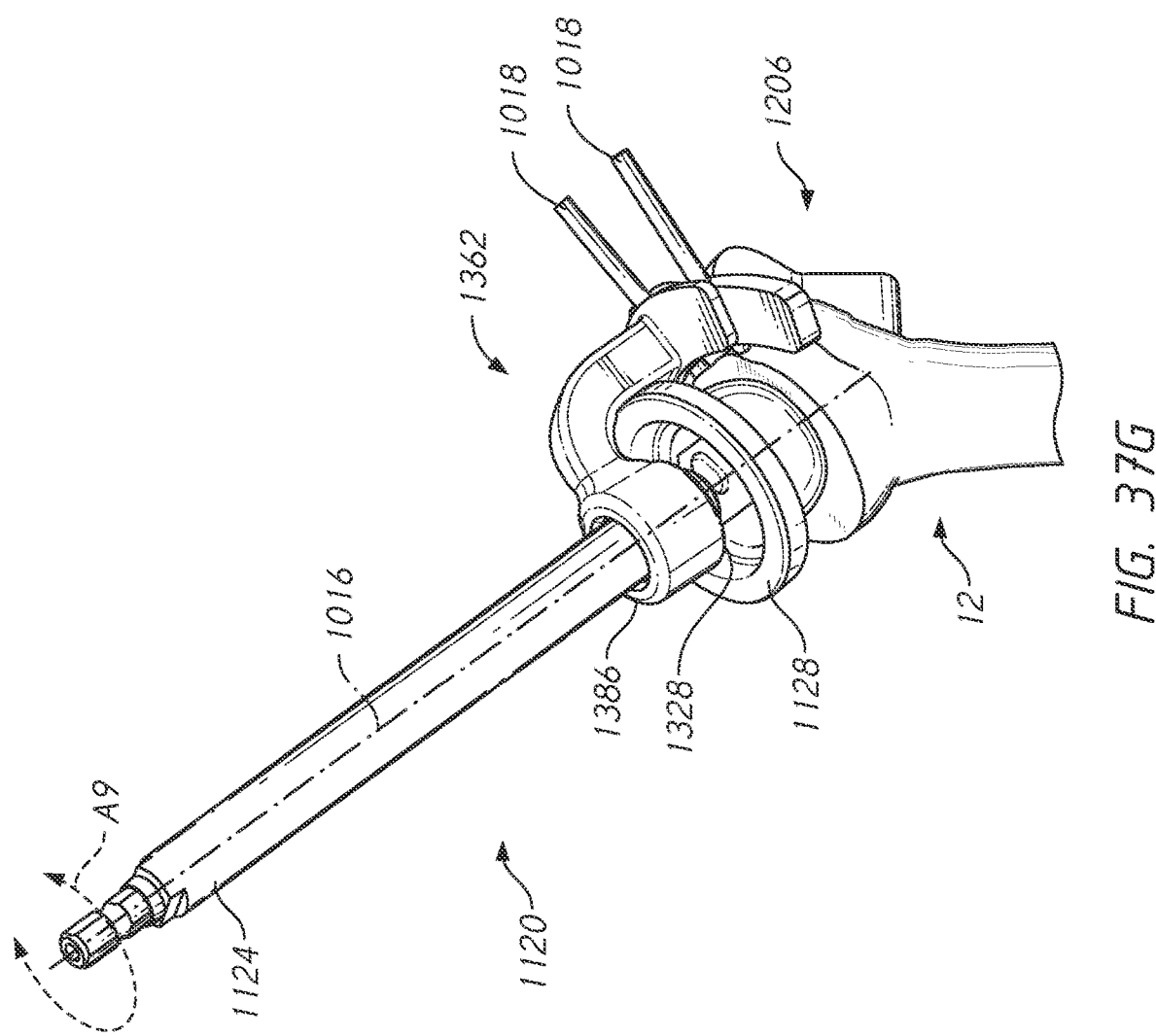

FIG. 37F shows a further step in which a distal end of the shaft 1124 is inserted into the second end 1386 of the aperture 1378 of the releasable positioning jig 1362 and through the aperture out the first end 1382 into engagement with a tooling interface (not shown) of the reamer head 1128. FIG. 37F shows that the insertion of the shaft 1124 can be unguided by a guide pin 1016. Rather the releasable positioning jig 1362 disposed about the aperture 1378 can guide the shaft 1124 into position on the resected surface of the humerus 12. FIG. 37G show that according to the arrow A9 the positioning jig 1362 can guide the rotation of the reamer head 1128 into the bone beneath the resected surface of the humerus 12. FIG. 37G also show the guide pin 1016 has been placed through a lumen of the shaft 1124. Thus, the reaming as in FIG. 37G is optionally performed over a pin.

It will be appreciated that the humeral cutting guide 1000 and the humeral cutting guide 1200 described above provides excellent initial connection to the bone, or feel. Also, the releasable positioning jig 1012 and the positioning jig 1212 enable the surgeon to benefit from the function of the aperture 1072 or the aperture 1286 for positioning a guide pin 1016 or other instrument without requiring the releasable positioning jigs to be present for other parts of the procedure. The monolithic member mounting pin holes 1036 and mounting pin holes 1262 allow excellent stability on the side surface of the humerus 12. Providing a contact area 1020 in multiple areas disposed about the humerus 12 at one proximal-distal position reduces, minimizes or eliminates rocking about a longitudinal axis prior to placement of the stabilization pins 1018. Similarly the first portion 1258 and second portion 1260 provide proximally-distally aligned contact with anatomical locations that enhance the initial connection. Providing contact areas in multiple areas spaced apart along the proximal-distal position (as in FIG. 28) reduces, minimizes or eliminates rocking about a transverse axis prior to placement of the stabilization pins 1018. The separability of the positioning jigs also allows the jigs to be better adapted to their function. The releasable positioning jig 1012 and the positioning jig 1212 can be well adapted to the guide pin 1016. Other positioning jigs, such as the releasable positioning jig 1362, can be adapted for other purposes, such as for guiding reaming, as discussed below in connection with FIGS. 37E-36G. Also, the resection surface 1004 and that of the support portion 1206 can be adapted to provide a visual cue during the preparation of the bone beneath the resection.

b. Guides with Enhanced Access Configurations and with Lateral or Anterior Approach FIGS. 38-48 shows a humeral cutting guide 1500. The guide 1500 is similar in some respects to the guides 1000 and 1200 discussed above and provides some of the same advantages and some additional advantages, as discussed below. Differences between the guides 1000 and 1200 and the guide 1500 are discussed below. The description of the guides 1000, 1200 may supplement the description of the guide 1500 where similar. As discussed further below, the humeral cutting guide 1500 can be configured for an anterior and/or lateral approach to the humerus. For example, as discussed further below, the guide 1500 can be configured for patient specific or patient matched contact with anatomy accessible from an anterior or lateral approach. The guide humeral cutting guide 1500 could be configured for posterior or another approach. The guide 1500 can have a plurality of contact areas. The guide 1500 can have a contact area configured to contact the bicipital groove. The guide 1500 can have a contact area configured to contact a bone at and/or between the medial calcar and the bicipital groove. In one form the guide 1500 has a support portion 1506 and a positioning jig 1512 and can be configured for patient specific contact with the humeral head as well.

Figure 38:
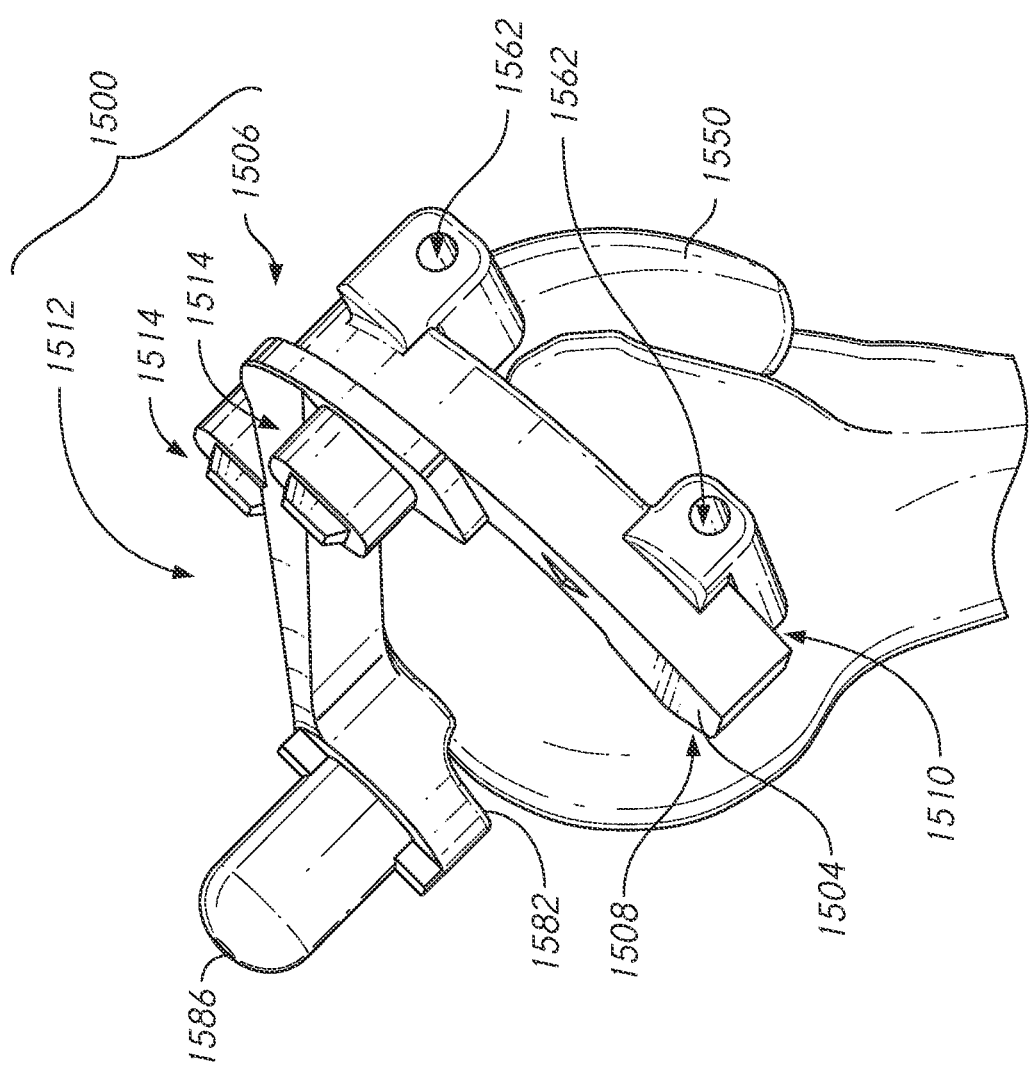
FIG. 38 shows a humeral cutting guide according to another embodiment, the guide being illustrated disposed on a surface of and in contact with preoperatively planned contact portions of a head portion of the humerus.

FIG. 38 shows that the humeral cutting guide 1500 has a connection mechanism 1514 that enables the positioning jig 1512 to be releasably attached to the support portion 1506. The support portion 1506 is a jig wherein a resection surface 1504 and portions for patient matched contact and support on the bone are formed as portions of a monolithic member. The connection mechanism 1514 is shown more clearly in component parts in FIGS. 39-41. In particular, the connection mechanism 1514 includes a first projection 1518 and a second projection 1520 that both extend away from a free end coupled with a first side 1508 of the support portion 1506 to a free end disposed away from the first side 1508. The connection mechanism 1514 also includes a first aperture 1604 and a second aperture 1608. The apertures 16041608 are configured to receive the projections 1518, 1520. In that sense the connection mechanism 1514 is configured to operate in a manner similar to the connection mechanism 1214. However, providing two projections and two apertures can provide greater connection security and a symmetrical resistance to deflection when the positioning jig 1512 is coupled to the support portion 1506.

A surgical cue 1509 is also formed on the support portion 1506, e.g., on the first side 1508. The surgical cue 1509 can be used to assist the surgeon in further aspects of a method of preparing the humerus 12 as discussed further below.

Figure 39:
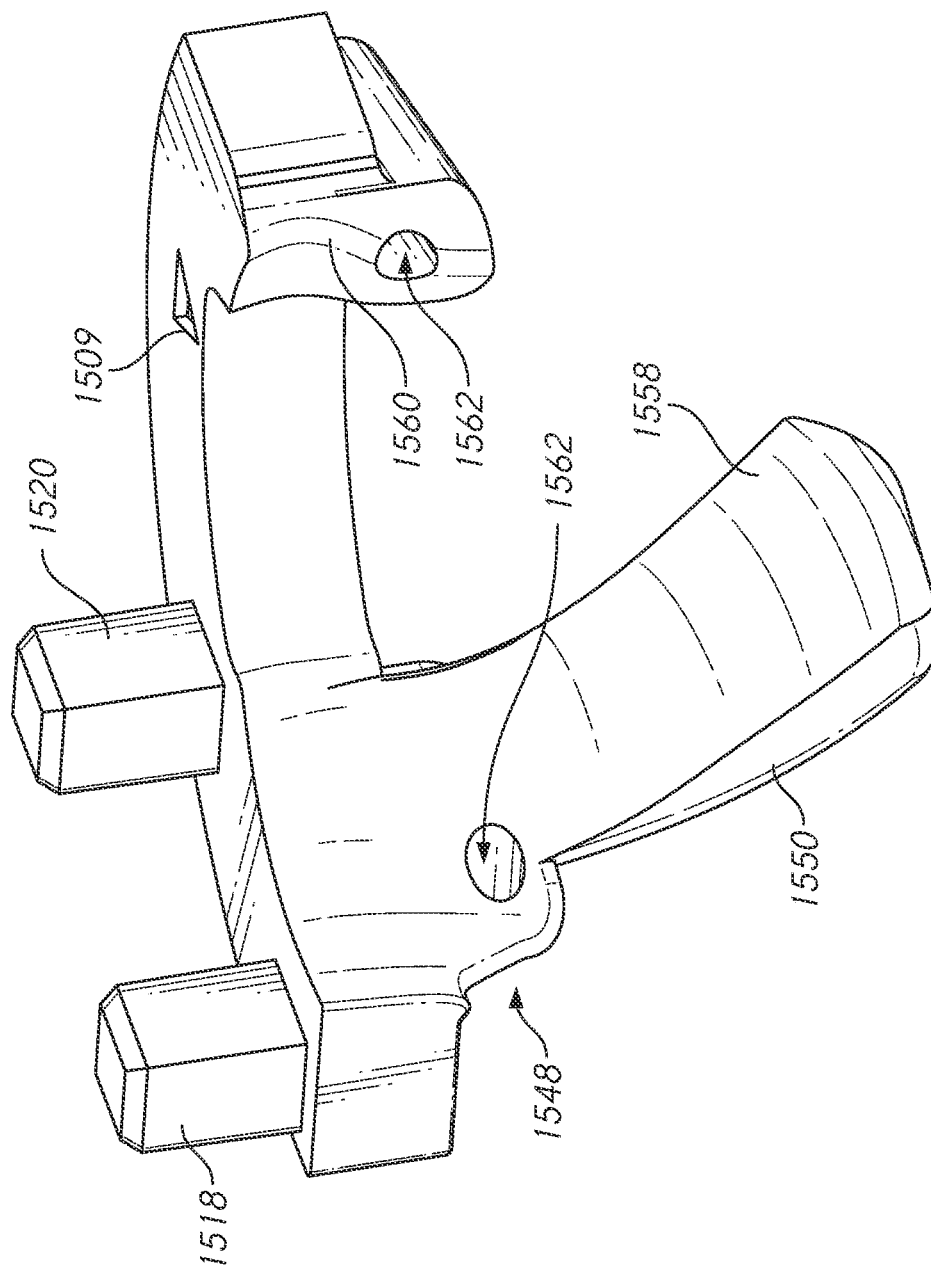
FIG. 39 is a perspective view of a side of a support portion of the cutting guide shown in FIG. 38.

FIG. 39 shows that the second side 1510 of the support portion 1506 has a projection 1548 that is provided for anatomical matching and for supporting the support portion 1506 against the humerus 12. The projection 1548 includes an elongate member 1550 that extends from a fixed end coupled and/or adjacent to the second side 1510 to a free end disposed away from the second side 1510. The projection 1548 includes a contact area 1556. At least a portion of the at least one of the support portion 1506 and the releasable positioning jig 1512 is patient matched and/or comprises a substantial negative of a corresponding portion of the humerus 12 of the specific patient. The elongate member 1550 includes a bone facing side. The bone facing side can include a first portion 1558 configured to be complementary to a lateral portion of the bone, e.g., to a bicipital groove of the humerus 12. The contact area 1556 can include a second portion 1560 configured to be complementary to a second lateral portion of the humerus 12. The first and second lateral portions can be distal to an anatomical neck of the humerus 12 of the specific patient. The second portion 1560 can be spaced apart from the bicipital groove in a lateral, anterolateral or anterior position. The second portion 1560 can be configured to engage a bone portion adjacent to a medial calcar of the humerus 12. FIG. 39 shows that a portion of the bone facing side of the support portion 1506 between the first portion 1558 and the second portion 1560 can be configured to be out of contact with the bone when the first portion 1558 and the second portion 1560 are seated on the planned contact areas. Thus the support portion 1506 is configured for two spaced apart zones of contact without bone contact therebetween. The support portion 1506 is configured for two spaced apart zones of contact without a gap between the bone facing side of the support portion 1506 and the underlying bone between the contact zones.

FIGS. 38 and 39 show that the support portion 1506 can include a plurality of mounting pin holes 1562. The plurality of mounting pin holes 1562 can be similar to those hereinbefore described, including being disposed along diverging paths. The mounting pin holes 1562 can be disposed along converging paths. The mounting pin holes 1562 can be disposed along non-parallel paths.

Figure 40:
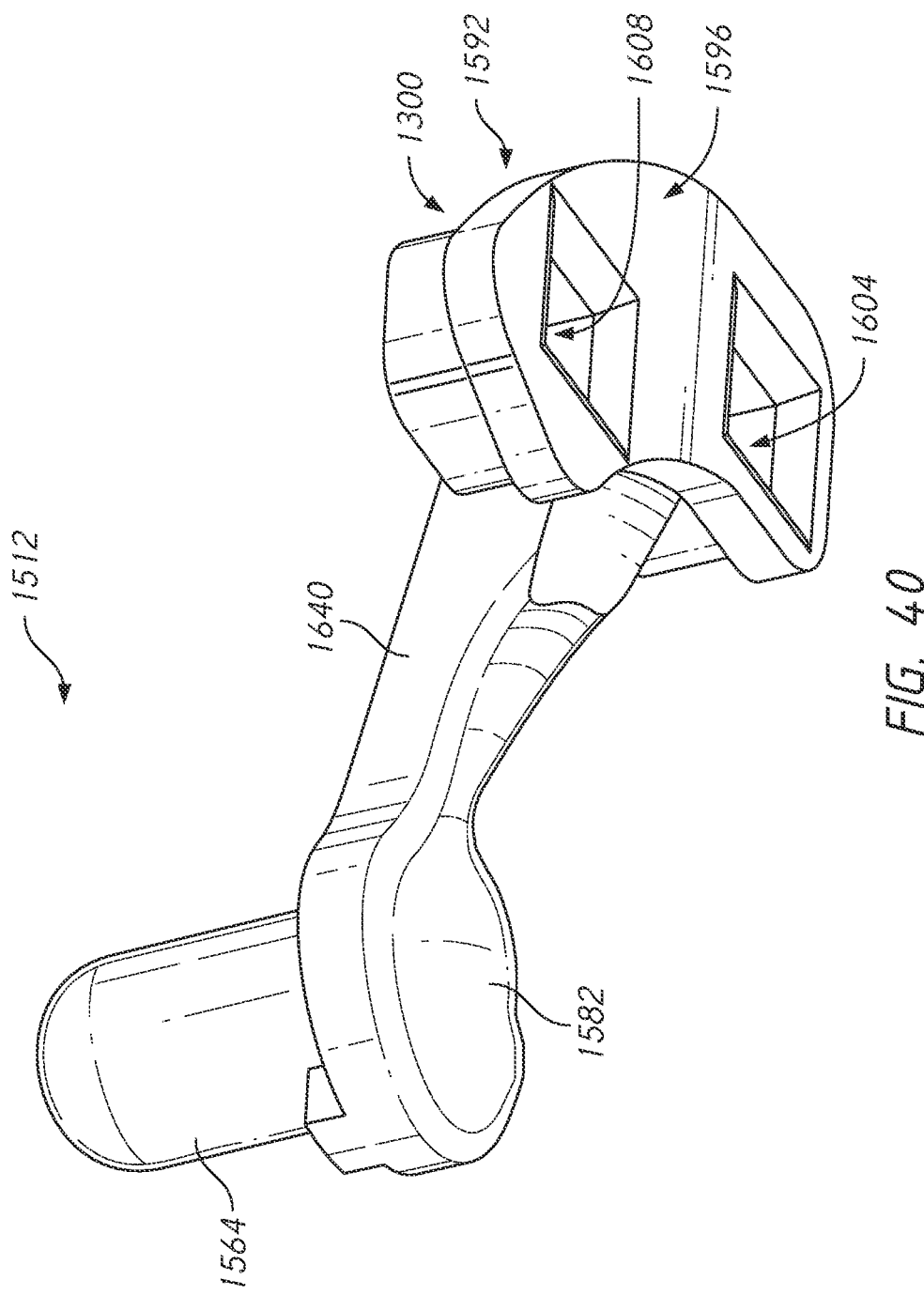
FIGS. 40 and 41 are a perspective and bottom views of a side of a releasable positioning jig of a humeral cutting guide that has a contact area configured to contact anatomy of a head portion of the humerus.
Figure 41:
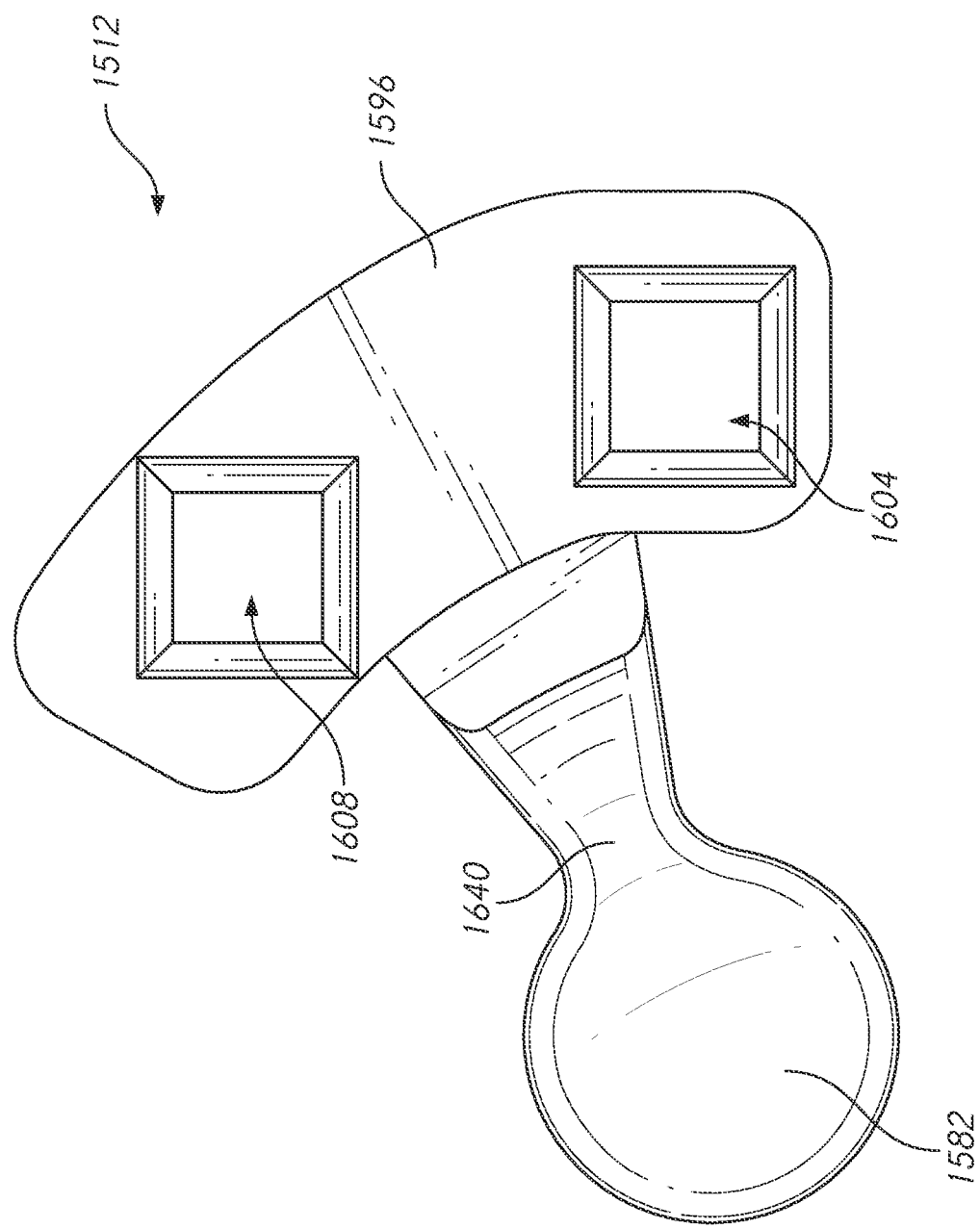
Figure 42:
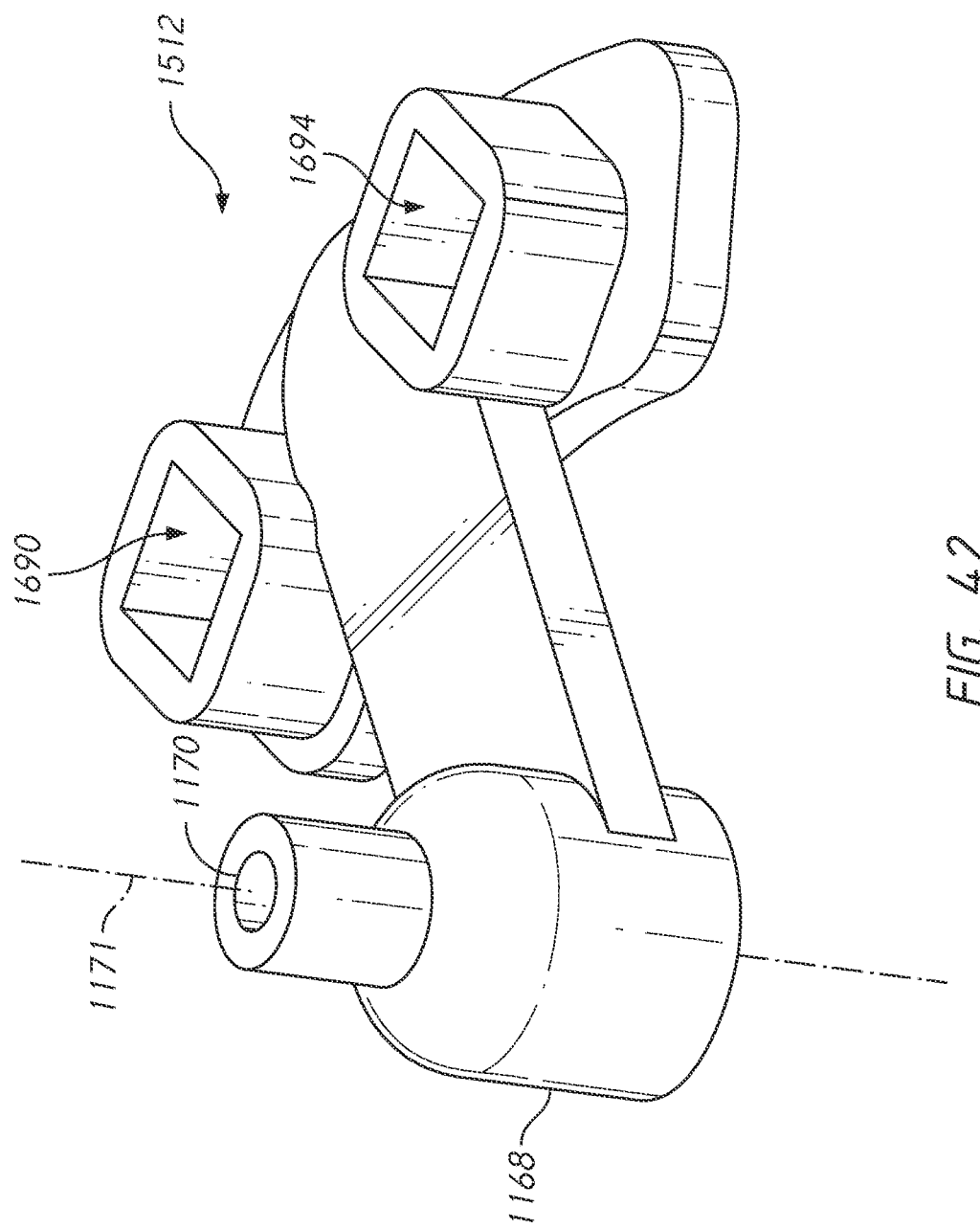
FIG. 42 is a perspective view of another embodiment of a releasable positioning jig that can be coupled with the support portion of FIG. 39 for placement of a guide pin.

FIGS. 40-42 show the releasable positioning jig 1512 and a releasable positioning jig 1662. The releasable positioning jig 1512 is similar to the positioning jig 1212 except as described differently below. The releasable positioning jig 1512 includes a contact area 1582 that is disposed on a bone facing side thereof. The contact area 1582 can be disposed under a boss 1624 of and can extend along a least a portion of a projection 1640 the releasable positioning jig 1512. The contact area 1582 is configured to match a portion of the head 10 of the humerus 12. An aperture for the guide pin 1016 can be formed through the boss 1624. The first aperture 1604 and the second aperture 1608 can include at least one flat surface. The first aperture 1604 and the second aperture 1608 can comprise lumens with square shaped cross-sections. FIG. 41 shows that the first aperture 1604 and the second aperture 1608 can be located on opposite sides of a longitudinal axis of the projection 1640 such that loading on the releasable positioning jig 1512 is evenly distributed and opposed by portions of a base 1592 of the releasable positioning jig 1512, which load can be transferred through interaction of and between the first projection 1518 and the first aperture 1604 and through interactions of and between the second projection 1520 and the second aperture 1608.

FIG. 41 shows that the releasable positioning jig 1662, which is similar to the releasable positioning jig 1512 but has a flatter configuration in the proximal-distal direction.

The releasable positioning jig 1662 includes a first aperture 1690 and a second aperture 1694, which are configured to receive the first projection 1518 and the second projection 1520 respectively. The releasable positioning jig 1662 includes an aperture 1170 formed through a boss 1168. The aperture 1170 defines an axis 1171 along which the guide pin 1016 can be guided into the humerus 12 following resection, in a manner similar to that discussed and shown in connection with FIG. 31D.

Figure 43:
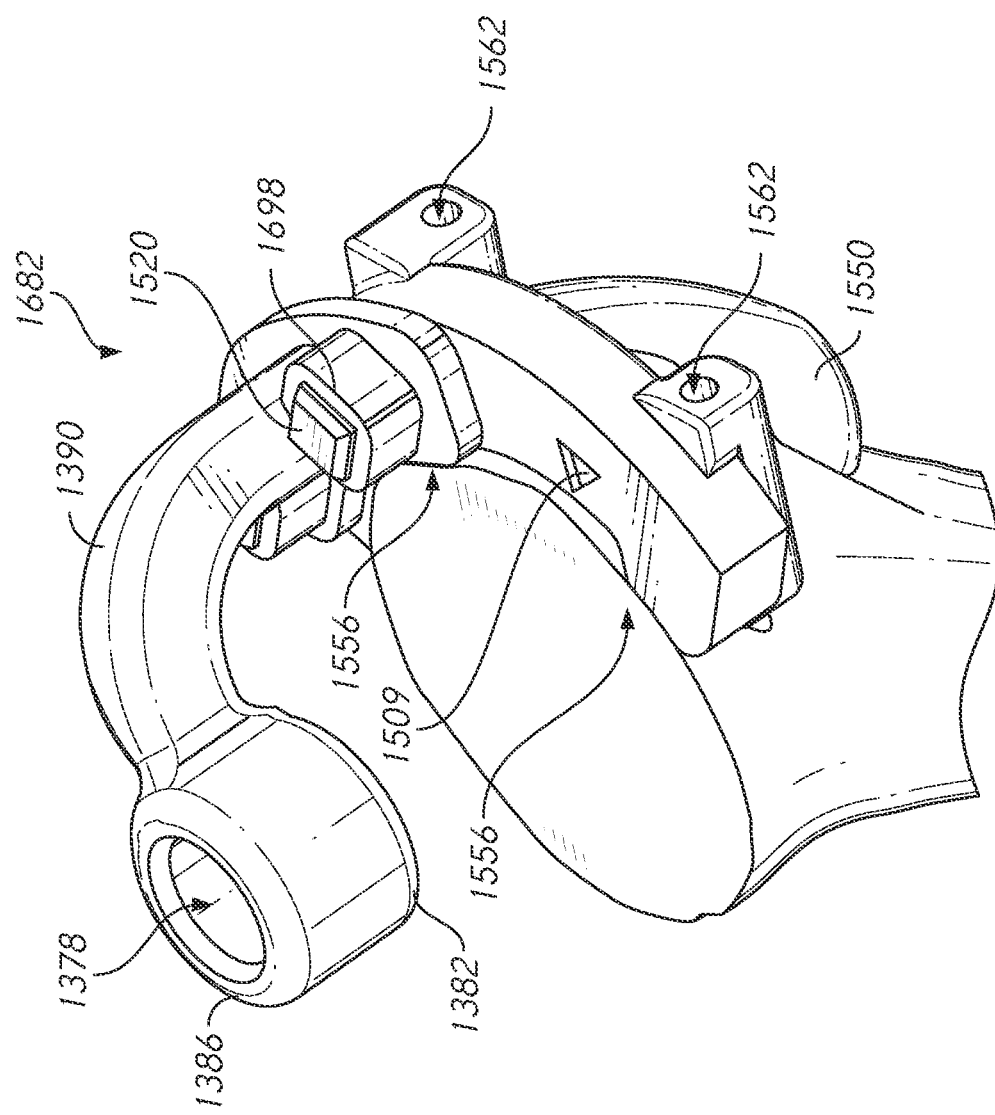
FIG. 43 is a perspective view of another embodiment of a releasable positioning jig for guiding a reamer, the releasable positioning jig being coupled with the support portion of FIG. 39.

FIG. 43 shows that the support portion 1506 also can advantageously be connected to a releasable positioning jig 1682. The releasable positioning jig 1682 is similar to the releasable positioning jig 1362, and like features have the same reference numbers. One difference is that the releasable positioning jig 1682 has a first aperture 1690 and a second aperture 1694 configured to engage the first projection 1518 and the second projection 1520 respectively. As such the releasable positioning jig 1682 is able to symmetrically respond to loading by transferring loads through interfaces located on both sides of a longitudinal axis of the projection 1390 of the releasable positioning jig 1682. Thus, when the shaft 1124 of the reamer 1120 (see FIG. 37G) is advanced through the second end 1386 of the aperture 1378 and further through the first end 1382 to engage the reamer head 1128 and is thereafter operated according to the arrow A8, loads will be transferred through an interface on either or both sides of the longitudinal axis of the projection 1390.

The humeral cutting guides humeral cutting guide 1200 1500 allows for quick connection of the several different releasable positioning jigs. For example after the guide pin 1016 is placed, the releasable positioning jig 1362 can be coupled to the support portion 1206 to guide the shaft 1124 as the shaft 1124 rotates the reamer head 1128. The aperture 1378 is much larger than the aperture 1286 and thus can accept the larger shaft 1124 which can be cannulated to operate over the guide pin 1016. Although the first projection 1518 and the second projection 1520 take up some of the space on the resection surface 1504, they provide for enhanced stability of the releasable positioning jig 1512 and other releasable jigs of the humeral cutting guide 1500.

IV. Cancellous Bone Preparation Components

FIGS. 44A-44D show various methods that involve the use of the support portion 1506 to guide subsequent portions of methods of preparing cancellous bone following the resection of the humerus 12 to enable a humeral stem to be placed in the humerus 12 with ease.

Figure 44A:
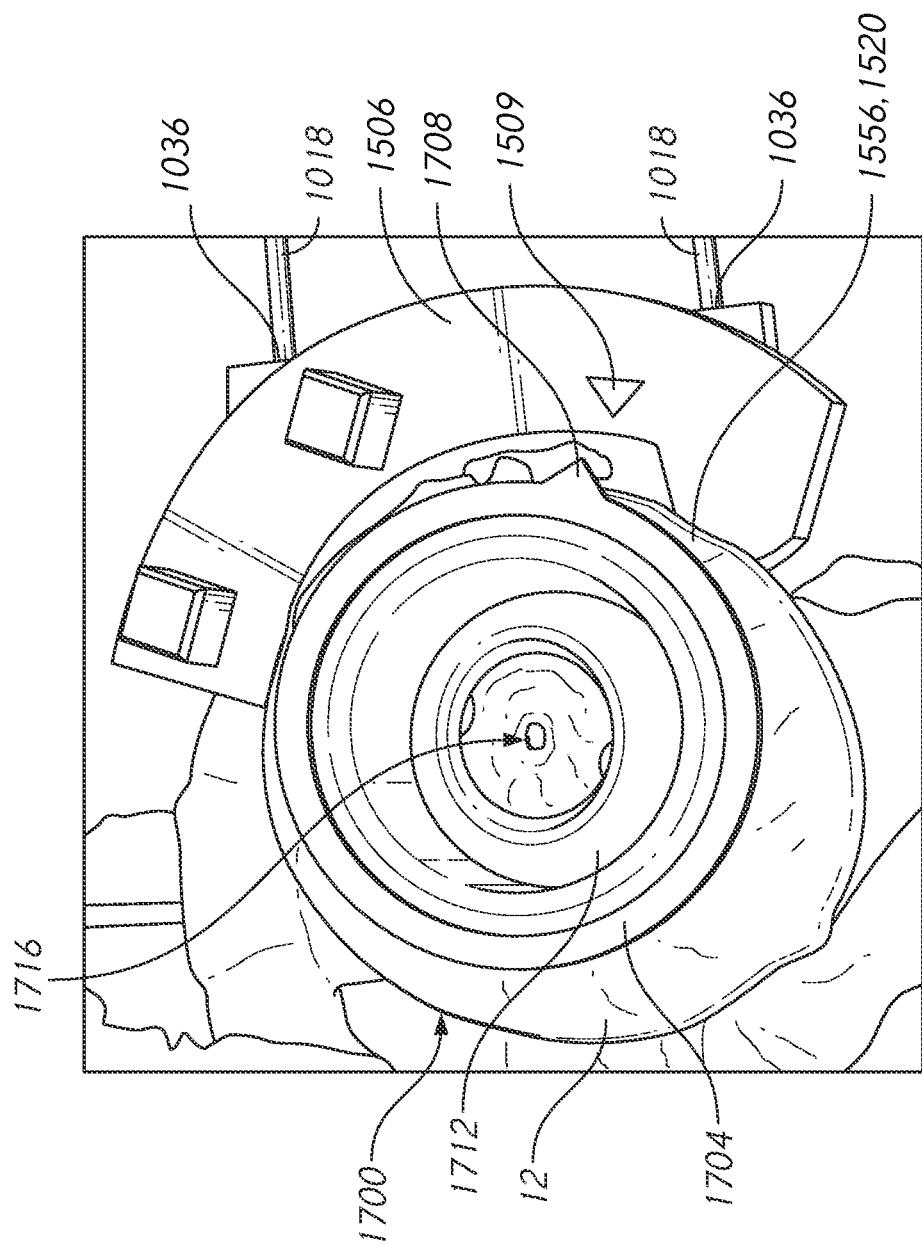
FIG. 44A shows a broaching guide positioned on and the resected humerus, the broaching guide configured to rotationally orient and guide a broaching tool to be advanced into the humerus.

FIG. 44A shows the support portion 1506 coupled with the humerus 12. However, the other guides described herein could also be used in the methods that follow. Following resection a stem location guide 1700 can be placed on the resected surface of the humerus 12. The stem location guide 1700 can include a peripheral member 1704 with a directional indictor 1708 located on a periphery of the peripheral member 1704. The directional indictor 1708 can include a pointer structure such as a triangular projection that comes to an apex outward of the circumference of the rest of the peripheral member 1704. The directional indictor 1708 can extend outward of the outer circumference of the rest of the peripheral member 1704 to provide a visually distinct zone for alignment. The stem location guide 1700 also can include a vault portion 1712 that extends away from the peripheral member 1704 such that if the peripheral member 1704 is placed flush with the resected surface of the humerus 12 the vault portion 1712 will project into the cancellous bone below, inferior to, or distal to the resection surface. The vault portion 1712 can include a stem tamp aperture 1716 disposed in a central portion of thereof. The stem tamp aperture 1716 need not be centered on the geometric center of the peripheral member 1704 but can be in some cases. The location of the stem tamp aperture 1716 can be patient specific in that it defines the start of a channel that will be formed by the procedures that are described below. It may be pre-planned based on pre-operative analysis that the channel is centered in the bone mass, is spaced a minimum distance form outer cortical wall portions or that the channel meet other pre-operative planning objectives.

Figure 44B:
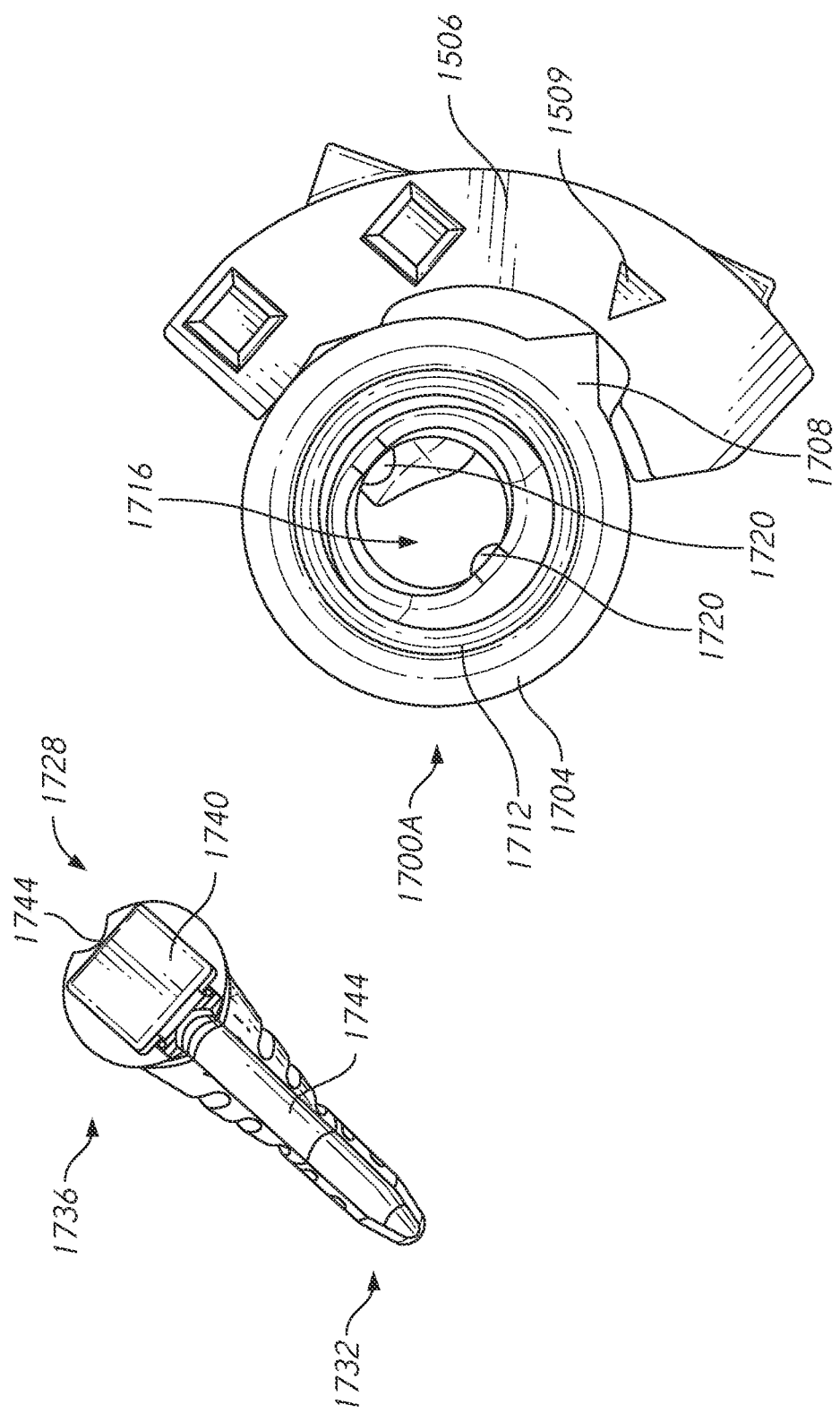
FIG. 44B illustrates placing a broaching tool into the resected humerus through the broaching guide shown in FIG. 44A.

FIG. 44A shows the periphery of the stem tamp aperture 1716 with a smooth configuration. FIG. 44B shows that in another embodiment a stem location guide 1700A can include one or a plurality of guide protrusions 1720. The guide protrusion 1720 can be formed as a semicircular protrusion extending into the stem tamp aperture 1716. The guide protrusion 1720 help to guide a stem tamp 1728. The stem tamp 1728 can include a first end 1732 and a second end 1736. The first end 1732 is configured to be inserted first through the stem tamp aperture 1716 and can be tapered, e.g., of a smaller periphery than the second end 1736. The second end 1736 can include a tool interface 1740 configured to allow the stem tamp 1728 to be coupled to a inserter 1750. The tool interface 1740 can take any suitable form, but in the illustrated embodiment is a square profile projection that extends away from the first end 1732. The stem tamp 1728 includes one or a plurality of guide rails 1744 that are configured to guide the stem tamp 1728 as the stem tamp 1728 is inserted into the humerus 12 beneath the resection surface. The guide rail 1744 can be an elongate channel with a curved, e.g., a semicircular cross-sectional profile. The guide rail 1744 can extend between the first end 1732 and the second end 1736, e.g., from the second end 1736 toward the first end 1732 and in one case entirely from the second end 1736 to the first end 1732.

A method following the step shown in FIG. 44A can involve coupling the inserter 1750 with the tool interface 1740 of the stem tamp 1728. The inserter 1750 can then be moved to cause the first end 1732 to enter the vault portion 1712 and thereafter to pass through the stem tamp aperture 1716. Continued insertion of the stem tamp 1728 can cause the tamp to advance the guide rails 1744 thereof into engagement with the guide protrusion 1720. The interaction between the guide protrusions 1720 and the guide rails 1744 can enable the stem tamp 1728 to follow a pre-planned pathway into the humerus 12 to cause a channel formed thereby to be in the location as pre-planned.

Figure 44C:
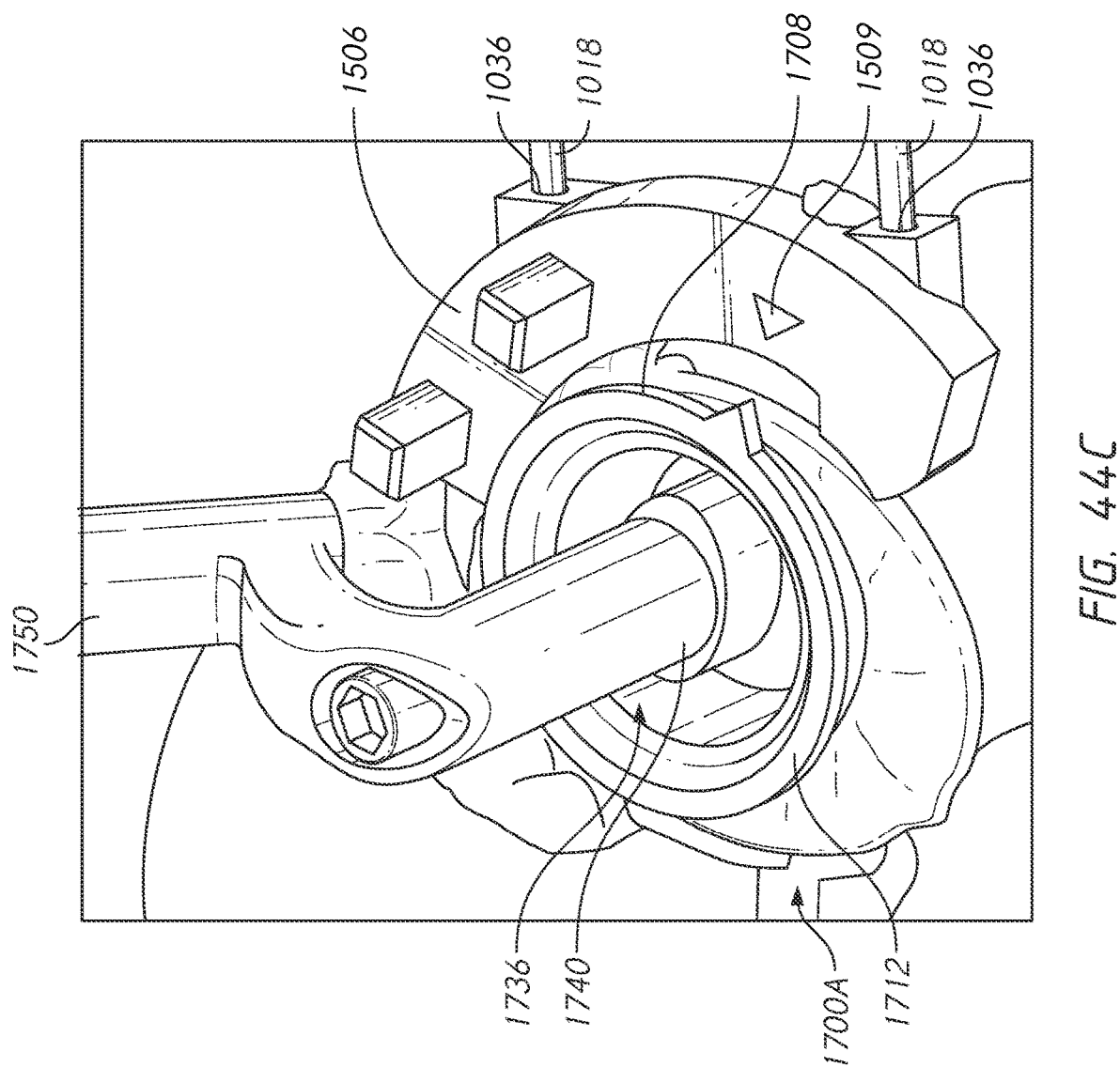
FIG. 44C shows a top view of the broaching tool positioned in the humerus through the broaching guide.
Figure 44D:
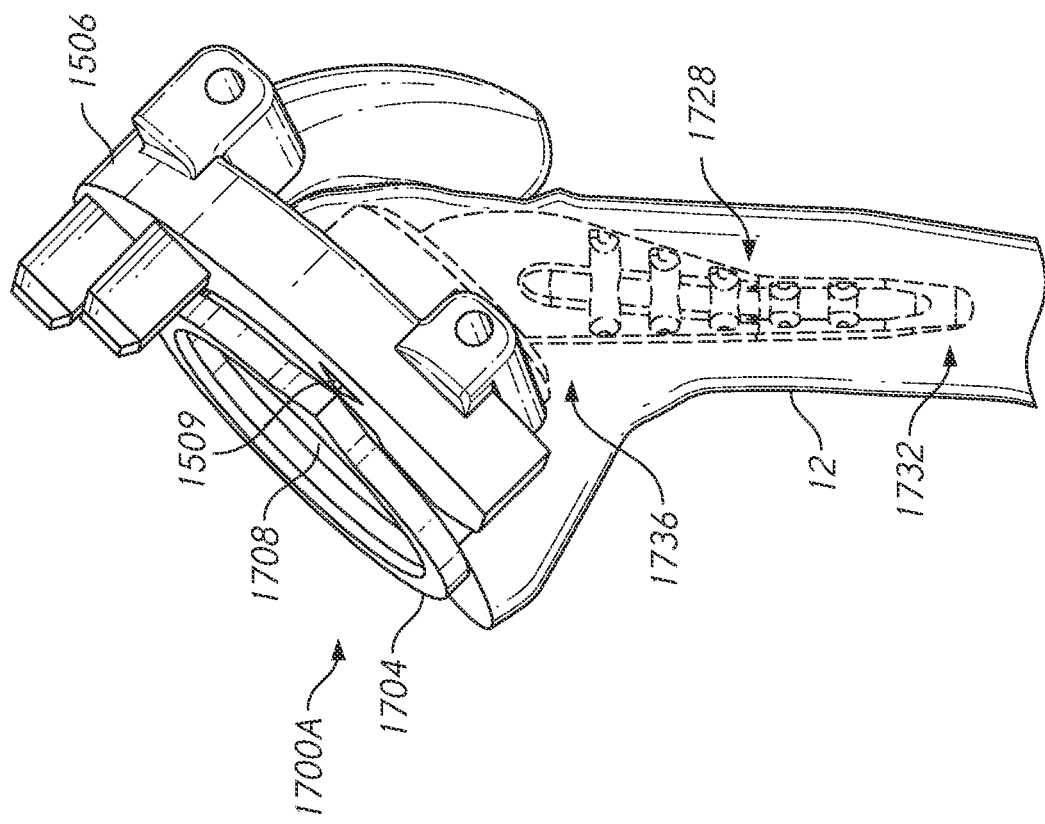
FIG. 44D is a side view of the humerus with the broaching tool positioned in the humerus.

FIGS. 44C-44D show the stem tamp 1728 fully inserted into the stem location guide 1700. The rotational position of the stem tamp 1728 is controlled by first aligning the directional indictor 1708 with the surgical cue 1509. The rotational position of the stem tamp 1728 to the stem location guide 1700 is controlled by the interaction of the guide rail(s) 1744 with the guide protrusion(s) 1720. FIG. 44D shows the stem tamp 1728 disposed in the bone mass of the humerus 12. The stem tamp 1728 can be seen to be generally centered in the medial-lateral direction (left and right on the page). The stem tamp 1728 may also be generally centered in the anterior-posterior direction (into and out of the page) relative to the bone mass. In some planning methods, it may be determined that it is preferable to shift the stem tamp 1728 toward the medial and away from the lateral wall of the humerus 12. In other planning methods, it may be determined that it is preferable to shift the stem tamp 1728 toward the lateral and away from the medial wall of the humerus 12. In other planning methods, it may be determined that it is preferable to shift the stem tamp 1728 toward the anterior and away from the posterior wall of the humerus 12. In other planning methods, it may be determined that it is preferable to shift the stem tamp 1728 toward the posterior and away from the anterior wall of the humerus 12. In other planning methods, it may be determined that it is preferable to shift the stem tamp 1728 in another direction toward a wall of the humerus and/or in another direction away from a wall of the humerus 12. Such positioning can be controlled by the combination of the support portion 1506 (or other guides), the stem location guide 1700, and the stem tamp 1728.

V. Humeral Guide Planning Methods for Enhancing Bone Attachment Security

FIGS. 45-50 provide additional disclosure of methods for planning and providing tools that can facilitate orthopedic surgery.

Figure 45:
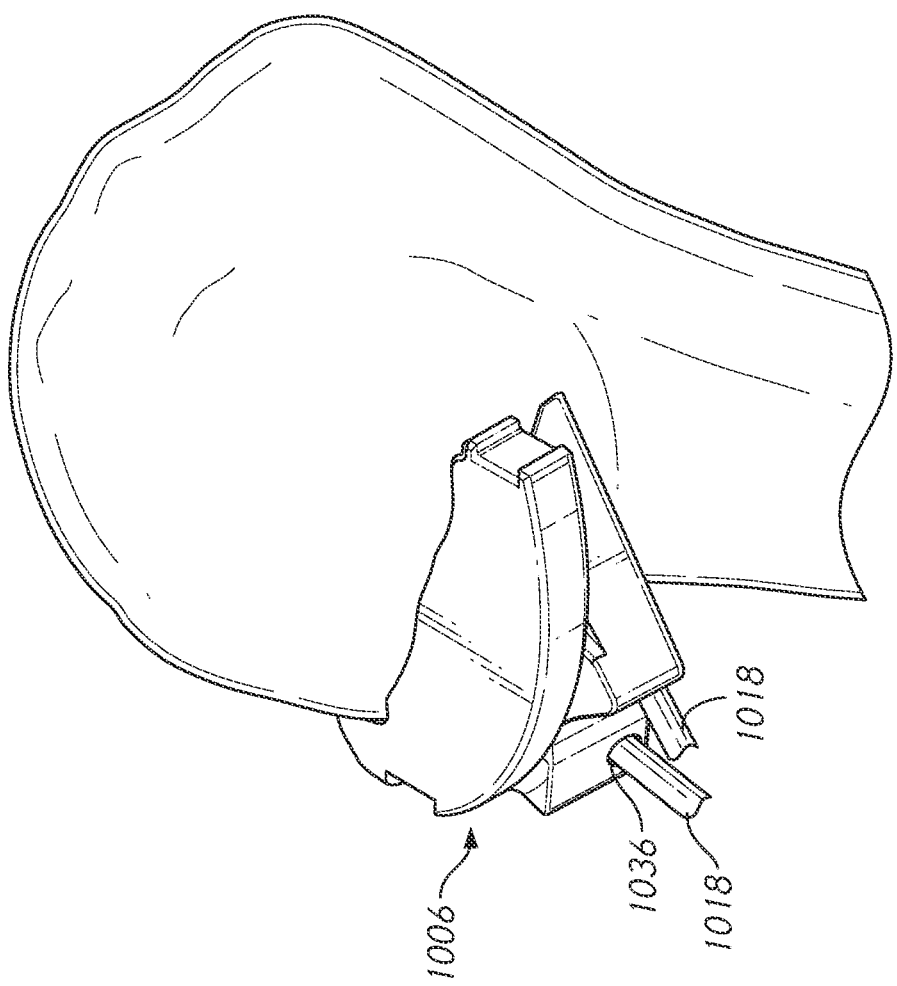
FIG. 45 is a perspective view of the support portion of FIG. 24 and mounting pins used to secure the support portion.

FIG. 45 shows a humerus 12 with the support portion 1006 of the humeral cutting guide 1000 coupled with a face of the bone. Stabilization pins 1018 are shown inserted into the humerus 12 through mounting pin holes 1036 as discussed above. As discussed above in connection with FIG. 31B it is preferred that the stabilization pins 1018 be directed along diverging paths 1040, which are defined along longitudinal axes 1044 of the mounting pin holes 1036. The following is a discussion of methods of selecting where the longitudinal axis or axes 1044 should be with reference to the anatomy of the specific patient.

FIG. 3 shows that the planning system 54 can have a module 67 that establishes a configuration for any of the guides disclosed herein. For illustrative purposes, the discussion that follows relates to forming the humeral cutting guide 1000 and the components thereof. But, the methods are equally applicable to the other guides, e.g., the humeral cutting guide 1200, the humeral cutting guide 1500, or to just the support portions thereof or to the various monolithic guides discussed above. The module 67 can have a portion that is directed to configuring the humeral cutting guide 1000 for an anterior approach. The humeral cutting guide 1000 or other guides or supports therefore can be configured for other approaches, such as posterior, lateral, antero-lateral, and/or postero-lateral. The desired approach can be selected by and/or input into the module 67. The module 67 can have a portion that is directed to one piece or monolithic guide formation, where it is desired to eliminate any intra-operative assembly of the guide. The module 67 has a portion that is directed to forming a multi-component guide, such as the edge clip humeral cutting guide 1000, the single post mount humeral cutting guide 1200, or the dual post mount humeral cutting guide 1500. The module 67 has a portion that considers whether to configure the support portion 1006 and the arrangement of the support pins that support the support portion 1006 to avoid a space to be occupied by an implant. That is, part of selecting the diverging paths 1040 and the longitudinal axis 1044 will be whether to leave enough space to allow the implant to be placed in the humerus at the same time as the stabilization pins 1018. Other options for controlling parameters of the humeral cutting guide 1000 can be selected in the module 67. For example the module can have a portion that identifies and causes the diverging paths 1040 and the longitudinal axis 1044 to achieve good support in the bone.

After the pre-operative shoulder images 62 are obtained and provided to the planning system 54, the system and the module 67 analyze the condition of the bone. Based on the condition of the bone the planning system 54 and the module 67 determine where to position and how to orient the mounting pin holes 1036. The planning system 54 and the module 67 determine where the longitudinal axis 1044 should be directed in the bone from the mounting pin holes 1036 when the support portion 1006 is properly placed.

More particularly, the planning system 54 can be used to plan a resection of a bone, such as the humerus 12. The planning system 54 can be used to plan a resection of the humerus 12 from an anterior approach or other bone, e.g., using the support portion 1006. One of several contact areas 1020 can be identified as available in the anterior approach. The bone distal to the resection surface 1004 can be evaluated to determine the condition thereof for receiving the stabilization pins 1018. For example, a virtual model of the humerus 12 can be constructed from the pre-operative shoulder images 62. The model can have sufficient detail to evaluate the condition of the bone.

Figure 46:
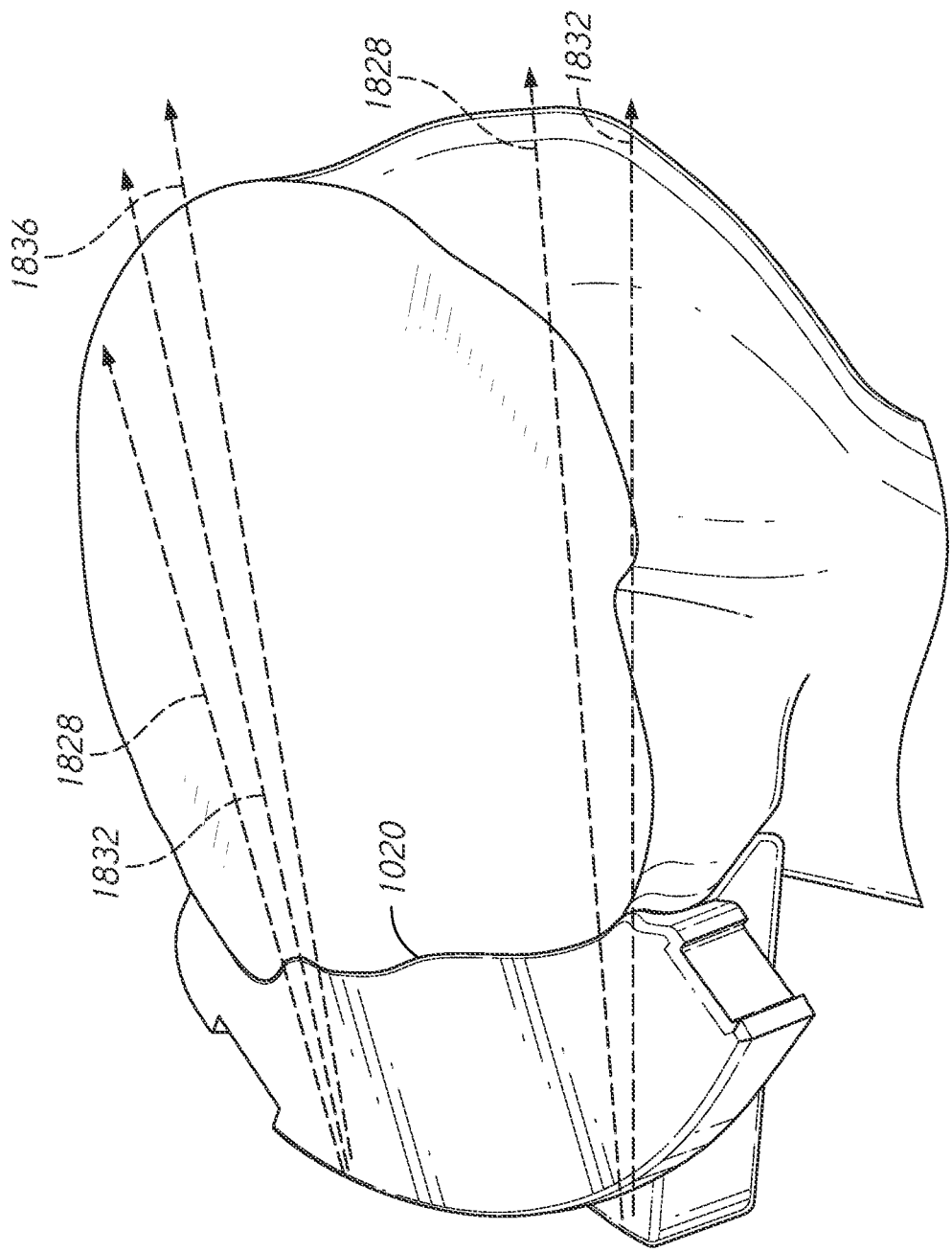
FIG. 46 is a top perspective view of the resected humerus showing a plurality of possible guide pin trajectory.

FIG. 46 shows that the model can be configured to select among a plurality of possible support pin pathways, for example among a first support pin pathway 1828, a second support pin pathway 1832, and a third support pin pathway 1836. Each of these pathways can be analyzed as extending from an anterior side of the humerus 12 to a posterior side thereof. The pathways can be seen to extend from an outside surface of the humerus 12 through a layer of cortical bone 1806 on the left-hand side of the figure into a mass of cancellous bone 1804 and then through a second layer of cortical bone 1806 on the right-hand side of the figure.

Figure 47:
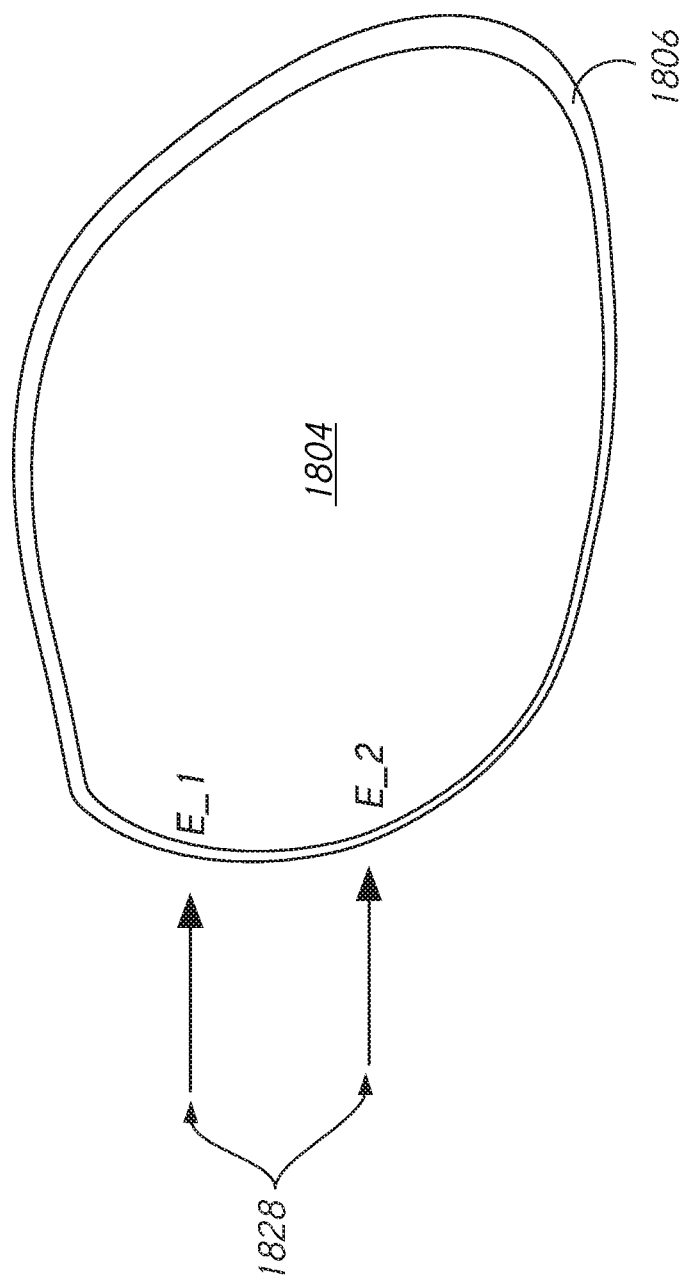
FIG. 47 shows a schematic section of a humerus illustrating a technique for selecting among two potential guide pin pathways at spaced apart entry points.

FIG. 47 shows one technique for selecting between two spaced apart locations on the outer surface of the humerus 12 for a pathway, e.g., for the first support pin pathway 1828. Imaging data is analyzed to confirm that the thickness $E\_1$ of the cortical bone layer 1806 at a first location. The thickness $E\_2$ of the cortical bone layer 1806 at a second location is also confirmed. All other factors being equal the planning system 54 or the user directing the planning system 54 selects the entry point corresponding to the thickness $E\_1$ at the first location for the first support pin pathway 1828.

Figure 48:
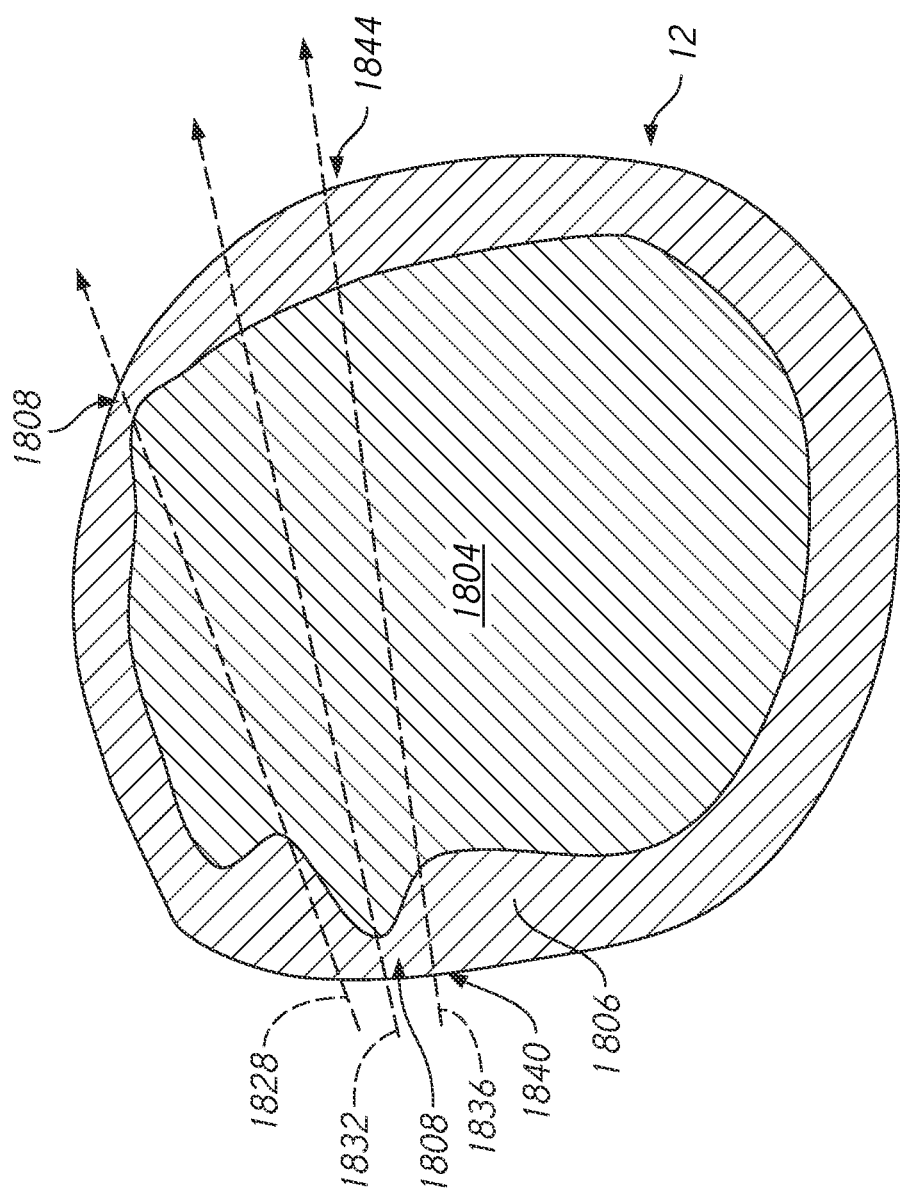
FIG. 48 illustrates another technique similar to that of FIG. 47, illustrating selecting from a plurality of pathways at close or the same entry point.

FIG. 48 shows methods where multiple trajectories are considered for multiple closely adjacent or for a single entry point. The second support pin pathway 1832 can be seen to pass through thin bone matter 1808. The thin bone matter 1808 can be a portion of the humerus 12 where the cortical bone 1806 is thinner and the cancellous bone 1804 is closer to an outer surface of the humerus 12. Another area of thin bone matter 1808 can be seen on the posterior side of the humerus 12 (on the right hand side of the figure) at the location that the first support pin pathway 1828 passes through posterior surface (right hand side of the figure) of the humerus 12 as modeled.

The pathways can be defined by entry and exit points. For example the second support pin pathway 1836 can have a patient specific entry point 1840 and a patient specific trajectory 1844. A total pin path length disposed within the bone can be calculated in the planning system 54 as the distance from the pin entry on the anterior side of the humerus 12 (left hand side of the figure) to a pin exit on the posterior side (right hand side of the figure) of the humerus 12. In one strategy for patient matching the pin trajectory, the patient matched jig provides at least and in some cases more than a minimum length of pin that traverses bone (between the entry and exit) when the jig is placed in a preoperatively planned position and the stabilization pin is advanced through the hole and into the bone In a method, a virtual representation of the support portion 1006 is placed according to the planned resection. The representation can be on a user interface of a display. Outer and inner contours of the cortical bone 1806 can be displayed as well. The first support pin pathway 1828, the second support pin pathway 1832, and the third support pin pathway 1836 can be displayed, e.g., overlaid on the display similar to the schematic representation of FIG. 47. The pathways first support pin pathway 1828, 1832, 1836 can have the same or different entry points. From the display or from an analysis of the pre-operative shoulder images 62, the location of the thin bone matter 1808 or other non-supportive bone matter can be determined. The preoperatively planned pathway(s) 1828, 1832, 1836 can be selected to avoid the thin bone matter 1808 or other non-supportive bone matter. In another approach, a patient matched jig can provide at least a minimum and in some cases more than a minimum cortical bone traverse when the jig is placed in a preoperatively planned position and the stabilization pin is advanced through the hole and into the bone. That is the lengths of portion of the stabilization pin 1018 in the anterior cortical bone layer 1806 can be required to exceed a minimum threshold of approximately 0.5 mm, in some cases 1 mm, in some cases 2 mm, in some cases 3 mm, in some cases 4 mm, in some cases 5 mm, and in other cases 6 mm or more. The length of the stabilization pin 1018 in the posterior cortical bone layer 1806 can be required to exceed a minimum threshold of approximately 0.5 mm, in some cases 1 mm, in some cases 2 mm, in some cases 3 mm, in some cases 4 mm, in some cases 5 mm, and in other cases 6 mm or more. The sum of pin length in the anterior and posterior cortical bone layer 1806 can be required to exceed a minimum threshold, e.g., approximately 0.5 mm, in some cases 1 mm, in some cases 2 mm, in some cases 3 mm, in some cases 4 mm, in some cases 5 mm, and in other cases 6 mm or more.

The planning system 54 can automatically select the best path among the paths first support pin pathway 1828, the second support pin pathway 1832, and the third support pin pathway 1836. Or, the user can be presented with an interface that suggests pathways that satisfy minimum requirements, allowing the user to select among such pathway.

For example, the first support pin pathway 1828 extends through what is illustrated as the thickest layer of cortical bone 1806 on the anterior side of the bone. The first support pin pathway 1828 however also extends through thin bone matter 1808 on the posterior side. The second support pin pathway 1832 extends through thin bone matter 1808 on the anterior side of the humerus 12 and extends through relatively thicker cortical bone 1806 on the posterior side of the humerus 12. The third support pin pathway 1836 may provide a preferred pathway in that the pin pathway 1836 extends through relatively thick cortical bone 1806 on both sides of the cancellous bone 1804 of the humerus 12.

One variation of these methods can involve first selecting a patient specific entry point 1840. The patient specific entry point 1840 can be selected based on the absence of fragile osteophytes at that location or on other bases. Once patient specific entry point 1840 is selected the trajectory of the support pin pathway can be determined by avoiding thin cortical wall sections at the same side of the humerus 12 as the entry point, by avoiding thin cortical wall sections on the opposite side of the humerus 12 as the entry point, or by avoiding thin cortical wall sections on the same and on the opposite side of the humerus 12 as the entry point.

Another approach can start with a preferred patient independent pathway. For example, it may be desired to allow the support portion 1006 to remain in place on the humerus 12 when the bone preparation beneath the resection is being performed or until after the final bone anchor is placed. The diverging paths 1040 defined through the mounting pin holes 1036 can therefore be pre-set to provide trajectories that would keep the stabilization pins 1018 outside of the portion of the humerus 12 to be prepared and/or to receive the implant anchor. One or more patient independent entry point and trajectories can thus be selected based on this or other criteria. The path defined by the patient independent entry point and trajectory can be compared with location information for non-supportive bone matter, as discussed above. The method can further involve excluding pathways that are too close to the non-supportive matter.

Figure 49:
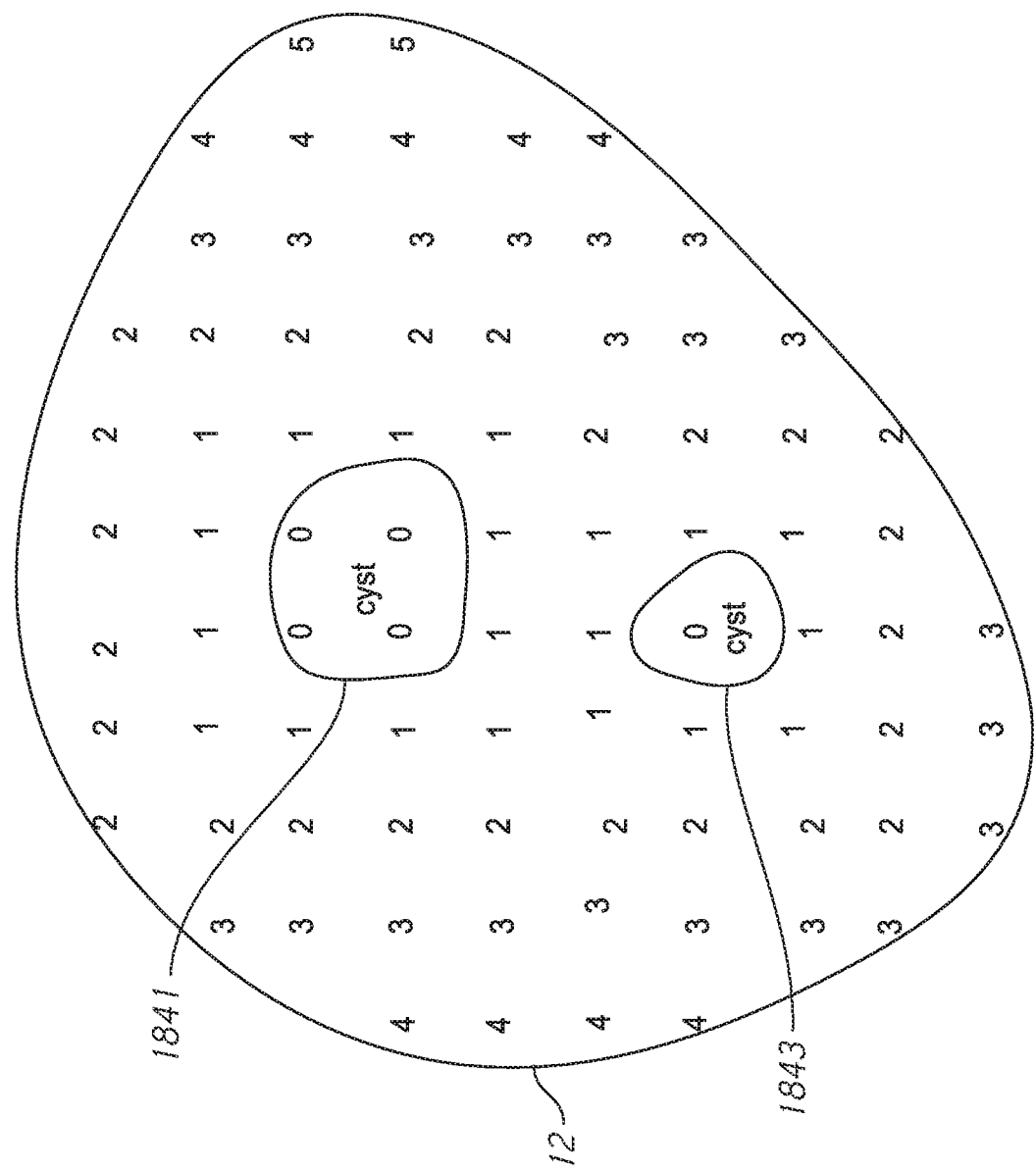
FIG. 49 illustrates techniques for analyzing a humerus to enable pin placement that avoids a traverse of a subsurface cyst.

FIG. 49 illustrates methods in which non-supportive bone matter can be identified and avoided in various methods. Two sub-surface cysts, labeled "cyst" are illustrated. The cysts are located in cancellous bone matter. In one method, a first boundary 1841 is drawn around one of the cysts and a second boundary 1843 is drawn around one of the cysts. The boundaries can be actually displayed or just form a part of a method or algorithm. The display shows an indication of distance from the cysts. Within the boundaries 1841, 1843 a number "0" is displayed. A map of distances from the cyst in millimeters can be presented to the user, as illustrated in FIG. 49. Away from the cysts the numbers increase, indicating spacing in mm from the cysts. A method can require the acceptable paths to be at least a minimum distance in millimeters (or other dimensions) from the cysts (e.g., a 1 mm, 2 mm, 3 mm at minimum, or an average value greater than a threshold, and other variations). The cysts are one example of fragile bone matter. This approach can also work with fragile osteophyte or other delicate matter. These methods and other approaches to detecting bone strength can be obtained from the pre-operative shoulder images 62. These methods can be used to select or to confirm an appropriate support pin pathway to temporarily attach the cut guide to the bone.

The map of FIG. 49 can alternatively display a gradient of bone density, identifying low density portion within the boundaries 1841, 1843 and higher density portions around the boundaries as areas to traverse with a stabilization pin 1018. The map of FIG. 49 can display a gradient of bone density, identifying high density portion within boundaries 1841, 1843 and lower density portions around the boundaries. In this mode, the path to be chosen is one in which the stabilization pin 1018 traverses through the higher density zone within the boundary.

A comparison on non-excluded pathways can be objectively conducted. For example the non-excluded pathways can be evaluated by determining a length of the pathways not excluded. An overall length from entry to exit point of the pathways could be compared and the longer pathway selected. A length of each of multiple pathways through cortical bone could be determined and compared and the pathway with a greater amount of cortical traverse could be selected. Other combined objected metrics could be used. In one variation the planning system 54 is configured to generate and output, e.g., to a visual display overlying a representation of the humerus 12, a plurality of non-excluded pathways that are provide sufficient support. The planning system 54 can allow the user to select among these non-excluded pathways.

FIG. 48 shows that an analysis of the support pin pathways can be conducted on each side of the support portion 1006. The analysis of the bone quality for purposes of configuring the interface between the humeral cutting guide 1000 and the humerus 12 can apply to the positioning jig 1212 as well. For example, the contact area 1068 of the releasable positioning jig 1012 can be configured to engage bone with sufficient strength to support the loads applied to the humerus 12 in any steps in which the releasable positioning jig 1012 is coupled with the support portion 1006.

Figure 50:
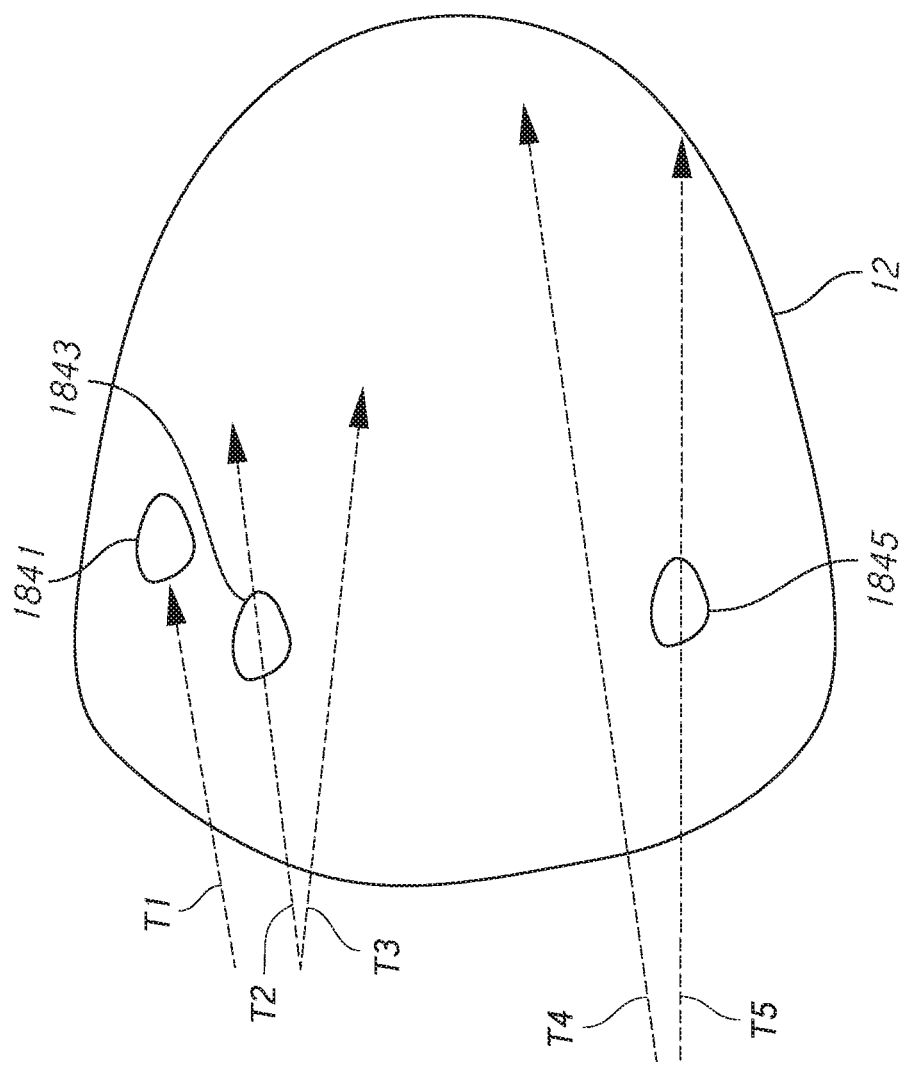
FIG. 50 illustrates the selection among a plurality of pathways considering pathway length and the potential presence of subsurface cysts.

FIG. 50 show an analysis can be made of many different trajectories. Trajectory T1 is deemed acceptable if the insertion of the stabilization pins 1018, though directed toward the cyst within the boundary 1841 does not traverse the boundary and the cyst. An insertion limit can be facilitated by providing a patient matched stabilization pin 1018 with a marking or a length that assists the surgeon in not over-inserting into the cyst within boundary 1841. In contrast the trajectory T2 is deemed unacceptable because it traverses the cyst within the boundary 1843. The trajectory T2 could be considered acceptable if other aspects of the trajectory enhance the strength of the connection between the stabilization pins 1018 and the humerus 12, e.g., if the length of contact with cortical bone is higher than a threshold level, e.g., greater than approximately 3 mm, in some cases 4 mm, in some cases 5 mm, and in other cases 6 mm or more. The trajectories T3 and T4 are both deemed acceptable in that they do not traverse a cyst. Trajectories T3 and T4 are converging and thus provide good retention and stability for a guide or support portion on the humerus 12. Trajectory T5 is deemed unacceptable in that it traverses a cyst within boundary 1845. Thus, FIG. 50 illustrates a method that evaluates a plurality of possible paths and prevents directing a stabilization pin 1018 through non-supportive bone matter, such as a cyst.

Terminology

Although certain embodiments have been described herein, the implants and methods described herein can interchangeably use any articular component, as the context may dictate.

As used herein, the relative terms "proximal" and "distal" shall be defined from the perspective of the humerus. Thus, proximal refers to the direction of the end of the humerus adjacent to the scapula and forming part of the shoulder joint, which may be referred to herein as the superior direction, end or portion, and distal refers to the direction away from proximal, which can be the end of the humerus forming part of the elbow joint and which may be referred to herein as the inferior direction, end or portion of the humerus.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a humeral stem into a humerus" include "instructing insertion of a humeral head into a humerus."

What is claimed is:

1. A humeral guide, comprising:
    a jig having a patient matched surface and a hole for a stabilization pin, wherein an orientation of the hole is patient matched;
    a support portion including a resection surface;
    a connection mechanism that connects the jig to the support portion and includes a projection on the support portion that is adapted to extend into an aperture of the jig such that the jig is releasable from the support portion; and
    the stabilization pin adapted to be advanced through the hole, wherein
    the orientation of the hole defines at least a minimum length of the stabilization pin traversing bone when the jig is placed in a preoperatively planned position and the stabilization pin is advanced through the hole and into the bone.

2. The humeral guide of claim 1, wherein the jig comprises two holes, each hole defining an orientation, at least one of the orientations being patient matched, the at least two holes being arranged along non-parallel axes.

3. The humeral cutting guide of claim 1, wherein the jig is configured to guide a guide pin through a resection plane of the humerus and into the cancellous bone distal thereof.

4. The humeral cutting guide of claim 3, wherein the jig comprises a hole defining a patient matched orientation configured to guide further preparation of the humerus distal to a plane of resection of the humerus.

5. A humeral guide, comprising:
    a jig having a patient matched surface and a hole for a stabilization pin, wherein an orientation of the hole is patient matched;
    a support portion including a resection surface;
    a connection mechanism that connects the jig to the support portion and includes a projection on the support portion that is adapted to extend into an aperture of the jig such that the jig is releasable from the support portion; and
    the stabilization pin adapted to be advanced through the hole, wherein
    the orientation of the hole provides a minimum cortical bone traverse when the jig is placed in a preoperatively planned position and the stabilization pin is advanced through the hole and into the bone.

6. The humeral guide of claim 5, wherein the jig comprises two holes, each hole defining an orientation, at least one of the orientations being patient matched, the at least two holes being arranged along non-parallel axes.

7. The humeral cutting guide of claim 5, wherein the jig is configured to guide a guide pin through a resection plane of the humerus and into the cancellous bone distal thereof.

8. The humeral cutting guide of claim 7, wherein the jig comprises a hole defining a patient matched orientation configured to guide further preparation of the humerus distal to a plane of resection of the humerus.

9. A humeral guide, comprising:
    a jig having a patient matched surface and a hole for a stabilization pin, wherein an orientation of the hole is patient matched;
    a support portion including a resection surface;
    a connection mechanism that connects the jig to the support portion and includes a projection on the support portion that is adapted to extend into an aperture of the jig such that the jig is releasable from the support portion; and
    the stabilization pin adapted to be advanced through the hole, wherein
    the orientation of the hole avoids a sub-cortical cyst traverse when the jig is placed in a preoperatively planned position and the stabilization pin is advanced through the hole and into the bone.

10. The humeral guide of claim 9, wherein the jig comprises two holes, each hole defining an orientation, at least one of the orientations being patient matched, the at least two holes being arranged along non-parallel axes.

11. The humeral cutting guide of claim 9, wherein the jig is configured to guide a guide pin through a resection plane of the humerus and into the cancellous bone distal thereof.

12. The humeral cutting guide of claim 11, wherein the jig comprises a hole defining a patient matched orientation configured to guide further preparation of the humerus distal to a plane of resection of the humerus.

13. The humeral guide of claim 9, wherein the jig provides a minimum clearance distance from a sub-cortical cyst to the stabilization pin when the jig is placed in a preoperatively planned position and the stabilization pin is advanced through the hole.

* * * * *